US012274283B2

(12) United States Patent
Pattillo et al.

(10) Patent No.: US 12,274,283 B2
(45) Date of Patent: Apr. 15, 2025

(54) ENHANCED AEROBIC FERMENTATION METHODS FOR PRODUCING EDIBLE FUNGAL MYCELIUM BLENDED MEATS AND MEAT ANALOGUE COMPOSITIONS

(71) Applicant: The Better Meat Co., West Sacramento, CA (US)

(72) Inventors: Augustus H. Pattillo, West Sacramento, CA (US); Moran Farhi, West Sacramento, CA (US); Katherine Ruwe, West Sacramento, CA (US)

(73) Assignee: THE BETTER MEAT CO., West Sacramento, CA (US)

( * ) Notice: Subject to any disclaimer, the term of this patent is extended or adjusted under 35 U.S.C. 154(b) by 418 days.

(21) Appl. No.: 17/739,725

(22) Filed: May 9, 2022

(65) Prior Publication Data

US 2022/0330593 A1 Oct. 20, 2022

Related U.S. Application Data

(63) Continuation-in-part of application No. 16/586,150, filed on Sep. 27, 2019, now Pat. No. 11,470,871,
(Continued)

(51) Int. Cl.
*A23L 31/00* (2016.01)
*A23J 3/04* (2006.01)
(Continued)

(52) U.S. Cl.
CPC ............... *A23L 31/00* (2016.08); *A23J 3/04* (2013.01); *A23J 3/14* (2013.01); *A23J 3/20* (2013.01);
(Continued)

(58) Field of Classification Search
CPC .............. A23J 1/008; A23J 3/227; C12N 1/14
See application file for complete search history.

(56) References Cited

U.S. PATENT DOCUMENTS

| | | |
|---|---|---|
| 1,822,227 A | 9/1931 | Lendrich et al. |
| 2,450,055 A | 9/1948 | Nord |
| | (Continued) | |

FOREIGN PATENT DOCUMENTS

| | | |
|---|---|---|
| AT | 101660 B | 7/1922 |
| CN | 1094258 A | 11/1994 |
| | (Continued) | |

OTHER PUBLICATIONS

U.C. Banerjee "Effects of substrate particle size and alkaline pre-treatment on protein enrichment by Neurospora sitophila", Resources, Conservation and Recycling vol. 13, Issue 2, May 1995, pp. 139-146 (Year: 1995).*
(Continued)

*Primary Examiner* — Michele L Jacobson
(74) *Attorney, Agent, or Firm* — McDonnell Boehnen Hulbert & Berghoff LLP

(57) ABSTRACT

Provided herein are shelf-stable protein food ingredients, food products comprising the shelf-stable protein food ingredients, methods of their production, and methods of their use. The shelf-stable protein food ingredients comprise cultured fungal biomass and a limited amount of water. Advantageously, the shelf-stable protein food ingredients can be stored, transported, and delivered within the food supply.

26 Claims, 21 Drawing Sheets

Related U.S. Application Data which is a continuation of application No. 16/578,099, filed on Sep. 20, 2019, now Pat. No. 11,058,137.

(60) Provisional application No. 63/185,902, filed on May 7, 2021, provisional application No. 62/733,925, filed on Sep. 20, 2018.

(51) Int. Cl.
| | |
|---|---|
| *A23J 3/14* | (2006.01) |
| *A23J 3/20* | (2006.01) |
| *A23J 3/22* | (2006.01) |
| *A23K 10/12* | (2016.01) |
| *A23K 50/40* | (2016.01) |
| *A23L 13/40* | (2023.01) |
| *C12N 1/14* | (2006.01) |
| *C12P 21/00* | (2006.01) |

(52) U.S. Cl.
CPC ............ *A23J 3/227* (2013.01); *A23K 10/12* (2016.05); *A23K 50/40* (2016.05); *A23L 13/424* (2016.08); *A23L 13/46* (2016.08); *C12N 1/14* (2013.01); *C12P 21/00* (2013.01)

(56) References Cited

U.S. PATENT DOCUMENTS

| | | | |
|---|---|---|---|
| 2,693,664 A | 11/1954 | Szuecs | |
| 2,693,665 A | 11/1954 | Humfeld et al. | |
| 2,761,246 A | 9/1956 | Szuecs | |
| 2,928,210 A | 3/1960 | Cirillo et al. | |
| 3,086,320 A | 4/1963 | Heinemann et al. | |
| 3,530,551 A | 9/1970 | Haes et al. | |
| 3,749,584 A | 7/1973 | Kurtzman et al. | |
| 3,810,997 A | 5/1974 | Chien | |
| 3,885,048 A | 5/1975 | Liggett et al. | |
| 3,912,825 A | 10/1975 | Spicer et al. | |
| 3,937,654 A | 2/1976 | Solomons et al. | |
| 3,969,189 A | 7/1976 | Kobayashi et al. | |
| 3,998,975 A | 12/1976 | Liepa et al. | |
| 4,056,638 A | 11/1977 | Huang et al. | |
| 4,061,781 A | 12/1977 | Solomons et al. | |
| 4,071,973 A | 2/1978 | Iizuka et al. | |
| 4,154,862 A | 5/1979 | Guadagni et al. | |
| 4,212,947 A | 7/1980 | Torev | |
| 4,265,915 A | 5/1981 | MacLennan et al. | |
| 4,367,240 A | 1/1983 | Maclennan et al. | |
| 4,555,485 A | 11/1985 | Marsh | |
| 4,590,160 A | 5/1986 | Nishihashi et al. | |
| 4,800,093 A | 1/1989 | Hogan et al. | |
| 4,891,220 A | 1/1990 | Donzis | |
| 4,938,972 A | 7/1990 | Moo-Young et al. | |
| 5,532,148 A | 7/1996 | Datta et al. | |
| 5,631,292 A | 5/1997 | Kurtz et al. | |
| 5,934,012 A | 8/1999 | Holtz et al. | |
| 6,045,834 A | 4/2000 | Howes et al. | |
| 6,254,901 B1 | 7/2001 | Ono | |
| 6,265,012 B1 | 7/2001 | Shamil | |
| 6,277,396 B1 | 8/2001 | Dente | |
| 6,383,799 B1 | 5/2002 | Wasser et al. | |
| 6,416,978 B1 | 7/2002 | Lee et al. | |
| 6,476,003 B1 | 11/2002 | Jordan et al. | |
| 6,490,824 B1 | 12/2002 | Intabon et al. | |
| 6,558,943 B1 | 5/2003 | Li et al. | |
| 6,569,475 B2 | 5/2003 | Song | |
| 7,045,160 B1 | 5/2006 | de Haan et al. | |
| 7,745,189 B2 | 6/2010 | Akin et al. | |
| 7,855,059 B2 | 12/2010 | Wenger et al. | |
| 7,939,671 B2 | 5/2011 | Li et al. | |
| 8,313,929 B2 | 11/2012 | Van Wezel et al. | |
| 8,343,741 B2 | 1/2013 | Liu et al. | |
| 8,481,295 B2 | 7/2013 | van Leeuwen et al. | |
| 8,672,245 B2 | 3/2014 | Finnigan et al. | |
| 9,068,171 B2 | 6/2015 | Kelly et al. | |
| 9,079,786 B2 | 7/2015 | Van Leeuwen et al. | |
| 9,289,003 B2 | 3/2016 | Kringelum et al. | |
| 9,301,539 B2 | 4/2016 | Appel et al. | |
| 9,526,267 B2 | 12/2016 | Anderson et al. | |
| 9,572,363 B2 | 2/2017 | Langan et al. | |
| 9,943,096 B2 | 4/2018 | Fraser et al. | |
| 10,010,103 B2 | 7/2018 | Soni et al. | |
| 10,154,627 B2 | 12/2018 | McIntyre et al. | |
| 10,370,636 B2 | 8/2019 | Van Hee | |
| 10,617,697 B2 | 4/2020 | Levanon et al. | |
| 10,661,320 B2 | 5/2020 | Huang et al. | |
| 10,829,420 B2 | 11/2020 | Ren et al. | |
| 11,032,982 B2 | 6/2021 | Ross et al. | |
| 11,058,137 B2 | 7/2021 | Pattillo | |
| 11,554,990 B2 | 1/2023 | Ren et al. | |
| 11,751,596 B2 | 9/2023 | Huggins et al. | |
| 2002/0082418 A1 | 6/2002 | Ikewaki | |
| 2002/0096473 A1 | 7/2002 | Ferro et al. | |
| 2002/0137155 A1 | 9/2002 | Wasser et al. | |
| 2002/0177576 A1 | 11/2002 | McGregor et al. | |
| 2003/0208796 A1 | 11/2003 | Song | |
| 2004/0009143 A1 | 1/2004 | Golz-Berner et al. | |
| 2004/0035047 A1 | 2/2004 | Hwang et al. | |
| 2004/0197461 A1 | 10/2004 | Finnigan et al. | |
| 2004/0211721 A1 | 10/2004 | Stamets | |
| 2005/0180989 A1 | 8/2005 | Matsunaga | |
| 2005/0255126 A1 | 11/2005 | Tsubaki et al. | |
| 2005/0273875 A1 | 12/2005 | Elias | |
| 2006/0014267 A1 | 1/2006 | Cleaver et al. | |
| 2006/0068056 A1 | 3/2006 | Sakamoto et al. | |
| 2006/0134294 A1 | 6/2006 | McKee | |
| 2006/0280753 A1 | 12/2006 | McNeary | |
| 2007/0160726 A1 | 7/2007 | Fujli | |
| 2008/0031892 A1 | 2/2008 | Kristiansen | |
| 2008/0038404 A1 | 2/2008 | Brunstedt et al. | |
| 2008/0057162 A1 | 3/2008 | Brucker et al. | |
| 2008/0107783 A1 | 5/2008 | Anijs et al. | |
| 2008/0171104 A1 | 7/2008 | Zhu et al. | |
| 2008/0193595 A1 | 8/2008 | De Vuyst et al. | |
| 2008/0226788 A1 | 9/2008 | Chang et al. | |
| 2008/0264858 A1 | 10/2008 | Stamets | |
| 2008/0274234 A1 | 11/2008 | Miller | |
| 2008/0295223 A1 | 12/2008 | Hiromoto | |
| 2008/0299645 A1 | 12/2008 | Holliday | |
| 2009/0047236 A1 | 2/2009 | Stamets | |
| 2009/0053363 A1 | 2/2009 | An | |
| 2009/0098244 A1 | 4/2009 | Schatzmayr et al. | |
| 2009/0104310 A1 | 4/2009 | Nakajima | |
| 2009/0130138 A1 | 5/2009 | Slamels | |
| 2009/0148558 A1 | 6/2009 | Kim et al. | |
| 2009/0220645 A1 | 9/2009 | Martinez | |
| 2009/0280212 A1 | 11/2009 | Sugimoto et al. | |
| 2010/0055241 A1 | 3/2010 | Nakano et al. | |
| 2010/0183765 A1 | 7/2010 | Laan Van Der et al. | |
| 2010/0203189 A1 | 8/2010 | Holliday | |
| 2010/0203194 A1 | 8/2010 | Salminen et al. | |
| 2010/0213293 A1 | 8/2010 | Finnigan et al. | |
| 2010/0221385 A1 | 9/2010 | Matsui et al. | |
| 2010/0227039 A1 | 9/2010 | Ungureanu et al. | |
| 2010/0239711 A1 | 9/2010 | Li | |
| 2010/0266726 A1 | 10/2010 | Ogura et al. | |
| 2010/0284944 A1 | 11/2010 | Ungureanu et al. | |
| 2010/0316763 A1 | 12/2010 | Choi et al. | |
| 2011/0008384 A1 | 1/2011 | Stamets | |
| 2011/0306107 A1 | 2/2011 | Kalisz et al. | |
| 2011/0052758 A1 | 3/2011 | Greiner-Stoeffele | |
| 2011/0070332 A1 | 3/2011 | Bemaert et al. | |
| 2011/0081448 A1 | 4/2011 | Dunphy et al. | |
| 2011/0086138 A1 | 4/2011 | Jia et al. | |
| 2011/0091579 A1 | 4/2011 | Hausman | |
| 2011/0123675 A1 | 5/2011 | Bemaert et al. | |
| 2011/0189220 A1 | 8/2011 | Yang | |
| 2011/0200551 A1 | 8/2011 | Stamets | |
| 2011/0206721 A1 | 8/2011 | Nair | |
| 2011/0229616 A1 | 9/2011 | Anijs et al. | |
| 2011/0262593 A1 | 10/2011 | Binggeli et al. | |
| 2011/0268980 A1 | 11/2011 | Kalisz et al. | |
| 2012/0027889 A1 | 2/2012 | Portella | |
| 2012/0034339 A1 | 2/2012 | Giuliani et al. | |

(56) References Cited

U.S. PATENT DOCUMENTS

| | | |
|---|---|---|
| 2012/0034344 A1 | 2/2012 | Menon et al. |
| 2012/0082754 A1 | 4/2012 | Holliday |
| 2012/0100249 A1 | 4/2012 | Laan et al. |
| 2012/0128823 A1 | 5/2012 | Camu et al. |
| 2012/0171308 A1 | 7/2012 | Da Luz Moreira et al. |
| 2012/0177781 A1 | 7/2012 | Hayashi |
| 2012/0180167 A1 | 7/2012 | Usami |
| 2012/0190093 A1 | 7/2012 | Fukuda |
| 2012/0231114 A1 | 9/2012 | Bezerra De Oliveira et al. |
| 2012/0244254 A1 | 9/2012 | Takahashi |
| 2012/0321744 A1 | 12/2012 | Chhun et al. |
| 2013/0078192 A1 | 3/2013 | Backes et al. |
| 2013/0142691 A1 | 6/2013 | Ozasa |
| 2013/0142820 A1 | 6/2013 | Fares et al. |
| 2013/0142903 A1 | 6/2013 | Duan et al. |
| 2013/0209608 A1 | 8/2013 | Berends et al. |
| 2013/0209609 A1 | 8/2013 | Moreno et al. |
| 2013/0216654 A1 | 8/2013 | Yu et al. |
| 2013/0337114 A1 | 12/2013 | Binggeli et al. |
| 2014/0065263 A1 | 3/2014 | Kelly et al. |
| 2014/0105928 A1 | 4/2014 | Stamets |
| 2014/0170264 A1 | 6/2014 | Kelly et al. |
| 2014/0302560 A1 | 10/2014 | Kelly |
| 2014/0342036 A1 | 11/2014 | Appel et al. |
| 2015/0140098 A1 | 5/2015 | Van Den Elshout et al. |
| 2015/0257405 A1 | 9/2015 | Kelly et al. |
| 2015/0257406 A1 | 9/2015 | Kelly et al. |
| 2015/0272155 A1 | 10/2015 | Kelly et al. |
| 2015/0296834 A1 | 10/2015 | Geistlinger |
| 2015/0342138 A1 | 12/2015 | Bayer et al. |
| 2016/0073671 A1 | 3/2016 | Geistlinger |
| 2016/0120201 A9 | 5/2016 | Kelly et al. |
| 2016/0249660 A1 | 9/2016 | Langan et al. |
| 2016/0312247 A1 | 10/2016 | Lennartsson et al. |
| 2017/0295837 A1 | 10/2017 | Soni et al. |
| 2018/0014567 A1 | 1/2018 | Finnigan et al. |
| 2018/0064148 A1 | 3/2018 | Langan et al. |
| 2018/0303044 A1 | 10/2018 | Soni et al. |
| 2019/0059431 A1 | 2/2019 | Kozubal et al. |
| 2019/0069575 A1 | 3/2019 | Shigeta et al. |
| 2019/0307157 A1 | 10/2019 | Kozubal et al. |
| 2019/0373934 A1 | 12/2019 | Huggins et al. |
| 2019/0373935 A1 | 12/2019 | Huggins et al. |
| 2020/0024577 A1 | 1/2020 | Carlton et al. |
| 2020/0093155 A1 | 3/2020 | Pattillo |
| 2020/0093167 A1 | 3/2020 | Pattillo |
| 2020/0268031 A1 | 8/2020 | Macur et al. |
| 2021/0024428 A1 | 1/2021 | Ren et al. |
| 2021/0059287 A1 | 3/2021 | Kozubal et al. |
| 2021/0127601 A9 | 5/2021 | Kaplan-Bie et al. |
| 2021/0171896 A1 | 6/2021 | Harney et al. |
| 2021/0337827 A1 | 11/2021 | Whiteley et al. |
| 2022/0000159 A1 | 1/2022 | Pattillo |
| 2022/0000162 A1 | 1/2022 | Hüttner |
| 2022/0117276 A1 | 4/2022 | Pattillo |
| 2022/0117282 A1 | 4/2022 | Pattillo |
| 2022/0225653 A1 | 7/2022 | Soni et al. |
| 2022/0322617 A1 | 10/2022 | Soni et al. |
| 2023/0180807 A1 | 6/2023 | Huggins et al. |
| 2023/0180808 A1 | 6/2023 | Huggins et al. |
| 2023/0371569 A1 | 11/2023 | Huggins et al. |
| 2024/0099348 A1 | 3/2024 | Huggins et al. |

FOREIGN PATENT DOCUMENTS

| | | |
|---|---|---|
| CN | 101899399 A | 12/2010 |
| CN | 101579103 B | 8/2012 |
| CN | 102860541 A | 1/2013 |
| CN | 103229888 A | 8/2013 |
| CN | 103987271 A | 8/2014 |
| CN | 107072245 A | 8/2017 |
| CN | 107072246 A | 8/2017 |
| CN | 108026559 A | 5/2018 |
| CN | 110106090 A | 8/2019 |
| DE | 4341316 A1 | 6/1995 |
| DK | 3292769 T3 | 7/2019 |
| EP | 0986960 A1 | 3/2000 |
| EP | 2835058 A1 | 2/2015 |
| EP | 3131406 | 2/2017 |
| EP | 3292769 B1 | 4/2019 |
| GB | 1537173 A | 12/1976 |
| GB | 2059243 A | 4/1981 |
| GB | 2137226 A | 10/1984 |
| GB | 2120534 B | 1/1986 |
| JP | S59135840 A | 8/1984 |
| JP | S61219340 A | 9/1986 |
| JP | S6291161 A | 4/1987 |
| JP | H10179089 | 7/1998 |
| JP | H 11346657 A | 12/1999 |
| JP | 2000316512 A | 11/2000 |
| JP | 2003333998 A | 11/2003 |
| JP | 2005-0027540 A | 2/2005 |
| JP | 4126037 B2 | 7/2008 |
| KR | 100762848 B1 | 10/2007 |
| KR | 1020190139187 | 12/2019 |
| KR | 1020190162768 | 12/2019 |
| RU | 2 562 146 C2 | 10/2012 |
| WO | 2020/061502 A1 | 3/2010 |
| WO | 2017/068012 A1 | 4/2017 |
| WO | WO 2017/151684 A1 | 9/2017 |
| WO | 2017/208255 A1 | 12/2017 |
| WO | 2018/075112 A1 | 4/2018 |
| WO | WO 2019/121697 A1 | 6/2019 |
| WO | WO 2019/237059 A1 | 12/2019 |
| WO | 2020/074782 A1 | 4/2020 |
| WO | WO 2020/106743 A1 | 5/2020 |
| WO | WO 2021/163215 A1 | 8/2021 |
| WO | WO 2021/163216 A1 | 8/2021 |

OTHER PUBLICATIONS

Hung, Yung-Tse, Howard H. Lo, Adel Awad, and Hana Salman. "Potato wastewater treatment." In Handbook of Industrial and Hazardous Wastes Treatment, pp. 894-951. CRC Press, 2004.

"The Original Mycoprotein." Downloaded on May 11, 2022 from eniferbio.fi/the-original-mycoprotein/. Article dated Feb. 8, 2022, 13 pages.

EniferBio. "eniferBio teams up with Tereos to provide sustainable PEKILO® protein for Skretting's feeding trials", YouTube, May 4, 2021 (video online). [Retrieved from the internet on May 11, 2022, <https://youtu.be/7RVNdUZkglw>].

EniferBio. "The world's first mycoprotein plant—The Pekilo® plant in Jamsankoski, Finland", YouTube, Apr. 10, 2022 (vdieo online). [Retrieved from the internet on May 11, 2022, <https://youtu.be/hkwWNxKa14Q>].

EniferBio. "The PEKILO® Process", YouTube, Mar. 8, 2022 (video online). [Retrieved from the internet on May 11, 2022, <https://youtu.be/OrU8lhlZHuU>].

U.S. Appl. No. 17/739,725, filed May 9, 2022.

Non-Final Office Action and pending claims, U.S. Appl. No. 17/561,312, mailed Apr. 29, 2022, 14 pages.

Non-Final Office Action and pending claims, U.S. Appl. No. 17/561,322 mailed Mar. 28, 2022, 14 pages.

Gmoser et al., "Pigment Production by the Edible Filamentous Fungus Neurospora Intermedia" 4(11):1-15 (Feb. 2018).

Kim et al., "Bioproduction of mushroom mycelium of Agaricus bisporus by commercial submerged fermentation for the production of meat analogue," J. Sci. Food Agric., vol. 91(9), pp. 1561-1568 (2011).

U.S. Appl. No. 18/364,750, filed Aug. 3, 2023.

U.S. Appl. No. 18/496,682.

Pu et al., "Preparation and Application of a Novel Bioflocculant by Two Strains of *Rhizopus* sp. Using Potato Starch Wastewater as Nutrilite", Bioresource Technology, Jun. 2014, vol. 162, pp. 184-191.

Krull, R., et al., "Characterization and Control of Fungal Morphology for Improved Production Performance in Biotechnology", J. Biotechnol., Jan. 20, 2013, vol. 163(2), pp. 112-123, (Abstract only).

(56) References Cited

OTHER PUBLICATIONS

International Search Report and Written Opinion, Application No. PCT/US2022/028320, mailed Sep. 21, 2022, 14 pages.
Espin, G. et al., "Effect of the Deprivation of Amino Acids on Conidia of Neurospora crassa," Journal of General Microbiology, vol. 104, pp. 233-240 (1978).
Krull, R. et al., "Filaments in Bioprocesses," Advances in Biochemical Engineering/Biotechnology, vol. 149, 317 pages (2015).
Knight, N. et al., "The thermal stability of Quorn (TM) pieces," International Journal of Food Science and Technology, vol. 36, pp. 47-52 (2001).
Wucherpfennig, T. et al., "Chapter 4. Morphology and Rheology in Filamentous Cultivations," Advances in Applied Microbiology, vol. 72, pp. 89-136 (2010).
Wei, Y., "Study on the effects of Neurospora robusta fermentation on the nutritional components of bean dregs and the isolation and purification of polysaccharides," Masters Thesis, Zhangqiao Research, 3 pages (2007). (Abstract).
Huggins, M.T., "Synthesis of Biomass Derived Carbon Materials for Environmental Engineering and Energy Storage Applications," Ph.D.Thesis to the University of Colorado, Department of Civil, Environmental, and Architectural Engineering, 159 pages (2016).
Souza Filho, P.F. et al., "Vegan-mycoprotein concentrate from pea-processing industry byproduct using edible filamentous fungi," Fungal Biology and Biotechnology, vol. 5, No. 5, 10 pages (2018).
Cairns, et al., "Moulding the mould: understanding and reprogramming filamentous fungal growth and morphogenesis for next generation cell factories," Biotechnology for Biofuels, vol. 12, 77, 18 pages (2019).
Foster, "Here's How (and Why) to Slice Meat Against the Grain," Kitchn, retrieved Aug. 19, 2021 from https://www.thekitchn.com/heres-exactly-how-to-slice-meat-against-the-grain-and-why-you-should-be-doing-it-meat-basics-215798, 5 pages (2015).
Markham, et al., "Choline: Its role in the growth of filamentous fungi and the regulation of mycelial morphology," FEMS Microbiology Reviews, vol. 10(3-4), pp. 287-300 (1993).
Veiter, et al., "The filamentous fungal pellet-relationship between morphology and productivity," Applied Microbiology and Biotechnology, vol. 102, pp. 2997-3006 (2018).
Walisko, et al., "The Taming of the Shrew-Controlling the Morphology of Filamentous Eukaryotic and Prokaryotic Microorganisms," Adv. Biochem. Eng. Biotechnol., pp. 1-27 (2015).
Wiebe, et al., "Effect of Choline on the Morphology, Growth and Phospholipid Composition of Fusarium graminearum," Journal of General Microbiology, vol. 135(8), pp. 2155-2162 (1989).
Bobby B., "How to Cut Salmon Sashimi and Nigiri," Blade Advisor, retrieved Aug. 19, 2021 from https://bladeadvisor.com/how-to-cut-salmon-sashimi-and-nigiri/, 10 pages (2019).
Wikipedia, "Mycelium", retrieved Aug. 19, 2021 from <https://en.wikipedia.org/w/index.php?title=Mycelium&oldid=761708709>, Jan. 24, 2017, 3 pages.
Wikipedia, "Protein Digestibility Corrected Amino Acid Score", retrieved Aug. 19, 2021 from <https://en.wikipedia.org/w/index.php?title=Protein_Digestibility_Corrected_Amino_Acid%20Score&oldid+809488538>, Nov. 9, 2017, 4 pages.
Moo-Young, M. et al., "Fermentation of Cellulosic Materials to Mycoprotein Foods," Biotech. Adv., vol. 11, pp. 469-479 (1993).
Ferreira, J. A. et al., "Production of ethanol and biomass from thin stillage by Neurospora intermedia: A pilot study for process diversification," Eng. Life Sci., vol. 15, pp. 751-759 (2015).
Jiang et al., "UV Induced Conversion During Drying of Ergosterol to Vitamin D in Various Mushrooms: Effect of Different Drying Conditions," Trends in Food Science & Technology, pp. 200-210 (2020).
Wu et al., "Statistical Optimization of Ultraviolet Irradiate Conditions for Vitamin D2 Synthesis in Oyster Mushrooms (*Pleurotus ostreatus*) Using Response Surface Methodology," PLoS ONE, 9(4): e95359; pp. 1-7 (2014).
Pape et al., "FDA GRAS Notice GRN No. 91"; Nov. 2001:74 pages.

Kumitch, HM, et al., "Effect of fermentation time on the physicochemical and functional properties of pea protein-enriched flour fermented by Aspergillus oryzae and Aspergillus niger,"Cereal Chem.; 97: 416-428 (2020). https://doi.org/10.1002/cche.10257.
Souza Filho, "Fungi-based biorefinery model for food industry waste: progress toward a circular economy," University of Boras, pp. 1-88 (2018). ORCID iD: 0000-0002-1711-7294.
Zahler, J., "Improving the Nutritional Characteristics of Plant Feedstuff ByProducts Using Fungal Metabolism," Electronic Theses and Dissertations. 2689; pp. 1-134 (2018). https://openprairie.sdstate.edu/etd/2689.
Wei, Y., "Study on the effects of Neurospora robusta fermentation on the nutritional components of bean dregs and the isolation and purification of polysaccharides", Zhangqiao Research, Nanchang University, vol. 214, pp. 1 (2007). (English Abstract).
Lin, B.-S et al., "Isolation, identification, genome variation and functional analysis of a strain form Neurospora crassa", Microbiology China, vol. 47(3), p. 771-781 (2020).
Yassin, M.S.B.M., "The physiological and ecological characteristics of the red bread mould", Ph.D. Thesis, University of Bath, ProQuest, pp. 1-201 (1980).
Rizal, Y. et al. "Comparisons of nutrient contents and nutritional values of palm kernel cake fermented by using different fungi", Pakistan Journal of Nutrition, vol. 12(10), pp. 943-948 (2013).
Zahler, J., "Improving the Nutritional Characteristics of Plant Feedstuff By-Products Using Fungal Metabolism", Electronic Theses and Dissertations. 2689, South Dakota State University, pp. 1-146 (2018).
Zapata, A. et al., "Testing the potential of using the fungus Neurospora crassa to convert human waste into edible protein", Valparaiso University, ValpoScholar, pp. 1-2 (2011). (English Abstract).
Jun, Y. et al., "Study on the Change of Nutrition Components in Neurospora. Crassa Fermentation Process of Soybean Residue", Journal of Chinese Institute of Food Science and Technology, vol. 13(12), pp. 1-5 (2013). (English Abstract).
Yang Feng-ling et al., "Progress in the Production of Carotenoids from Neurospora crassa", Food and Fermentation Industries, State Key Laboratory of Food Science and Technology , Nanchang University, vol. 38(11), p. 115-119 (2012). (Engllish Abstract).
"Indonesian Soybean Product 4: Oncom", Foodiepelago Your Resource of Indonesian Food, https://foodiepelago.wordpress.com/2013/09/28/indonesian-soybean-product-4-oncom/, pp. 1-5 (2013).
Macris, B.J. et al., "Solid State Fermentation of Straw with Neurospora Crassa for CMCase and Beta-Glucosidase Production", Biotechnology Letters, vol. 9(9), pp. 661-664 (1987).
Dwidjoseputro, D., "Studies on Monilia sitophila from Indonesia", bulletin of the Torrey Botanical Club , vol. 88(6), pp. 404-411 (Nov.-Dec. 1961).
Bartholomai, B. M. et al., "Safety evaluation of Neurospora crassa mycoprotein for use as a novel meat alternative and enhancer", Food and Chemical Toxicology, vol. 168, pp. 113342, 1-14, (2022).
Neurospora crassa Shear et Dodge 24914, https://www.atcc.org/products/24914, Product citation, pp. 1-4 (downloaded Feb. 29, 2024).
Tamang, J. P., et al., "Review: Diversity of Microorganisms in Global Fermented Food and Beverages", Frontiers in Microbiology, Article 377, pp. 1-28 (2016).
Tamang, J. P. et al., "Chapter 1: Microorganisms in Fermented Foods and Beverages", pp. 1-110 (2015).
Hui, Y. H. et al., "Handbook of Plant-Based Fermented Food and Beverage Technology", Second Edition, 319 pages (2012).
Surono, I. S., "Ethnic Fermented Food and Beverages of Indonesia", Ethnic Fermented Foods and Alcoholic Beverages of Asia, pp. 341-382 (2016).
Steinkraus, K., "Handbook of Indigenous Fermented Foods", Second Edition, pp. 1-110 (1996).
Santoso, U. et al., "Effect of Fermented Sauropus androgynus Leaves on Meat Composition, Amino Acid and Fatty Acid Compositions in Broiler Chickens", Pakistan Journal of Nutrition, vol. 14(11), pp. 799-807 (2015).
Qiu, Y. et al., "Analysis of key fungi and their effect on the edible quality of HongJun tofu, a Chinese fermented okara food", LWT—Food Science and Technology, vol. 172, pp. 1-12, 114151 (20.

(56) References Cited

OTHER PUBLICATIONS

Gmoser, R., "Circular bioeconomy through valorisation of Agro-industrial residues by the edible filamentous fungus Neurospora intermedia", University of Boras, pp. 1-212 (2021).

Qiu, Y., "Fermentation with a Multi-Strain to Enhance the Flavor of Hongjun Tofu, a Chinese Fermented Okara Food", LWT—Food Science and Technology, vol. 189, pp. 1-12 (2023).

"Oncom, Encyclopedia, Science News & Research Reviews", pp. 1-9.

Surya, R. et al., "Antioxidant profile of red oncom, an Indonesian traditional fermented soyfood", Food Research, vol. 7(4), pp. 204-210 (2023).

Yao, H. et al., "Differential analysis and bioactivity identification of Neurospora crassa metabolites based on okara by widely-targeted metabolomics", LWT—Food Science and Technology, vol. 174, pp. 1-8, 114441 (2023).

Nuraini, N., "Improving the Quality of Tapioca by Product Through Fermentation by Neurospora crassa to Produce β Carotene Rich Feed", Pakistan Journal of Nutrition, vol. 8(4), pp. 487-490 (2009).

"Notice on approving and publishing the second batch of municipal intangible cultural heritage list of Meizhou City", Office of Meizhou Municipal People's Government, Mei City Government No. 19, pp. 1-3 (2009).

Lubick, N., "Multitalented Mold Sequenced Neurospora crassa's DNA may yield a broad range of insights", Biology, https://www.science.org/content/article/multitalented-mold-sequenced, pp. 1-2 (2003).

Burton, E. G. et al., "Regulation of methionine biosynthesis in Neurospora crassa", Archives of Biochemistry and Biophysics, vol. 168(1), pp. 219-229 (1975). (Abstract).

Sanders, D. et al., "Control of Intracellular pH. Predominant Role of Oxidative Metabolism, Not Proton Transport, in the Eukaryotic Microorganism Neurospora", J. Gen. Physiol., vol. 80, pp. 377-402 (1982).

Wiebers, J. L. et al. "Interrelationships of Sulfur Amino Acids in the Pool and Cellular Protein of Neurospora crassa.", Biochmica et Biophysica Acta., vol. 117(2), pp. 403-409 (1966). (Abstract).

Finnigan, T. et al., "Chapter 19—Mycoprotein: A Healthy New Protein with a Low Environmental Impact.", Sustainable Protein Sources., pp. 305-325 (2017). (Abstract).

Miller, SA et al., Evaluating the Safety and Nutritional Value of Mycoprotein.:, Food Technology, vol. 55(7), pp. 42-47 (2001). (Abstract).

Asgar et al.: "Nonmeat Protein Alternatives as Meat Extenders and Meat Analogs", Comprehensive Reviews in Food Science and Food Safety, vol. 9, No. 5, Sep. 1, 2010 (Sep. 1, 2010), pp. 513-529, XP55005273, ISSN: 1541-4337, DOI: 10.1111/j.1541-4337.2010.00124.x.

Bátori et al., "Ethanol and Protein from Ethanol Plant By-Products Using Edible Fungi Neurospora intermedia and Aspergillus oryzae", Hindawi Publishing Corporation, BioMed Research International, vol. 2015, Article ID 176371, 10 pages.

Berovic et al. (2003) "Submerged cultivation of Ganoderma lucidum biomass and immunostimulatory effects of fungal polysaccharides" J. Biotechnol. 103(1): 77-86.

Beuchat "Indigenous Fermented Foods", in Biotechnology Set, Second Edition (eds H.-J. Rehm and G. Reed), Wiley-VCH Verlag GmbH, Weinheim, Germany, p. 505-559, 2001.

Bok et al. Phytochemistry (1999) "Antitumor sterols from the mycelia of Cordyceps sinensis" 51: 891-898.

Canedo et al., "Protein enrichment of brewery spent grain from Rhizopus oligosporus by solid-state fermentation", Bioprocess Biosyst Eng (2016) 39:1105-1113.

Chang et al. (2002), "Bioactive Polysaccharides from Traditional Chinese Medicine Herbs as Anticancer Adjuvants", The Journal of Alternative and Complementary Medicine, V. 8 (5): 559-565.

Chang et al. (2009) "Gandoderma lucidum Extract Promotes Immune Responses in Normal BALB/c Mice In Vivo", in vivo, V. 23: 755-760.

ClearTaste™ White Paper, Jan. 2016, MycoTechnology, Sustainable Neutral Taste & Aroma Non-Animal Protein, PureTaste Shiitake Protein, 5 pages.

Crafack et al., "Influencing cocoa flavour using Pichia Kluyveri and Kluyveromyces marxianus in a defined mixed starter culture for cocoa fermentation", International Journal of Food Microbiology 167: 103-116 (2013).

Moore et al., 21st Century Guidebook to Fungi by David Moore, Geoffrey D. Robson and Anthony P.J. Trinci; 17.18 The Quorn fermentation and evolution in fermenters; Updated Dec. 17, 2016, Built by David Moore with Course Genie and Dreamweaver; 8 pages.

De Melo, Rodrigues et al. (2008) Influence of Flammulina velutipes mycelia culture conditions on antimicrobial metabolite production Mycoscience 50(1): 78-8.

Denny et al.: "REVIEW Mycoprotein and health", British Nutrition Foundation Nutrition Bulletin, Jan. 1, 2008 (Jan. 1, 2008), pp. 298-310, XP55401905, Retrieved from the Internet: URL:http://onlinelibrary.wiley.com/store/10.1111/j.1467-3010.2008.00730.x/asset/j.1467-3010.2008.00730.x.pdf?v=1&t=j6xdi27x&s=4c80492be8685ba3ba396b891bf64d0a5cb2b3fd.

Dhingra et al., "Utilization of Potato Processing Waste for Compound Cattle Feed", Agricultural Engineering Today, vol. 37(4), 2013.

Diekman, "Sweeterners Facts and Fallacies: Learn the Truth about the Different Types of Sweeterners to Better Counsel Patients", Today's Dietitian 14(9): pp. 42-45, Sep. 2012.

EMDEN (2015) "Decaffeination 101: Four Ways to Decaffeinate Coffee" Coffee Connection; retrieved from: http://www.coffeeconfidential.org/health/decaffeination/ Jan. 29, 2015. 7 pages.

Encyclopedia Britannica, Louis Pasteur, Datasheet [online]. Copyright 2014 Encyclopedia Britannica Inc. [retrieved on Feb. 6, 2014]. Retrieved from the Internet: <URL: http://www.britannica.com/Ebchecked/topic/445964/Louis-Pasteur>. Specif, p. 3.

Finnigan et al., "Mycoprotein: A Healthy New Protein With a Low Environmental Impact", Chapter 19, Sustainable Protein Sources. DOI: http://dx.doi.org/10.1016/B978-0-12-802778-3.00019-6 ; 21 pages.

Firenzuoli et al. (2008) "The Medicinal Mushroom Agaricus blazei Murrill: Review of Literature and Pharmaco-Toxicological Problems" Evid. Based Complement Alternat. Med. 5(1): 3-15.

Han (2005) Solid-state fermentation of cornmeal with the basidiomycete Ganoderma lucidum for degrading starch and upgrading nutritional value J. Appl. Micro. 2005, 99: 910-915.

Hashim, Puziah (1997) "Effect of Processing on Flavour Precursors, Pyrazines and Flavour Quality of Malaysian Cocoa Beans". PhD thesis, Universiti Pertanian Malaysia.

He, Jianwei et al. (2010) "Patented Techniques for Detoxification of Mycotoxins in Feeds and Food Matrices" Recent Patents on Food, Nutrition & Agriculture, vol. 2:96104.

Hultberg et al., "Fungi-based treatment of brewery wastewater—biomass production and nutrient reduction", Appl Microbiol Biotechnol (2017) 101:4791-4798.

Ikrawan, Yusep (2003) Influence of Carboxypeptidases on Cocoa Specific Aroma Precursors and Methylpyrazines in Under-Fermented Cocoa Beans. PhD thesis, Universiti Putra Malaysia.

International Search Report and Written Opinion for PCT Application PCT/US2019/052236 dated Dec. 4, 2019, 18 pages.

International Preliminary Report on Patentability dated Search Report and Written Opinion for PCT Application PCT/US2018/025301 dated Sep. 2, 2018, 5 pages.

International Search Report and Written Opinion for PCT Application PCT/US2018/025301 dated Sep. 2, 2018, 9 pages.

Ishikawa et al. (2001) "Antimicrobial Cuparene-Type Sesquiterpenes, Enokipodins C and D, from a Mycelial Culture of Flammulina velutipes" J. Nat. Prod, 64(7): 932-934.

Jin et al., "A comprehensive pilot plant system for fungal biomass protein production and wastewater reclamation", Advances in Environmental Research, 2002, vol. 6, pp. 179-189.

Jin, B. et al. "Utilisation of Starch Processing Wastewater for Production of Microbial Biomass Protein and Fungal αAmylase by *Aspergillus oryzae*", Bioresource Technology, 66:201-206 (1998). (OA.00004 Matter).

(56) References Cited

OTHER PUBLICATIONS

Kamimuira, Hisashi (1989) "Removal of Mycotoxins during Food Processing" Tokyo Metropolitan Research Laboratory of Public Health article: 88-94.
Kang (2003) Abstract of "Studies on chemical constituents of the mycelia from fermented culture of Flammulina velutipes" Zhongguo Zhong Yao Za Zhi 28(11): 1038-1040.
Kang (2005) Abstract of "Studies on chemical constituents in the mycelia from fermented culture of Flammulina velutipes" Zhongguo Zhong Yao Za Zhi 30(30): 193-195.
Konno et al. (2002) "Anticancer and Hypoglycemic Effects of Polysaccharides in edible and Medicinal Maitake Mushroom [Grifola frondosa(Dicks.: Fr.) S. F. Gray]" International Journal of Medicinal Mushrooms 4(3): 10-21.
Kühnel et al., "Aiming for the complete utilization of sugar-beet pulp: Examination of the effects of mild acid and hydrothermal pretreatment followed by enzymatic digestion", Biotechnology for Biofuels 2011, 4:14.
Kuo et al. (1996) "Cordyceps sinensis as an Immunomodulatory Agent" Am. J. Chin. Med. (1996) 24: 111-125.
Lakshmi et al. (2003) Abstract of "Antiperoxidative, antiinflammatory, and antimutagenic activities of ethanol extract of the mycelium of Ganoderma lucidum occurring in South India" Teratog. Carcinog. Mutagen 1: 85-97.
Lee et al. (2003) "Biological activities of the polysaccharides produced from submerged culture of the edible Basidiomycete Grifola frondosa" Enzyme and Microbial Technology 32(5): 574-581.
Lefeber et al., "On-farm implementation of a starter culture for improved cocoa bean fermentation and its influence on the flavour of chocolates produced thereof", Food Microbiology 30:379-392 (2012).
Liu et al. (2012) Molecules, 17:12575-12586, Improving the Fermentation Production of the Individual Key Triterpene Ganoderic Acid Me by the Medicinal Fungus Ganoderma lucidum in Submerged Culture.
MicrobiologyBytes. Introduction to Mycology. Datasheet [online'. Updated Apr. 8, 2009 [retrieved on Feb. 6, 2014]. Retrieved from the Internet: <URL: http://www.microbiologybytes.com/introduction/myc1.html>. Specif, p. 8.
Miri et al. "Flow induced fibre alignment in Mycoprotein paste",Food Research International, Elsevier, Amsterdam, NL, vol. 38, No. 10, Dec. 1, 2005 (Dec. 1, 2005), pp. 1151-1160, XP027868270, ISSN: 0963-9969 [retrieved on Dec. 1, 2005].
Mitra et al.: "Value-added oil and animal feed production from corn-ethanol stillage using the oleaginous fungus Mucor circinelloides", Bioresource Technology, Elsevier, Amsterdam,NL, vol. 107, Mar. 1, 2012 (Mar. 1, 2012), pp. 368-375, XP002696572, ISSN: 0960-8524, DOI: 10.1016/J.BIORTECH.2011.12.031 [retrieved on Dec. 14, 2011].
Ali, Mohamed, Aisha Bibi (2010) Production of pyrazine flavours by mycelial fungi. Master's thesis, University of Pretoria.
Moo-Young et al.: "Fermentation of cellulosic materials to mycoprotein foods", Biotechnology Advances, Elsevier Publishing, Barking, GB, vol. 11, No. 3, Jan. 1, 1993 (Jan. 1, 1993). pp. 469-479 XP025222949, ISSN: 0734-9750, DOI: 10.1016/0734-9750(93)90015-F [retrieved on Jan. 1, 1993.
Morris et al. (2003) Abstract of "Immunomodulating Effects of Hot-Water Extract From *Pleurotus ostreatus* Mycelium on Cyclophosphamide Treated Mice" Micologia Aplicada Internacional 15(1): 7-13.
Nair et al. "Mycelial Pellet Formation by Edible Ascomycete Filamentous Fungi, *Neprospora intermdela*", AMB Express. 6:31, 10 pages (2016) (.00004 Office Action).
Nitayavardhana et al., "Production of protein-rich fungal biomass in an airlift bioreactor using vinasse as substrate", Bioresource Technology, vol. 133 (2013) 301-306.
Nowrousian et al. "The novel ER membrane protein PRO41 is essential for sexual development in the filamentous fungus Sordaria macrospora" Molecular microbiology 64(4): 923-937, 200.

Ogundero, "Thermophilic fungi and fermenting cocao beans in Nigeria", Mycopalhologia 82, 159-165 (1983).
Pandy et al. (2000) "Use of Various Coffee Industry Residues for the Cultivation of Pleurotus streatus in Solid Stale Fermentation", Acta Biotechnol, V 20(1):41-52.
Paterson (2006) "Ganoderma—A therapeutic fungal biofactory" Phytochemistry 67:1985-2001.
Rasmussen et al., "Water reclamation and value-added animal feed from corn-ethanol stillage by fungal processing", Bioresource Technology 151 (2014) 284-290.
Rodger: "Production and Properties of Mycoprotein as a Meat Alternative". Food Technology, Institute of Food Technologists, Chicago, IL, US, vol. 55,No. 7, Jul. 1, 2001 (Jul. 1, 2001), p. 36, XP001101831, ISSN: 0015-6639.
Russell, R. et al. 2006. Ganoderma—a therapeutic fungal biofactory. Phytochemistry 67:1985-2001. specif, pp. 1985, 1987-1988, 1994-1995, 1997-1998.
Samir Kumar Khanal, Utilization of Local Agri-processing By-products to Produce Fungal Protein for Aquatic Feed Production, Local Feed Workshop, Oceanic Institute of Hawaii Pacific University, Nov. 21, 2014, Honolulu 26 pages.
Sankaran et al., "Use of Filamentous Fungi for Wastewater Treatment and Production of High Value Fungal Byproducts: A Review", Critical Reviews in Environmental Science and Technology, 40:400-449, 2010.
Saoharit Nitayavardhana et al.: "Production of protein-rich fungal biomass in an airlift bioreactor using vinasse as substrate", Bioresource Technology, vol. 133, Jan. 30, 2013 (Jan. 30, 2013), pp. 301-306, XP55645529, Amsterdam, NL ISSN: 0960-8524, DOI: 10.1016/j.biortech.2013.01.073.
Schtigerl et al., "Investigation of the use of agricultural byproducts for fungal protein production", Process Biochemistly, vol. 32, No. 8, pp. 705-714, 1997.
Schwan, "Cocoa Fermentations Conducted with a Defined Microbial Cocktail Inoculum", Applied and Environmental Microbiology, vol. 64, No. 4, Apr. 1998.
Schwan, "The Microbiology of Cocoa Fermentation and its Role in Chocolate Quality", Critical Reviews in Food Science and Nutrition, 44:205-221 (2004).
Shao et al. (2001) "Determination of nucleosides in natural Cordyceps sinensis and cultured Cordyceps mycelia by capillary electrophoresis" Electrophoresis 22(1): 144150.
Sone et al. (1985) "Structures and Antitumor Activities of the Polysaccharides Isolated from Fruiting Body and the Growing Culture of Mycelium of Ganoderma lucidum", Agric. Biol. Chem., V. 49(9): 2641-2653.
Souza et al.: "Edible Protein Production by Filamentous Fungi using Starch Plant Waslewater", Waste and Biomass Valorization, Springer Netherlands, NL, vol. 10, No. 9, Mar. 7, 2018 (Mar. 7, 2018), pp. 2487-2496, XP036859959, ISSN:1877-2641,DOI: 10.1007/S12649-018-0265-2 [retrieved on Mar. 7, 2018].
Souza Filho et al., "Production of Edible Fungi from Potato Protein Liquor (PPL) in Airlift Bioreactor", Fermentation 2017, 3, 12; doi:10.3390/fermentation3010012; 12 pages.
Sparringa et al.: "Glucosamine content of tempe mould, Rhizopus oligosporus", International Journal of Food Microbiology, vol. 47, No. 1-2, Mar. 1, 1999 (Mar. 1, 1999), pp. 153-157, XP55645542,NL ISSN: 0168-1605, DOI: 10.1016/S0168-1605(99)00020-3.
Stamets (2003) Chapter 12, pp. 89-92 Culturing Mushroom Mycelium on Agar Media.
Stevens et al., "Production of Microbial Biomass Protein from Potato Processing Wastes by Cephalosporium eichhorniae", Applied and Environmental Microbiology, vol. 53, No. 2, Feb. 1987, pp. 284-291.
Tang et al., "Current progress on truffle submerged fermentation: a promising alternative to its fruiting bodies", Appl Microbiol Biotechnol (2015) 99:2041-2053.
Taylor, J. (2001) "Measuring Fungal Growth." Chapter 3,8 In: Microorganisms and Biotechnology, 2nd ed., Thomas Nelson, Ltd. 2001 Delta Place, Chellenham, U. K. (ISBN 0 17 448255 8). Specif. p. 4 (book p. 44).

(56) References Cited

OTHER PUBLICATIONS

Trinci: "'Quom' mycoprotein", MYCOLOGIST, vol. 5, No. 3, Jul. 1, 1991 (Jul. 1, 1991), pp. 106-109, XP55638561,GB ISSN: 0269-915X, DOI:10.1016/S0269-915X(09)80296-6.

Tsubouchi et al. (1987) "Effect of roasting on ochratoxin A level in green coffee beans inoculated with Aspergillus ochraceus", Mycopathologia 97: 111-115.

Ulziijargal et al. (2011) : Nutrient Compositions of Culinary-Medicinal Mushroom Fruiting Bodies and Mycelia Int. J. Med. Mushrooms 13(4): 343-349.

Van Leeuwen et al., "Fungal Treatment of Crop Processing Wastewaters with Value-Added Co-Products", Green Energy and Technology, DOI: 10.1007/978-1-4471-2324-8_2, Springer-Verlag London Limited 2012. 33 pages.

Wasser (2002) "Medicinal mushrooms as a source of antitumor and immunomodulating polysaccharides" Appl Microbiol Biotechnol 60: 258-274.

Willis, W.L. et al. (2010) Effect of Dietary Fungus Myceliated Grain on Broiler Performance and Enteric Colonization with Bifidobacteria and *Salmonella International Journal of Poultry Science.*, 9(1): 48-52.

Wu et al. (2011) "Ling Zhi-8 mediates p53-dependent growth arrest of lung cancer cells proliferation via the ribosomal protein S7-MDM2-p53 pathway" Carcinogenesis 32(12): 1890-1896.

Xiros et al., "Hydrolysis and fermentation of brewer's spent grain by Neurospora crassa", Bioresource Technology 99 (2008) 5427-5435.

Yin et al. (2010) "Purification, Characterization and Immuno-Modulating Properties of Polysaccharides isolated from *Flammulina velutipes Mycelium*" Am. J. Chin. Med. 38(1): 191-204.

Zhang et al. (2004) Life Sciences, 75:2911-2919, Induction of HL-60 apoptosis by ethyl acetate of Cordyceps sinensis fungal mycelium.

Zhang et al. (2010) "Mycelial growth and polysaccharide content of *Polyporus umbellatus*" Journal of Medicinal Plants Research 4(18): 1847-1852.

Zhong et al. (2004) "Submerged Cultivation of Medicinal Mushrooms for Production of Valuable Bioactive Metabolites", Adv Biochem Engin/Biotechnol V. 87: 25-59.

Zhou et al. (2009) "Cordyceps fungi: natural products, pharmacological functions and developmental products" Journal of Pharmacy and Pharmacology 61:279-291.

Sastraatmadja, D. D. et al "Production of High-Quality Oncom, a Traditional Indonesian Fermented Food, by the Inoculation with Selected Mold Strains in the Form of Pure Culture and Solid Inoculum," J. Grad. Sch. Agr. Hokkaido Univ., vol. 70, Pt. 2: pp. 111-127 (2002).

Ho, C.C. "Identity and Characteristics of Neurospora intermedia Responsible for Oncom Fermentation in Indonesia", Food Microbiology, vol. 3, pp. 115-132 (1986).

Huggins, T. M. et al., "Controlled Growth of Nanostructured Biotemplates with Cobalt and Nitrogen Codoping as a Binderless Lithium-Ion Battery Anode", ACS Applied Materials & Interfaces, vol. 8, pp. 26868-26877 (2016).

Dekkers, B. L. et al. "Structuring Processes for Meat Analogues," Trends Food Sci. & Technol., vol. 81, pp. 2536 (Nov. 2018).

Hoffman, J.R., et al. "Protein—Which is Best?" J. Sports Sci. and Med., vol. 3, p. 118-130 (2004).

Tu, Chuanhai et al., "Characterization of Fermented Okara Powder and its Effects on lipid Oxidation of Emulsion-type Sausage Pork Sausage During Cold Storage", https://doi.org/10.7287/peerj.preprints.2636v1, published online Dec. 13, 2016.

Tu, Zongcai et al. "Study on Production of High-Activity Dietary Fiber from Soybean Dregs in Neurospora crassa", Food and Fermentation Industries, vol. 34(4), p. 68-70 (2008). (English Abstract).

Ren, Zhi-Qing et al. "Study on fermented by Neurospora crassa to improve structural style of soybean meal nutrition", Science and Technology of Food Industry, vol. 37(12), pp. 222-249 (2016). (English Abstract).

Liu, P. et al "Bio-transformation of agri-food wastes by newly isolated Neurospora crassa and Lactobacillus plantarum for egg production", Poultry Science, vol. 95, pp. 684-693 (2016).

Zhou, R. et al. "Fermented Soybean Dregs by Neurospora crassa: a Traditional Prebiotic Food", App. Biochem. Biotech., vol. 189, pp. 608-625 (published online May 11, 2019).

Kanti, A. et al. "Comparison of Neurospora crassa and Neurospora sitophila for phytase production at various fermentation temperatures", Biodiversitas, vol. 17(2), p. 769-775 (Oct. 2016).

Asri, R. et al. "Use of Mushrooms Neurospora Crassa in Making Steam Rangen for Improving Nutrition and Community Welfare", PELITA, vol. IV(1), p. 1-12 (2009) (Foreign language document with Google machine translation).

\* cited by examiner

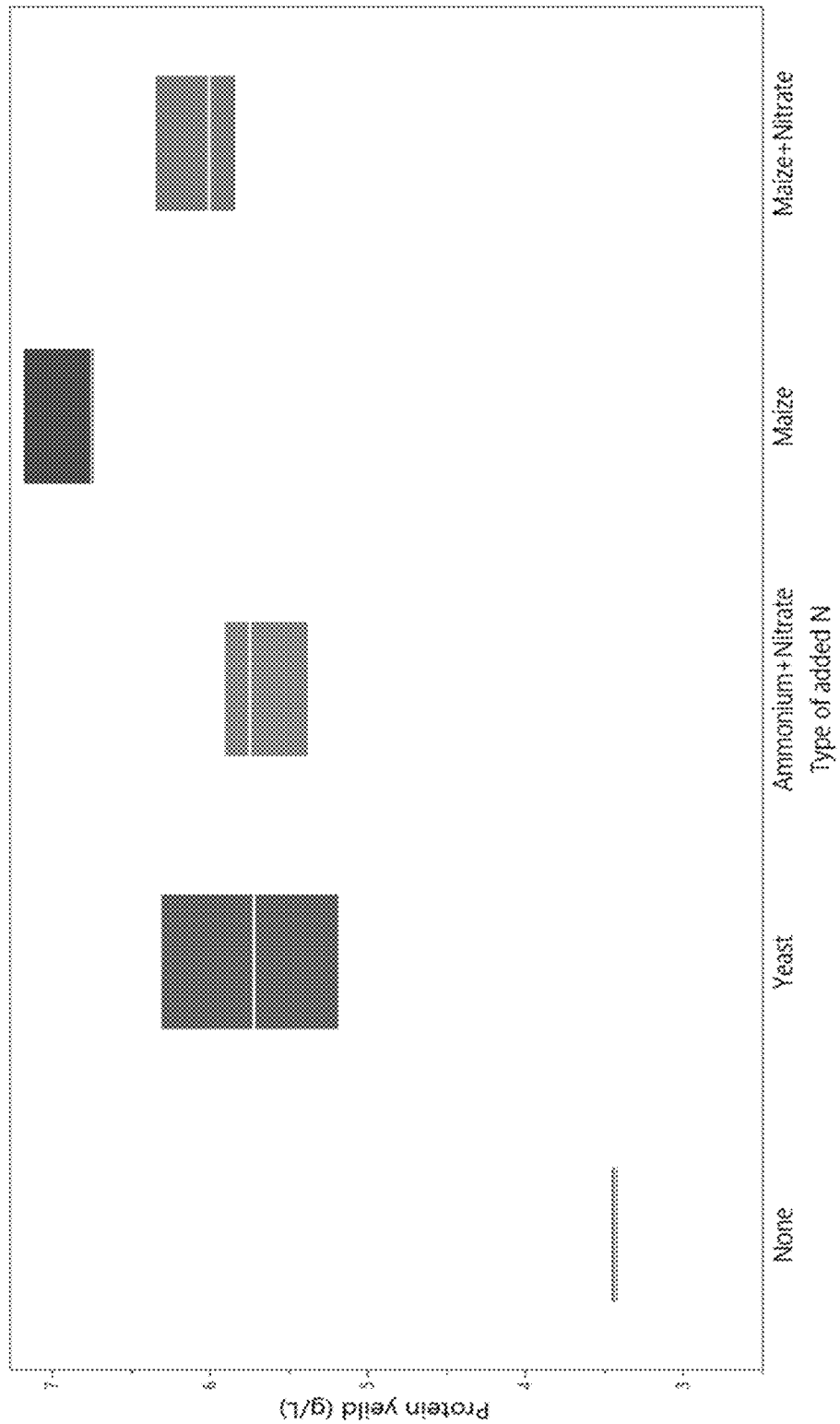

ENHANCED AEROBIC FERMENTATION METHODS FOR PRODUCING EDIBLE FUNGAL MYCELIUM BLENDED MEATS AND MEAT ANALOGUE COMPOSITIONS

CROSS REFERENCE TO RELATED APPLICATIONS

The present application claims the benefit of priority from U.S. provisional application No. 63/185,902, filed May 7, 2021, and is a continuation-in-part of U.S. patent application Ser. No. 16/586,150, filed Sep. 27, 2019, which in turn is a continuation of U.S. patent application Ser. No. 16/578,099, filed Sep. 20, 2019 (now U.S. Pat. No. 11,058,137), which in turn claims the benefit of priority from U.S. Provisional application No. 62/733,925, filed Sep. 20, 2018, the content of which are hereby incorporated by reference in its entirety.

FIELD OF THE DISCLOSURE

Provided herein are shelf-stable protein food ingredients, food products comprising the shelf-stable protein food ingredients, methods of their production, and methods of their use.

BACKGROUND

To keep up with global population growth projected to reach 10 billion by 2050, we must be able to produce 70% more food on Earth. The average American consumes over 200 pounds of meat per year. Meat as a protein source is becoming increasingly costly to humanity due to associated habitat conversion, water, and resource use. As environmental resources become more scarce, we cannot afford to invest valuable nutrient resources into inefficient food production processes such as farming of animals. The tasks of reducing meat consumption along with creating sustainable alternatives will be required to meet the protein demand of the future. On average, 5% of the calories from animal feed make it into the meat consumed by humans. These vital nutrients are only becoming more precious a commodity. The environmental budget of the planet will not allow humans to continue under such tremendous inefficiency.

The alternative protein industry is booming. The current landscape of plant protein ingredients is incredibly limited. Almost every product on the market relies on either wheat, soy, or pea proteins. There are two realms of texturization that companies use to produce their meat analogues—wet texturization and dry texturization. Virtually all texturized plant protein sold today as an ingredient is as a dry texturized protein. These ingredients are limited to the versatility of twin-screw extrusion systems, and the functionality of the three aforementioned plant protein inputs. The ingredients being produced are very similar to each other, and the two most widely used proteins (wheat and soy) are both in the list of the eight most common allergens. Texturized pea protein is still very expensive. In order to move the industry forward, alternative ingredients for the plant-based protein world are needed.

Cutting the amount of animal-derived meat needed to produce a meat product is a concept being investigated by many key players in the meat industry. Current ingredients in existing blended meats lack the protein, texture, and filamentous/fibrous nature of muscle and fat in meat. These ingredients, described as meat extenders, typically only consist of single ingredients, e.g. flours, powders, or crumbs, lacking nutrition and enhancement of the meat.

The food and beverage industries produce high volume food grade waste streams containing quality starches, sugars, nitrogen, fats, vitamins, minerals, and other nutrients. This material often goes to feed animals at an inefficient conversion rate or is treated as a complete waste and sent to landfills or treatment facilities. Leftover material from processing, extraction, and cultivation are available on a consistent basis. These are valuable food grade nutrients that cannot afford to be lost.

Potatoes are cultivated extensively in temperate climates across the globe and are sold fresh or processed. More than 50% of potatoes are processed into products such as French fries, chips, hash browns, and starch. During processing, the tuber is manipulated in a variety of ways to achieve certain properties of the final product. This includes cutting, shredding, sorting, blanching, steaming, peeling, and other methods used in various combinations to produce a variety of potato food products. Potato product consumers have fairly stringent standards for the quality of fresh and processed potatoes. These standards require the producers and processing plants to reject large percentages of products where the only deficiency may relate to aesthetics, size, and shape. These potato by-product solids retain much of their nutritional value and can still provide valuable carbohydrates, protein, fiber, vitamins, minerals, and micronutrients. Much of these solid potato rejects get landfilled, composted, or fed to animals at an inefficient conversion rate. They are often considered a burden by the potato processing industry and lost gains to growers.

Some research has been done on utilizing potato processing wastes, such as starch water and protein liquor (a waste stream of starch extraction), as a substrate to ferment certain types of fungi. The main theme in those works was the remediation of the waste, producing fermentation metabolites such as ethanol, or improving the animal feed generated from processing potato waste. This is not surprising since potato wastewaters are typically lower value streams because of their low carbohydrate density, their contamination with cleaning chemicals and other plant wastewaters, and high contaminant load. Concentrations of nutrients are relatively low and cannot be controlled in these wastewaters. While it is possible to ferment fungi using these certain wastewaters, the material that is generated is largely inadequate or insufficient for human consumption, let alone meat analogs. Large amounts of potato solids are generated from the cutting, sizing, spot removal, and processing of the tuber. Additionally, large amounts of products are often rejected due to small manufacturing defects or issues. These potato rejects render large volumes of human food grade potato materials essentially useless.

Commercial plant agriculture is dependent on environmental parameters beyond the control of man. Weather, climate, wind, pathogens, blight, disasters, and more can unpredictably wipe out entire areas of food production. Controlled agriculture is essential; however, it is limited to indoor plant farming reliant on artificial lighting powered primarily by the electric grid and in effect, coal and natural gas.

Significant resources are being directed towards sustainable methods of producing cultured meats and meat analogues. Meat alternatives in the marketplace are mostly derived from plant biomass. Plant based analogues and meat fillers commonly require significant manipulation and additives to mimic the texture, nutritional profile, and properties of meat.

Current meat analogues rely almost entirely on texturized vegetable proteins (TVP). These ingredient supplies are reliant on costly texturization processes, limited manufacturing capacity, environmental impacts on cultivation, supply of raw material, and, often times, processing aids. These ingredients have functional limitations as they can only achieve certain textures and qualities. The base plant biomass of most TVP is wheat and soy, two of the eight common allergens, and therefore not preferred as food ingredients. Some texturized pea exists in the marketplace, however, it is limited in use by its functionality, high cost and constricted supply.

An alternative to TVP is the use of filamentous fungi as a commercial human food component to produce meat-like products. Fungal mycelium is made of thin and long filaments, much like mammalian skeletal muscle cells. Furthermore, some fungi can produce high levels of protein, with all of the amino acids essential to human nutrition, and high amounts of minerals and vitamins. Therefore, fungal-derived ingredients have the potential of being developed into better meat-like products with textures that more realistically imitate animal-derived products, while providing a complete protein (containing all nine essential amino acids), having no allergens and toxins, and a low amount of sugar. Currently, the only major global producer of mycelium-based food products is Marlow Foods which produces Quorn™ from *Fusarium venenatum*. However, Marlow Foods does not supply mycelium based ingredients but rather complete food products. Despite high consumer and meat producer demand, the high cost and complexity of producing fungal biomass via fermentation create final products that are inferior to meat in texture, are costly, and have limited supply. These products are expensive to manufacture because of the cost of feedstock for fermentation. Additionally, products such as Quorn also rely heavily on additives such as egg albumin and sodium alginate to create a meat-like texture.

It is quite difficult to manufacture a microbial-based product that functions well as a meat replacer, or meat enhancer, and that is human-food ready. Significant innovation and R&D are needed in order to find ways of making microbial biomass materials edible, nutritional, and with the required texture and aroma that resembles meat and that is appreciated by consumers.

SUMMARY OF DISCLOSURE

By combining the potato solids, and therefore the fiber, cell wall components, and residual starch with the filamentous fungi, the compositions disclosed herein are unexpectedly superior in texture and flavor compared to other meat-like ingredients and to compositions produced by other methods of fungal fermentation. Using potato solids as described herein produces robust high yields of up to about 18 g of dry biomass per 1 L of liquefied diluted substrate. Surprisingly, the morphology of the filamentous fungi is positively affected by using the homogenized solid potatoes. Fungal growth on solid potato granules creates longer filaments that are entwined with residual plant fiber and starch. This results in a better meat-like texture. The compositions disclosed herein also produce a product that maintains a neutral color and an ability to be processed easily, two things that make the compositions advantageous over other biomass forms. The combination of improved texture, color and processability results in a superior meat-analog that is preferred by human testers in taste trials, and in comparison to a regular product made without using potato solids. Furthermore, this disclosure provides methods and composition to prepare media, potato manufacturing by-products and waste that improves the resulting yields from the fermentation and reduces the production cost. The present disclosure describes using solid potato materials in a high-yielding, simple, effective, and controlled fermentation process to produce a superior meat-like product that maintains all the positive attributes.

Provided herein are shelf-stable protein food ingredients that are versatile in production methods, functionality, and form. The ingredients can be completely allergen free and potentially cheaper than texturized pea protein. The shelf-stable protein food ingredients can have substantial impacts in the types of alternative protein food ingredients and products in the marketplace.

In an aspect, provided herein are fermented shelf-stable protein food ingredients that can be dry, stored, and readily integrated into the food ingredient supply chain. These ingredients are designed to be meat-like, versatile, and cost-effective to produce. They can be readily substituted for plant based protein ingredients and can be produced for a lower cost in many embodiments.

In an aspect, provided herein are methods for combining potato solid rejects from potato processing, harvest, and/or cultivation, with the fermentation of filamentous fungi. The methods disclosed herein result in a unique composition that can be processed into a high-protein food ingredient with unexpected enhancements to the texture of the product. This superior texture is advantageous in animal meat analog and meat blending applications.

In an aspect, provided herein are fermentation processes that harness waste nutrient streams from crop and food processing. In certain embodiments, the waste nutrient stream can be potato solids. Harnessing these streams has a multitude of benefits for society, and our planet as a whole. By utilizing these nutrient streams and converting them into high quality food ingredients and products, the methods disclosed herein include a process to produce a quality protein source without requiring significant land and carbon impacts on the planet compared to meat or even plants.

Fungi are decomposers. They complete degradation of complex organic molecules like lignin and cellulose in nature. By excreting digestive enzymes and acids, fungi are able to convert more complex carbohydrates into simple fermentable sugars. Their incredible efficiency at decomposing and consuming low value waste streams can be utilized to produce high value, quality food for the masses with low-cost, inexpensive inputs.

In an aspect, provided herein are shelf-stable protein food ingredients that create a means of reducing and replacing animal meat products. These shelf-stable protein food ingredients can provide all essential amino acids (significant amounts of protein), fiber, quality fats, and most essential micronutrients and vitamins. In certain embodiments, the production process is efficient and environmentally sustainable. In another aspect, processes for producing these foods are disclosed herein.

In an aspect, provided herein are fermented shelf-stable protein food ingredients that can be dry, stored, and readily integrated into the food-ingredient supply chain. These ingredients are designed to be meat-like (e.g. beef, pork, chicken, turkey, duck, fish, or crab), versatile, and cost-effective to produce. They can be readily substituted for plant-based protein ingredients such as extruded pea protein and can be produced for a lower cost in many embodiments. They can be integrated into formulas with other ingredients to perform in a variety of food products and as replacers and enhancers of meat, eggs, milk proteins, and fibers.

The shelf-stable protein food ingredients described herein can be produced in a refined, controlled, environment that mitigates most of the problems associated with traditional agriculture. The shelf-stable protein food ingredients can comprise filamentous fungi cultivated in optimized fermentation systems with low physical, financial, and environmental footprints. These systems are more typically utilized in the production of penicillin, enzymes, and organic acids but can be adapted for use in the production of food ingredients.

In an aspect, provided herein are applications of the shelf-stable biomass ingredients in meat analogs and blended meat products. In some aspects, contained herein are applications of the mycelium-derived products that are used without drying into shelf-stable particles.

Filamentous fungal mycelium has been consumed for centuries in the forms of tempeh, oncom, koji, and other foods, some of which are mentioned below. These products consist of filamentous fungi grown on solid substrates. Soy, rice, and other solid substrates are nutritious; however, these solid substrates can remain in the end product and dilute the potential end protein/nutrient content. These ingredients also hold dietary value on their own and do not require the fungi to become valuable to the human diet. They may be enhanced by the fungi; however, the fungal cells play a minor role in the end product.

In certain embodiments, the food ingredients and food products provided herein comprise fungal species established in human consumption and have stood the test of time. *Aspergillus oryzae* is the species used to make Koji (a fermented rice used in the production of sake, miso, and soy sauce). *Rhizopus oryzae* is a species used in fermenting tempeh. *Cordyceps militaris* and *Cordyceps sinensis* are edible fungi used in traditional Chinese Medicine. *Tuber magnatum*, better known as the Black Truffle, is an edible fungus known for its array of aromatic compounds that are responsible for its sought after flavor. *Fusarium* has been utilized as a protein source. *Penicillium* is used in cheese making. *Neurospora crassa, N. intermedia,* and *N. sitophila* are used to ferment oncom (a fermented tempeh-like soy, peanut, or legume food very commonly consumed on the mainland of Indonesia (Java) for centuries).

Filamentous fungi are known for their rapid cell replication, aggressive digestion, colonization timing, adaptability, and ease of propagation. This makes them well suited for scaled food production.

In an aspect, provided herein are fermentation processes that utilize potato solids materials from potato processing. The processes as disclosed herein using solid potato rejected materials are unique in that the concentrations of the nutrients are controlled and can capture much more material out of the potato. Furthermore, the methods disclosed herein have unexpectedly improved yields and characteristics from non-potato based fermentations. The present disclosed methods generate a palatable and delicious food product that is ready to consume or be formulated into meat analogues. The unique utilization of the rejected potato materials allows generation of this high-quality material.

In an aspect, provided herein are shelf-stable food ingredients that create a means of reducing and replacing animal meat products. These shelf-stable food ingredients can provide all human essential amino acids, significant amounts of protein, fiber, quality fats, and essential micronutrients and vitamins. In certain embodiments, the production process is efficient and environmentally sustainable. In some aspects, processes for producing these foods are disclosed herein.

The shelf-stable food ingredients described herein can be produced in a refined, controlled environment that mitigates most of the problems associated with conventional agriculture. The shelf-stable food ingredients can comprise fungi cultivated in optimized fermentation systems with low physical, financial, and environmental footprints. These systems are more typically utilized in the production of fungal-derived products, such as penicillin, enzymes, and organic acids, but can be adapted for use in the production of food ingredients from mycelial biomass.

In certain embodiments, the food ingredients and food products provided herein comprise fungal species suitable for human consumption. There are only a handful of Ascomycota fungi that are being consumed as food, or food ingredients, across the globe. *Neurospora intermedia, Neurospora sitophila,* and *Neurospora crassa* are used to ferment oncom (fermented tempeh-like soy, peanut, or legume food very commonly consumed on the mainland of Indonesia (Java) for centuries) and are also present in some cheeses. Another species that is known to saccharify starch effectively are *Aspergillus oryzae* and *Aspergillus sojae* and are used for production of sake, soy sauce and miso.

Filamentous fungi are known for their short colonization timing, rapid cell division, prototrophy, adaptability, ability to digest complex plant materials, and ease of propagation. Taken together with the good nutritional composition of fungi this makes them well suited for scaled food production.

This unique combination of fermentation methods, potato reject based substrate sources, product formats and product applications gives a meat-like product superior to other production methods due to the higher yield, enhanced texture, better color, and lower cost.

The new potato/fungi based ingredients maintain a meat-like texture that is superior to any plant-based extruded protein because of their unique combination of natural fibrous texture, variation in micro structure, protein content, high water retention properties and nutritional value.

The methods disclosed herein result in a superior yield to other substrates. The potato based substrate generates up to about 18 g/l of dry mycelium biomass yield compared to about 11 g/l generated by other substrates. Furthermore, the new process for utilizing solid potato rejects improves production yields compared to previous disclosures in which liquid potato waste streams, such as starch water and potato protein liquor (PPL), are used. For example Guo et al., ("Fermentation and kinetics characteristics of a biofocculant from potato starch wastewater and its application". (2018). Scientific Reports. 8:3631) describe potato starch water and Souza Filho et al., ("Techno-Economic and Life Cycle Assessment of Wastewater Management from Potato Starch Production: Present Status and Alternative Biotreatments. (2017). Fermentation. 3:56) report the use of PPL. In these, and other examples, the reported yields are lower than 10 g of dry biomass per 1 L of formulized media (compared to about 18 g/l as disclosed herein) and the mycelial biomass is not suited for human food ingredients but is rather aimed for animal feed. Additionally, the process disclosed herein presents an improvement over previous process for producing mycelium based food products from residual plant materials since the starch does not have to be hydrolyzed prior to fermentation. Furthermore, additional nutrient additives can be avoided. Thus the methods provided herein present a cost effective approach to elevate the protein production levels. In summary, these improvements and enhancements are a significant factor because of the increased total output, reduced cost, and greater system efficiency at scale.

Food Ingredients

In one aspect, provided herein are shelf-stable protein food ingredients. The shelf-stable protein food ingredients comprise cultured fungal biomass and a limited amount of water. The fungal biomass and other ingredients are described in detail herein. The shelf-stable food ingredients comprise particles of sizes and forms with properties described herein. Advantageously, the shelf-stable protein food ingredients can be stored, transported, and delivered within the food supply. They can be sold or consumed as is, or, preferably, they can be combined with other food ingredients to provide food ingredient compositions and food products.

Filamentous fungal mycelium maintains a texture similar to ground meat with minimal manipulation. Filamentous fungi mycelium described herein comprises groups of connected cells fused end to end in filaments called hyphae. These hyphae typically range from 2-16 microns in diameter and can be centimeters long. These hyphae are typically one single cell thick. These morphologies give the hyphae naturally occurring texture properties similar to meat muscle fiber as a result of the bundling of the hyphae and the substantial moisture retention capacity of the mycelium. This makes mycelium a perfect candidate for food ingredients and food products.

In certain embodiments, the fungal mycelium is processed into a shelf-stable protein food ingredient that can be hydrated and used on its own or, advantageously, in a variety of food products including but not limited to meat extenders, meat analogues, cultured meat cell scaffoldings, and other food products requiring textured proteins. As used herein, these "textured cultured proteins" (hereinafter "TCP") are dry, shelf stable, and easily used as a replacement for lower quality more expensive texturized vegetable proteins (hereinafter "TVP").

The material produced by the methods disclosed herein can be utilized in a variety of food formats. The dry shelf stable form of the material can be combined with water and used as meat-like shreds or be formed into whole cut meat analogues. The wet form of the material can be used directly as a meat replacer in food formulas.

The dry particles of the present disclosure can be combined with other plant ingredients known to those skilled in the art of making meat analogs. These ingredient combinations can enhance certain properties of the ingredient to tailor it for certain applications in food. The dry particles can be combined with water to rehydrate and then blended into a food product. They are shelf-stable until they are required to be integrated into a food product. At that time they can be hydrated and used. These dry particles can be utilized in any food composition that may use textured plant protein.

The wet (about 60% to about 85% moisture content) potato/fungus mass can be used as a stand-alone ingredient (for example, in products requiring a meat replacer). In some embodiments, the wet mass can be directly blended into meat with no additional ingredients. In other embodiments, the wet mass can be combined with other plant or non-animal ingredients that are both dry and hydrated at a variety of moisture contents (for example, about 50% to about 95%). Different combinations of ingredients have advantages in different product formats. The wet mass can be treated in several different ways to create different ingredient formats.

In certain embodiments, filamentous fungal mycelium described herein comprises significant concentrations of nutrients. In certain embodiments, crude protein accounts for up to 60% of the untreated desiccated biomass. Most species contain all of the essential amino acids of the human diet. Many species contain all of the necessary B vitamins when un-supplemented (except B12). The mycelium contains many dietary minerals needed in the human diet including but not limited to zinc, iron, manganese, magnesium, potassium, selenium and calcium. All of these minerals except for zinc have been shown to be more bioavailable to the body when sourced from mushrooms and fungi compared to meat and plant sources. The mycelium is naturally high in fiber.

In certain embodiments, the fat composition of the mycelium described herein comprises or consists of mostly mono- and polyunsaturated fats and is very low in saturated fats. The biomass also may contain omega-6, linoleic acid, and omega-3, linolenic acid.

In certain embodiments, the dry shelf-stable ingredients described herein comprise significant fiber. This substantial concentration of dietary fiber in the TCP is beneficial when consuming TCP as a meat alternative, as well as being beneficial in meat/TCP blends. The present fiber increases the digestibility and bioavailability of the nutrients in the meats consumed in the blend.

It is therefore an aspect described herein to produce a food ingredient using fungi, many species of which are already accepted in their recognition of safety in the diet of humans and significantly higher in protein and fungal cells than classic fermented foods that contain some of these species.

Phosphates are commonly used in meat products to increase moisture retention by creating space between proteins. Provided herein are filamentous mycelium that can retain over 80% water. At levels of 60-85% water content the dry shelf-stable ingredient of the present disclosure mixes well with meats and acts as a tackifying agent helping to bind the meat while holding moisture in the meat mixture. The filamentous nature of the mycelium maintains natural space between proteins. This moisture helps the meat retain its volatile aromatics effectively preventing flavor loss. This may have implications is shelf-life extension of some meat products. Upon dehydration, the mycelium described herein can remain shelf stable and retain a similar water content to the fresh material when re-hydrated.

Process

In another aspect, provided herein are methods for producing the shelf-stable protein food ingredients. In certain embodiments, the methods comprise the steps of culturing fungal biomass in a growth medium, harvesting the fungal biomass, optionally processing the fungal biomass, optionally sizing the fungal biomass to form particles, and drying the particles to form the food ingredients.

In certain embodiments, provided herein are methods of producing a meat-textured high protein ingredient from filamentous fungal mycelium produced with plant biomass hydrolysate as the primary growth media. The methods comprise the steps of generating plant biomass hydrolysate/extract; enhancing the hydrolysate with supplements to enhance yields, nutritional profile, and morphology; sterilizing said substrate; inoculating substrate with filamentous fungi; propagating the filamentous fungus in optimized aerobic fermentation conditions; harvesting pure fungal mycelium, de-watering, shaping, sizing, drying and pasteurizing; integrating dried and shaped ingredient into blended meat extension ingredients; hydrating and blending hydrated ingredient in ground meats; and utilizing aforementioned ingredients in blended plant and mushroom products.

In certain embodiments, provided herein are methods of producing a shelf-stable protein ingredient from filamentous fungal mycelium with substrates based on glucose, sucrose, sugars, starches, and/or biotin as well as salt forms of nitrogen, phosphorous, potassium and other necessary elements. The methods comprise mixing said substrate; sterilizing said substrate; inoculating substrate with filamentous fungi; propagating the filamentous fungi in optimized aerobic fermentation conditions; harvesting pure fungal mycelium, de-watering, shaping, sizing, drying and pasteurizing; integrating dried and shaped ingredient into blended meat extension ingredients; hydrating and blending hydrated ingredient in ground meats; and utilizing aforementioned ingredients in blended plant and mushroom products.

In certain embodiments, provided herein are methods for fermenting filamentous fungi with carbohydrate rich and other raw plant biomass to produce meat-textured ingredients. These methods may entail introduction of plant flour, granules, grains, legumes, or combinations thereof or other plant biomass into the fermentation liquid described herein.

In certain embodiments, provided herein are methods for converting the harvested fungal mycelium into a meat like particulate dry ingredient. In some embodiments, the ingredient is combined with other ingredients for functional enhancement; in some embodiments, the ingredient is used as a stand-alone ingredient; in some embodiments, the ingredient is hydrated with water and integrated into meats; in some embodiments, the ingredient is hydrated and integrated into meat analogues including but not limited to burgers, sausages, patties, nuggets, and more.

By using fermentation to produce these high protein textured ingredients, carbohydrates, other nutrients, and oxygen are converted into protein. Such methods can use less space, resources, and time than those of conventional conversions in animal agriculture.

Filamentous fungi fermentation can be carried out with waste streams as primary sources of nutrients, displacing the need to introduce so many purified nutrients into the growing medium.

Beet pulp, potato solids, potato peel, and potato processing water, processed grains, process fruits, rice polishings, and much more are abundant and available and can be used for sourcing of components in fungal fermentation substrate. Filamentous fungi effectively convert sugars and starches from these sources into biomass at a high efficiency. Some industrial fermentation operations, such as Cargill's lactic acid plant in Blair, Nebraska, USA, employ these concepts. Cargill uses beet pulp from refining sugar at the Blair plant for their primary carbohydrate source for the production of lactic acid.

In some embodiments more traditional fermentation substrates are used for producing the TCP described herein.

Preparation of potato solids derived media: The current disclosure utilizes potato solids rejects as the primary fermentation substrate component. This material is homogenized to break down the tuber granules and the peel of the potato.

Supplementation: In some embodiments, the potato slurry can be supplemented with nutrients. For example, the optional nutrients are selected from nitrogen sources, peptones, syrups, sugars, vitamins, and trace elements. In some embodiments, the potato slurry is combined with inorganic nitrogen sources or organic nitrogen sources. In certain embodiments, it can be combined with other nutrients to enhance the fermentation or final product properties (for example, biotin and thiamin can improve growth and protein production if levels in the potato are too low (biotin is an essential B vitamin that cannot be synthesized by some fungi), peptones can be added as a nitrogen source and base amino acid source, B12 can be added to facilitate higher B12 levels and trace elements can improve biomass yield).

Fermentation: The prepared potato solid derived fermentation substrate can be inoculated with filamentous fungi (for example, *Neurospora intermedia, Neurospora sitophila, Neurospora crassa*, and *Aspergillus oryzae*). In certain embodiments, the fungi is fermented under aerobic conditions until an acceptable yield is reached.

Ingredient processing: the potato/fungi slurry can be dewatered down to about 70% moisture content. This mass is optionally manipulated into desired particle sizes and dried to about 10%, about 9%, about 8%, about 7%, about 6%, about 5%, about 4%, or about 3% moisture content. Alternatively, the mass is optionally processed into desired shredded or piece sizes and used without drying.

In some embodiments, either dry particles or wet shreds/shapes at about 70% moisture content can be combined with other plant based or other food ingredients and formed into meat analogues or are directly blended into meat products. These products are then cooked in a way known to one skilled in the art of preparing meat-like products.

Food Products

In another aspect, provided herein are food products. The food products comprise one or more of the shelf-stable protein food ingredients and one or more additional food ingredients. The additional food ingredients can be meat proteins, plant proteins, combinations thereof, or any additional food ingredient deemed useful by the practitioner of skill in the art. The food products can be consumed by animals, for instance mammals. In certain embodiments, the food products are for pet consumption. In certain embodiments, the food products are for human consumption.

In another aspect, provided herein are food compositions comprising a shelf-stable protein food ingredient and one or more meats. In particular embodiments, the food compositions comprise the shelf-stable protein food ingredient in an amount of at least 5% w/w and at least one meat in an amount of at least 10% w/w. Shelf-stable protein food ingredients and useful meats are described in detail in the sections below, along with methods of preparing the food compositions.

In an embodiment, provided herein are methods for processing fungal mycelium described herein into a pasteurized biomass that can be blended into meat to make blended meat products described herein.

Converting diet to meat alternatives has a place in the changing diet of humans; however, meat consumption is unlikely to be entirely replaced. The concept of extended meats has existed in the art for years. By simply extending the meat in processed meat products, one can significantly reduce overall meat production and demand. Current extension agents provide only some of the needed properties to have an indistinguishable profile in the blended meat. Mushrooms like portabellas are sometimes used to dilute meat and retain moisture, but only provide some of the desired properties of meat extenders while lacking others.

In certain embodiments the food ingredients described herein provide an alternative to texturized vegetable protein (TVP), the core ingredient in most meat analogues on the market.

It is therefore an aspect described herein to utilize the food ingredients provided herein for applications including but not limited to meat extension products, meat analogue products, baked good products, food products requiring binding agents, food products requiring gels, food products needing protein, food products needing fiber, and other food products.

Embodiments of the present disclosure may thus relate to one of the enumerated example embodiments (Embodiment 1 to Embodiment 45) listed below:

Embodiment 1. A method of producing a shelf-stable food ingredient from filamentous fungal biomass, the method comprising:
  a) culturing a filamentous fungi from the genus *Neurospora* or *Aspergillus* in a liquid growth medium to produce the filamentous fungal biomass slurry comprising about 0.5-8% biomass, wherein the liquid growth medium comprises potato solids comminuted to a size of about 20 μm to 50 μm and at a concentration of about 5 g to about 50 g of dry weight per liter of liquid growth medium;
  b) harvesting and dewatering the filamentous fungal biomass slurry to produce a harvested filamentous fungal biomass comprising about 60-85% water and about 15-40% filamentous fungal biomass;
  c) shredding the filamentous fungal biomass to form filamentous particles and drying the filamentous particles to about 4% to about 10% water, or to about 4% to about 6% water; and
  d) sizing the dried filamentous particles to comprise a mean particle size between about 5 mm and about 20 mm or between about 5 mm and about 50 mm to produce a self-stable food ingredient comprising sized dried filamentous particles having a residual potato content ranging from about 0.1 g to about 10 g per 100 g of dried filamentous particles or about 1 g to about 5 g per 100 g of dried filamentous particles.

Embodiment 2. The method of Embodiment 1, further comprising
  e) hydrating the sized dried filamentous particles to about 30% to about 70% water content to form a hydrated food product.

Embodiment 3. The method of Embodiment 1, wherein the liquid growth medium further comprises one or more nitrogen sources, starches, fatty acids, sugars, minerals, trace elements, vitamins, extracts, or combinations thereof.

Embodiment 4. The method of Embodiment 1, wherein the potato solids comprise about 1% to about 60% peel retained potato solids; about 10 g to about 40 g starch per 100 g wet potato solids; about 1 g to about 5 g protein per 100 g wet potato solids, and a pH of about 5 to about 6.

Embodiment 5. The method of Embodiment 1, wherein the potato solids are hydrolyzed prior to adding to the liquid growth medium.

Embodiment 6. The method of Embodiment 2, further comprising pasteurizing the food product.

Embodiment 7. The method of Embodiment 2, further comprising shaping the food product into patties, nuggets, balls, or sausage links.

Embodiment 8. The method of Embodiment 2, wherein the food product comprises protein in an w/w amount of 5-100%, 5-75%, 5-50%, 5-45%, 5-40%, 5-35%, 5-30%, 5-25%, 5-20%, or 5-15%.

Embodiment 9. The method of Embodiment 2 further comprising combining the food product with plant ingredients, one or more natural flavorings, or both, wherein the one or more natural flavorings is a natural chicken flavoring, a natural beef flavoring, or a natural pork flavoring.

Embodiment 10. The method of Embodiment 2 further comprising mixing the food product with a ground meat to produce a meat blended food product.

Embodiment 11. The method of Embodiment 10, wherein the ground meat is selected from the group consisting of beef, pork, chicken, turkey, fish, lamb, crab, lobster, venison, bison, and combinations thereof.

Embodiment 12. The method of Embodiment 10, wherein the meat blended food product comprises at least about 5% w/w of the food product and at least about 10% w/w of the ground meat.

Embodiment 13. The method of Embodiment 10, wherein the meat blended food product comprises at least about 5% w/w of the food product and at least about 10% w/w of the meat and wherein the food product comprises protein in an w/w amount of 5-100%, 5-75%, 5-50%, 5-45%, 5-40%, 5-35%, 5-30%, 5-25%, 5-20%, or 5-15%.

Embodiment 14. The method of Embodiment 10, wherein the meat blended food product comprises protein in an w/w amount of 5-100%, 5-75%, 5-50%, 5-45%, 5-40%, 5-35%, 5-30%, 5-25%, 5-20%, or 5-15%.

Embodiment 15. The method of Embodiment 2, wherein the food product is ground into a flour before blending with a ground meat.

Embodiment 16. The method of Embodiment 2 further comprising combining the food product with plant ingredients.

Embodiment 17. The method of Embodiment 1, wherein the filamentous species are *Neurospora intermedia, Neurospora sitophila, Neurospora crassa, Aspergillus oryzae*, or a combination of *Neurospora intermedia, Neurospora crassa, Neurospora sitophila*, and *Aspergillus oryzae*.

Embodiment 18. The method of Embodiment 2, wherein the dried filamentous particles are sized by continuous sieving using 2 mm and 12 mm sieves.

Embodiment 19. The method of Embodiment 1, wherein about 10 g, about 11 g, about 12 g, about 13 g, about 14 g, about 15 g, about 16 g, about 17 g, about 18 g, about 19 g, or about 20 g or more of the filamentous fungal biomass slurry is produced per liter of liquid growth medium.

Embodiment 20. A shelf-stable food ingredient comprising filamentous fungal particles from the genus *Neurospora* or *Aspergillus* with a mean particle size between about 5 mm and about 20 mm or between about 5 mm and about 50 mm and potato content in an amount ranging about 0.1 g to about 10 g per 100 g of filamentous fungal particles or about 1 g to about 5 g per 100 g of filamentous fungal particles;
  wherein the filamentous fungal particles consist essentially of cultured filamentous fungal biomass from the genus *Neurospora* in an amount at least about 90-99% w/w and water in an amount of about 1% to about 9% w/w.

Embodiment 21. The shelf-stable food ingredient of Embodiment 20, wherein the fungal biomass is from the species, *Neurospora intermedia, Neurospora sitophila, Neurospora crassa, Aspergillus oryzae*, or a combination of *Neurospora intermedia, Neurospora crassa, Neurospora sitophila*, and *Aspergillus oryzae*.

Embodiment 22. The shelf-stable food ingredient of Embodiment 20, wherein the food ingredient comprises protein in an w/w amount of 5-100%, 5-75%, 5-50%, 5-45%, 5-40%, 5-35%, 5-30%, 5-25%, 5-20%, or 5-15%; fat in an amount of 1-80%; or both.

Embodiment 23. The shelf-stable food ingredient of Embodiment 20, further comprising albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, citrus fiber, bamboo cellulose, annatto, carrageenan, gluten, hemoglobin, modified starch, acetic acid, sodium nitrite, sodium benzoate, soy lecithin, natural flavorings, or any combination thereof.

Embodiment 24. A food product comprising:
a) filamentous fungal particles from the genus *Neurospora* or *Aspergillus* with a mean particle size between about 5 mm and about 50 mm or between about 5 mm and about 20 mm in an amount of at least about 5% w/w, water in the amount of about 4% to about 8%, and a potato content ranging from about 0.1 g to about 10 g per 100 g of filamentous fungal particles or about 1 g to about 5 g per 100 g of filamentous fungal particles; and
b) a food ingredient in an amount of at least about 10% w/w.

Embodiment 25. The food product of Embodiment 24, wherein the food product comprises about 5-50% w/w of the fungal particles and about 10-40% w/w of the food ingredient, wherein the food product comprises protein in an w/w amount of 5-100%, 5-75%, 5-50%, 5-45%, 5-40%, 5-35%, 5-30%, 5-25%, 5-20%, or 5-15%; fat in an amount of 1-80%; or both.

Embodiment 26. The food product of Embodiment 24, wherein the fungal particles are selected from the species of *Neurospora intermedia, Neurospora sitophila, Neurospora crassa*, and *Aspergillus oryza* or a combination of *Neurospora intermedia, Neurospora crassa, Neurospora sitophila* and *Aspergillus oryza*.

Embodiment 27. The food product of Embodiment 24, further comprising albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, citrus fiber, bamboo cellulose, annatto, carrageenan, gluten, hemoglobin, modified starch, acetic acid, sodium nitrite, sodium benzoate, soy lecithin, natural flavorings, or any combination thereof.

Embodiment 28. The food product of Embodiment 24, wherein the food ingredient comprises:
a) one or more meat ingredients;
b) one or more plant ingredients; or
c) both one or more meat ingredients and one or more plant ingredients.

Embodiment 29. The food product of Embodiment 28, wherein the food ingredient further comprises the one or more meat ingredients and optionally water to provide a water content comprising about 30% to about 70%.

Embodiment 30. The food product of Embodiment 28, wherein the one or more meat ingredients is selected from beef, pork, chicken, turkey, fish, lamb, crab, lobster, venison, bison, and combinations thereof.

Embodiment 31. The food product of Embodiment 24, wherein the food product is in the shape of a patty, nugget, ball, or sausage link.

Embodiment 32. The food product of Embodiment 24, further comprising one or more natural flavorings selected from the group consisting of: a natural chicken flavoring, a natural beef flavoring, and a natural pork flavoring.

Embodiment 33. A method of producing a meat analogue food product from a filamentous fungal mycelium, wherein the method comprises:
a) providing a shelf-stable protein food ingredient comprising: filamentous fungal particles from the genus *Neurospora* or *Aspergillus* with a mean particle size between about 5 mm and about 20 mm or between about 5 mm and about 50 mm, said filamentous fungal particles consisting essentially of cultured filamentous fungal biomass from the genus *Neurospora* or *Aspergillus* in an amount at least about 90-99% w/w; a potato content ranging from about 0.1 g to about 10 g per 100 g of filamentous fungal particles or about 1 g to about 5 g per 100 g of filamentous fungal particles; and water in an amount of about 1% to about 9% w/w; and
b) hydrating the shelf-stable protein food ingredient to between about 30% to 70% water content to form the meat analogue food product.

Embodiment 34. A method of producing a filamentous fungal biomass, the method comprising:
a) culturing a filamentous fungi from the genus *Neurospora* or *Aspergillus* in a liquid growth medium to produce the filamentous fungal biomass slurry comprising about 0.5-8% biomass, wherein the liquid growth medium comprises potato solids comminuted to a size of about 20 µm to 50 µm and at a concentration of about 5 g to about 50 g of dry weight per liter of liquid growth medium; and
b) harvesting and dewatering the filamentous fungal biomass slurry to produce a harvested filamentous fungal biomass comprising about 60-85% water and about 15-40% filamentous fungal biomass having a residual potato content ranging from about 0.5 g to about 5 g per 100 g of filamentous fungal biomass or about 1 g to about 5 g per 100 g of filamentous fungal biomass.

Embodiment 35. The method of Embodiment 34, wherein the liquid growth medium further comprises one or more nitrogen sources, starches, fatty acids, sugars, minerals, trace elements, vitamins, extracts, or combinations thereof.

Embodiment 36. The method of Embodiment 34, wherein the potato solids comprise about 1% to about 60% peel retained potato solids; about 10 g to about 40 g starch per 100 g wet potato solids; about 1 g to about 5 g protein per 100 g wet potato solids, and a pH of about 5 to about 6.

Embodiment 37. The method of Embodiment 34, wherein the potato solids are hydrolyzed prior to adding to the liquid growth medium.

Embodiment 38. The method of Embodiment 34, further comprising pasteurizing the filamentous fungal biomass.

Embodiment 39. The method of Embodiment 34, wherein the filamentous fungal biomass comprises protein in an w/w amount of 5-100%, 5-75%, 5-50%, 5-45%, 5-40%, 5-35%, 5-30%, 5-25%, 5-20%, or 5-15%.

Embodiment 40. The method of Embodiment 34, wherein the filamentous species are *Neurospora intermedia, Neurospora sitophila, Neurospora crassa, Aspergillus oryzae*, or a combination of *Neurospora intermedia, Neurospora crassa, Neurospora sitophila*, and *Aspergillus oryzae*.

Embodiment 41. A food product comprising filamentous fungal biomass from the genus *Neurospora* or *Aspergillus* comprising about 60-85% water and about 15-40% filamentous fungal biomass having a residual potato content ranging from about 0.5 g to about 5 g per 100 g of filamentous fungal biomass or about 1 g to about 5 g per 100 g of filamentous fungal biomass.

Embodiment 42. The food product of Embodiment 41, wherein the food product comprises protein in an w/w amount of 5-100%, 5-75%, 5-50%, 5-45%, 5-40%, 5-35%, 5-30%, 5-25%, 5-20%, or 5-15%; fat in an amount of 1-80%; or both.

Embodiment 43. The food product of Embodiment 41, wherein the fungal particles are selected from the species of *Neurospora intermedia, Neurospora sitophila, Neurospora*

*crassa*, and *Aspergillus oryza* or a combination of *Neurospora intermedia, Neurospora crassa, Neurospora sitophila* and *Aspergillus oryza*.

Embodiment 44. The food product of Embodiment 41, further comprising albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, citrus fiber, bamboo cellulose, annatto, carrageenan, gluten, hemoglobin, modified starch, acetic acid, sodium nitrite, sodium benzoate, soy lecithin, natural flavorings, or any combination thereof.

Embodiment 45. The food product of Embodiment 41, further comprising one or more natural flavorings selected from the group consisting of: a natural chicken flavoring, a natural beef flavoring, and a natural pork flavoring.

BRIEF DESCRIPTION OF THE FIGURES

FIGS. 10A-10C show that the protein content in the cultured *N. intermedia* mycelium produced from solid potatoes can be boosted by incorporating nitrogen into the fermented substrate. Potato solids were used in fermenting fungal biomass. After collecting and drying the mycelium, the total protein content in the products was measured (FIG. 10A). Panels are of different potato solids concentrations (g/l), the median and lower (Q1) and upper (Q3) quartile of each treatment are shown in the boxplot. Data were analyzed using ANCOVA and Dunnett's test using PS without nitrogen addition as control (FIG. 10B). Error bars show 95% confidence intervals of the means. FIG. 10C. Total protein yield from mycelium cultivated on potato solids with various supplemental nitrogen. The protein content in cultured *N. crassa* mycelium produced from solid potatoes can be greatly increased by incorporating different nitrogen into the fermented substrate. Potato solids were used in fermenting fungal biomass. After collecting and drying the mycelium, the total protein content in the products was measured (method AOAC 2011.04).

DETAILED DESCRIPTION

Figure 1:
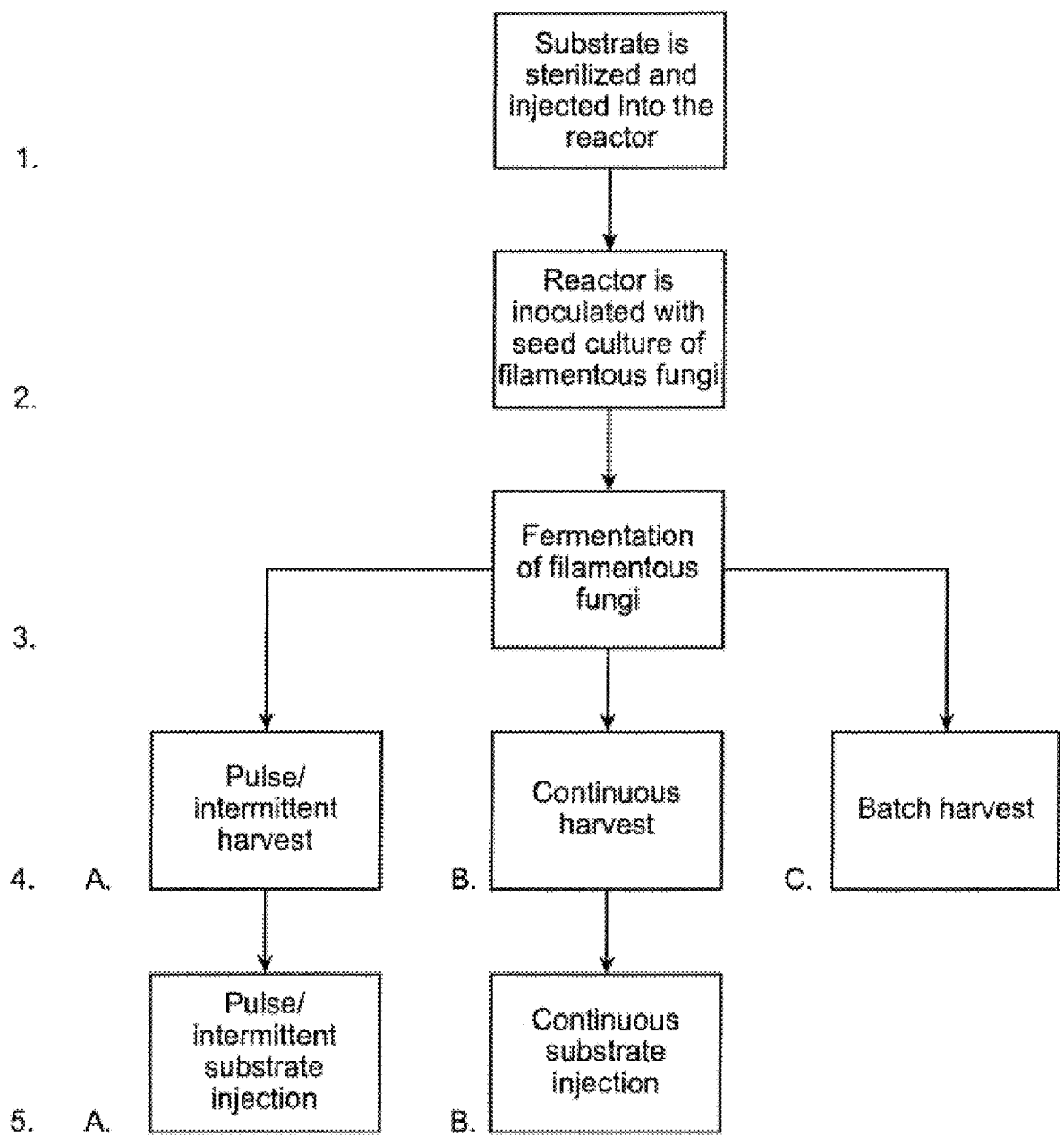
FIG. 1 provides an overview of an embodiment of the fermentation process used to produce the biomass described herein.

For the purposes of describing and defining the present disclosure it is noted that the terms "increase", "increases", "increased", "greater", "higher", and "lower" are utilized herein to represent non-quantitative comparisons, values, measurements, or other representations to a stated reference or control.

Unless otherwise apparent from the context, the term "about" encompasses insubstantial variations, such as values within a standard margin of error of measurement (e.g., SEM) of a stated value. The term "about" as used herein when referring to a measurable value such as a parameter, an amount, a temporal duration, is meant to encompass variations of +/−10% or less, +/−5% or less, or +/−1% or less or less of and from the specified value. It is to be understood that the value to which the modifier "about" refers is itself also disclosed.

Methods of Production

In particular embodiments, provided herein are methods for producing shelf-stable protein food ingredients. In certain embodiments, the methods comprise the steps of culturing filamentous fungi in growth medium; harvesting filamentous fungal biomass; optionally, processing the harvested filamentous fungal biomass; optionally, sizing the biomass to form particles; and drying the particles to form the food ingredient. In certain embodiments, the methods comprise the steps of culturing filamentous fungi in growth medium; optionally supplementing the growth medium to form a mixed fungal biomass slurry; harvesting filamentous fungal biomass; optionally, processing the harvested filamentous fungal biomass; optionally supplementing the processed biomass to form a complex ingredient; optionally sizing the biomass to form pieces; and drying the pieces to form the food ingredient.

In the culturing step, the filamentous fungus can be cultured according to standard techniques. The culturing typically comprises growing the filamentous fungus in a liquid growth medium. In certain embodiments, the growth medium comprises hydrolyzed plant biomass byproducts and wastewater streams of the food and beverage industries as well as low-cost plant ingredients and other substrates.

In certain embodiments, the culture is batch culture, fed-batch culture, or continuous culture. The growth medium includes the ingredients described below. Additional additives can be provided according to the judgment of the practitioner in the art. Culture conditions are within the skill of those in the art including culture volume, temperature, agitation, oxygen levels, nitrogen levels, carbon dioxide levels, and any other condition apparent to those of skill.

In certain embodiments, pure oxygen is used in the aeration of the fermentation. Injecting $O_2$ into the bioreactor can allow maximum interaction with the gas bubbles and substrate while maximizing diffusion of the $O_2$. Pressure swing adsorption (PSA) oxygen concentration is sometimes used to continuously inject $O_2$.

The fungal fermentation can operate with a wide pH range. In certain embodiments the pH is between about pH 2.4 and about pH 8.5, between about pH 3 and about pH 7.5, between about pH 3 and about pH 6.5, between about pH 3 and about pH 5.5, or between about pH 3.5 and about pH 4.5.

The cultured filamentous fungi can be harvested and dewatered according to any standard technique. The methods include any harvesting technique deemed useful to the practitioner in the art. Useful techniques include centrifugation, pressing, screening, and filtration. In certain embodiments, the filamentous fungi are dewatered and separated by centrifugation. In certain embodiments, the filamentous fungi are dewatered and separated via screw press. In certain embodiments fungi are dewatered and separated via de-watering vibratory screen. In certain embodiments, fungi are dewatered and separated via belt press. In certain embodiments fungi are dewatered and separated via vacuum/pressure filter. In certain embodiments fungi are dewatered via a fluidized bed dryer. In certain embodiments, the filamentous fungi are washed to remove excess growth medium. In certain embodiments, the filamentous fungi are not washed.

In certain embodiments, the harvested filamentous fungal biomass is processed for further use. The processing technique can be any processing technique apparent to the practitioner of skill.

In certain embodiments, hydrolysis and starch conversion process of plant material is accelerated by using a protease, β-glucanase, xylanase, α-amylase and/or other enzymes during the hydrolysis step of generating the substrate of the aerobic fermentation.

In certain embodiments, an alkali or acid treatment is used in the hydrolysis of the plant material used as substrate.

In certain embodiments, the filamentous fungi are sized according to the requirements of the ingredients described herein. Biomass released from de-watering processes can be cake-like as it is similar to fruit, paper, or other pulp upon de-watering. This cake can be broken apart, shredded, chopped, sliced, diced, sieved, and further reduced to desired size using conventional sizing equipment before or after de-hydration. The biomass can be molded, pressed, rolled, extruded, compacted, or manipulated in other ways known to a person with skill in the art of sizing food materials. This can happen before de-watering, during, de-watering, after de-watering, before de-hydration, during de-hydration, or after de-hydration. In certain embodiments, the biomass is sized to yield particles of sizes described below.

In certain embodiments, the biomass slurry comprises highly dispersed filamentous cell structures. Upon removing water using gravity, pressure, compaction, vacuum suction, centrifugation, or other methods known to those skilled in the art of de-watering, filamentous cellular strands interlock with each other to form cohesive filamentous mats that maintain consistency and cohesion. A belt press can be particularly useful in producing large meaty slabs of dense cohesive biomass. These dense mats can be sliced, diced, chopped, molded, folded, extruded, or otherwise manipulated in a way known to a person with skill in the art to form slices, chunks, shreds, nuggets, or other particles and pieces.

In certain embodiments the biomass described herein is extruded using high temperature twin screw extrusion or other extrusion technology to form a material with a more conventional texture that is similar to TVP.

In certain embodiments the biomass of the fermentation process is de-watered to remove moisture from the biomass. The material is optionally pasteurized in the substrate by using steam to heat the biomass slurry to pasteurization temperatures (75-85° C.); the slurry is optionally released into a vibratory screen to de-water the material down to 75-95% water content; the biomass is then optionally pressed with a belt press, screw press, vacuum/pressure filter, or centrifuged to further reduce the water content; the material is then optionally shredded, sized, compacted, molded, otherwise formed, or combinations thereof; the material is then optionally added to a conveyer, or rotary drum, dryer for full dehydration. In particular embodiments, the material is de-watered to yield a water content for the particles as described below.

In certain embodiments, the biomass slurry containing 1-8% biomass is harvested and dewatered by releasing into a belt press or a vacuum/pressure system. The material is simultaneously drained and compressed bringing the material down to 60-85% water content. The machine is adjusted to release a cake/slab at a thickness of 1-2 inch/2.54-5.8 cm. In some embodiments, the cake/slab can be continuously conveyed into a mechanical shredder. The shredder releases granular particles in the size range of about 1 mm-about 50 mm. In some embodiments, particles are continuously sieved using 2 mm and 12 mm sieves. In certain embodiments, particles released through the 2 mm sieve are saved and de-hydrated separately or re-introduced to the initial slurry. In some embodiments, particles released through the 12 mm sieve but not through the 2 mm sieve are fed directly into a conveyer, rotary drum, or fluidized bed dryer for dehydration and optionally heat pasteurization. In some embodiments, particles larger than 12 mm are optionally conveyed back through the shredder for further size reduction. The dehydrated particles between about 2 and about 50 mm are ready for use as a bare ingredient or to be further processed into ingredients described herein. As used herein, the term "about" indicates a reasonable range above and below a unit value, for instance +/−10% or +/1 unit, e.g. mm.

In certain embodiments the biomass slurry is de-watered down to 50-80% water content with methods known to a person with skill in the art of de-watering microbial biomass. The lower moisture biomass at 50-80% water content is then fed through a dough chopping machine. Material is fed through a ¼ inch die and chopped into small particles intermittently by a rotating shear at the end of the die. This results in chunks of a consistent size of about (⅛ inch to ¼ inch) by (⅛ inch to ¼ inch) by (⅛ inch to ¼ inch).

In certain embodiments plant or mushroom materials are added to the biomass prior to de-hydration. These materials can be added to the fungal biomass slurry, the fungal biomass with a water content of 60-85%, the fungal biomass of a water content of 60-80%, the fungal biomass of a water content of 50-80%, the fungal biomass of a water content of 50-65%, or fungal biomass with other water content. These materials may be blended with the fungal biomass described herein and then further de-watered, de-hydrated, or processed into the dried textured ingredients described herein.

In another embodiment supernatant of the fermentation process containing high concentrations of digestive enzymes such as alpha amylase, beta amylase, lipase, and others is processed into side streams. These enzymes can be extracted, purified, and sold or used in pretreatment of hydrolyzed starch rich substrates or in other applications. These enzymes from the supernatant can be integrated into the meat analogues and blends described herein to promote more effective digestion.

Growth Medium

The growth medium can be any growth medium deemed suitable. In particular embodiments, the growth medium comprises plant biomass. In certain embodiments, the plant biomass is a wastewater stream. The plant biomass co-products, ingredients, and wastewater streams can be any material stream deemed suitable to the practitioner of skill in the art. In particular embodiments, the plant biomass is from a low-cost source. In certain embodiments, the plant biomass is a waste stream or a co-product from another food, agriculture, or plant processing process. In such embodiments, the methods provide a second or renewable use of co-products that are conventionally used as farm animal feed, soil enhancement, or discarded entirely. In certain embodiments, the material is selected from ethanol thin stillage, ethanol co-products, rice milling co-products, rice polishings, rice bran, rice process waste water, rice brokens, brewing and distilling spent grains, spent sake rice, spent soy sauce soy, beet pulp, coffee chaff, molasses, sugar refinery waste water, grape pulp, soda production waste water, sugarcane bagasse, sorghum bagasse, or combinations thereof. In preferred embodiments the nutrient streams are potato processing waste-water, ethanol corn stillage.

In certain embodiments, the methods comprise fermenting plant ingredients in submerged culture to create cultured plant ingredients that contain a significant concentration of fungal biomass.

In some embodiments, the growth medium comprises one or more plant substrates selected from potato solids, potato starch, potato protein, pea fiber, other plant fibers, gum arabic, natural flavors, soy protein, wheat starch, wheat protein, pea protein, corn protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, rice protein, fermented rice extract, corn starch, kombu extract, algae, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract, seaweed, malted barley, malt extract, yeast extract, whole cell yeast, lentils, black beans, pinto beans, beans, legumes, and any combination thereof. In preferred embodiments, the plant biomass is potato solids or corn stillage.

As used herein, the term "potato solids" refers to potatoes that comprise about 0% up to about 60% of the peel, or about 10% to about 55% of the peel, or about 20% to about 40% of the peel, and a water content of about 55% to about 85% and are essentially made of raw potatoes. Potato solids can also be rejects from potato processing manufacturing such as semi prepped or final French fries, hash browns, mashed potatoes, grated potatoes formed into shapes or chips. Furthermore, they may contain residual processing components such as oil, maltodextrin, trisodium phosphate, proteins, cellulose derivatives, alginates, pectins, and starches.

In some embodiments, potato solids are comminuted using a high-shear in-line mixer, a mixer-homogenizer or other mixing device known to one skilled in the art of comminution. In some embodiments, comminuted potato solids generally are reduced in size to a mean particle size that is less than about 1250 µm, less than about 1000 µm, less than about 900 µm, less than about 800 µm, less than about 700 µm, less than about 600 µm, less than about 500 µm, less than about 400 µm, less than about 300 µm, less than about 250 µm, less than about 200 µm, less than about 150 µm, less than about 100 µm, less than about 50 µm, less than about 25 µm, or less than about 20 µm. In certain embodiments, comminuted potato solids have a mean particle size that is about 200 µm to about 100 µm, about 100 µm to about 50 µm, or about 50 µm to about 20 µm.

In certain embodiments, supplements can be added to the potato solids. For example, supplements can include, but are not limited to trace-elements (for example, magnesium, citrate, phosphate, potassium, calcium, zinc, iron, copper, manganese, molybdate, nickel, borate, cobaltous, biotin, thiamine, inositol, and pyridoxine), yeast extracts, different varieties of peptones, nitrogen salts (ammonium and nitrate salts), phosphorus salts, magnesium salts, potassium salts, monosaccharides, complex carbohydrates, plant extracts and syrups, vitamins, and other nutrients. Other nutrients are selected from nitrogen sources (inorganic, ammonium, nitrate, urea, corn protein, soy protein, or potato protein), peptones, syrups, sugars, vitamins, and trace elements. In some embodiments, the potato slurry is combined with inorganic nitrogen sources or organic nitrogen sources. In certain embodiments, it can be combined with other nutrients to enhance the fermentation or final product properties (for example, biotin and thiamin can improve growth and protein production if levels in the potato are too low (biotin is an essential B vitamin that cannot be synthesized by some fungi), peptones can be added as a nitrogen source and base amino acid source, B12 can be added to facilitate higher B12 levels and trace elements can improve biomass yield).

In some embodiments, the wet mass produced from dewatered fermentation slurry is manipulated into a dry, shelf-stable particle that can be re-hydrated and used as an ingredient in meat analog and meat extension applications. This dry shelf-stable particle can be dried to about 10%, about 9%, about 8%, about 7%, about 6%, about 5%, about 4%, or about 3%, water content and can be packaged, shipped, and stored as needed without a cold-chain. These particles range in size from about 6 mm to about 15 mm, about 6 mm to about 10 mm, about 6 mm to about 50 mm, about 10 mm to about 20 mm, about 20 mm to about 30 mm, or about 7 mm.

In some embodiments, the wet fungal biomass at about 60% to about 80% water content is chopped, sliced, shaped, molded, or otherwise manipulated to create different product shapes. The material can be manipulated in a variety of ways to take the form required for any meat-like product.

In certain embodiments, the growth medium is supplemented with one or more additive components. The additive components might facilitate growth of the filamentous fungi, they might add nutrients to the resulting food product, or they might do both. In certain embodiments, the additive components comprise one or more carbohydrates (simple and/or complex), nitrogen, vitamins, minerals, fats, proteins, or a combination thereof.

In certain embodiments, the additive components comprise one or more oils.

In certain embodiments, the one or more oils are selected from the group consisting of grapeseed oil, safflower oil, sunflower oil, olive oil, coconut oil, flaxseed oil, avocado oil, soybean oil, palm oil, canola oil, and combinations thereof.

In certain embodiments, the one or more additives comprise one or more salts. In certain embodiments, the one or more salts consist of elements selected from the group consisting of C, Zn, Co, Mg, K, Fe, Cu, Na, Mo, S, N, P, Ca, Cl, and combinations thereof.

In certain embodiments the salts comprise one or more of the following salts: ammonium nitrate, mono-potassium phosphate, di-potassium phosphate, di-ammonium phosphate, ammonium phosphate, potassium nitrate, magnesium sulfate heptahydrate, calcium chloride dehydrate, zinc sulfate heptahydrate, iron sulfate hexahydrate, copper sulfate pentahydrate, manganese sulfate, and combinations thereof.

In certain embodiments, the growth medium comprises one or more carbohydrates. In certain embodiments the one or more carbohydrates are selected from glucose, sucrose, starch, maltose, and any combination thereof.

In certain embodiments, the growth medium comprises plant oils. The plant oils can significantly increase yields, fermentation efficiency, and fat content of the end material. Non-limiting examples of plant oils can include almond oil, avocado seed oil, cocoa butter, coconut oil, corn oil, cottonseed oil, flax seed oil, grapeseed oil, hemp oil, olive oil, palm kernel oil, peanut oil, pumpkin seed oil, rice bran oil, safflower seed oil, sesame seed oil, sunflower seed oil, soybean oil, or walnut oil.

In certain embodiments, the growth medium comprises vitamins. Useful vitamins include but are not limited to vitamin A, B1, B2, B3, B5, B6, B7 (vitamin H, or Biotin), B9, B12, C, E, D, and K, for the purpose of integrating the vitamin into the end food product via adsorption and cellular integration in the fermentation. In an embodiment, vitamin B12 is added to the fermentation.

In certain embodiments, vitamin B12 is added to the substrate. The vitamin is accumulated by the fungal cells. It is the only B vitamin essential to the human diet that the fungus does not produce on its own.

In certain embodiments the plant-derived biomass or material is added to the growth medium without hydrolysis.

In certain embodiments, the growth medium comprises spent malted barley.

The spent malted barley can be used as a plant biomass for hydrolysis, filtration and integration into the substrate as a primary source of carbohydrates, fats, proteins, and micronutrients.

In certain embodiments, the growth medium comprises potato peel. The potato peel can be used as a plant biomass for the hydrolysis, filtration and integration into the substrate as a source of carbohydrates, fats, and micronutrients.

In certain embodiments, the growth medium comprises potato processing wastewater. The potato processing wastewater can be used as a primary nutrient source for the fermentation of the fungi. Blanching, starch extraction and other processing methods used for potato processing produce large volumes of nutritionally consistent waste water that is highly effective as a fermentation feedstock.

In certain embodiments waste-water from potato blanching is used as substrate promptly after blanching. The high temperature of the blanching process pasteurizes the substrate, effectively reducing treatment costs in addition to substrate costs. In some embodiments other blanche water and other clean potato processing streams are diverted away from field leaching, conventional treatment methods, and other disposal methods towards the platform described herein.

In certain embodiments, the growth medium comprises beet pulp. The beet pulp can be used as a plant biomass for the hydrolysis, filtration and integration into the substrate as a primary source of carbohydrates, micronutrients, and nitrogen.

In certain embodiments, the growth medium comprises thin stillage (a co-product of biofuel production with corn). The thin stillage can be used as a complex nutrient source of carbon, nitrogen, micronutrients, and fats.

In certain embodiments, the growth medium comprises corn steep liquor (a co-product of corn milling). The liqueur can be used as a complex nutrient source of carbon, nitrogen, micronutrients, and fats.

In certain embodiments, the growth medium comprises insoluble corn protein or "corn gluten" (a co-product of corn milling). The corn protein can be used as a complex nutrient source of carbon, nitrogen, micronutrients, and fats.

In certain embodiments, the growth medium comprises yeast extract. The yeast extract can be used as a source of nitrogen and micronutrients in the fermentation media.

In certain embodiments, the growth medium comprises filtered beet pulp extract. The filtered beet pulp extract can be used for the primary carbon source.

In certain embodiments, the growth medium comprises potato blanch and processing wastewater. The potato blanch and processing wastewater can be used for the primary nutrient source.

In certain embodiments, the growth medium comprises rice polishings. Rice polishings can be left over from polishing and/or milling rice. They can be used as a plant biomass and added to water, sterilized, and integrated into the reactor as a primary source of carbohydrates, nitrogen, potassium, and other nutrients.

In certain embodiments, the growth medium comprises common carbohydrate sources such as sucrose, glucose, and molasses. They can be used with supplementation for the substrate. These ingredients can be blended, sterilized, and integrated into the reactor with filamentous fungi described herein. The produced biomass can be processed into the versatile dried ingredients described herein.

Fermentation Methods to Produce Wet and Dry Fungal Potato Product

Mycelial potato products of the present disclosure were produced by fermenting fresh solid materials with *N. intermedia, N. crassa* or *A. oryzae*. Optimized potato substrate (herein identified as "MP+"), developed in the current work, was prepared from potato solid rejects that are comminuted in water using a food processor, high-shear in-line mixer, and/or mixer-homogenizer. The comminuted potato solids are then supplemented with inorganic nitrogen, for example about 0.8 g/l of diammonium sulfate and about 1.2 g/l potassium nitrate. Potato solids are adjusted to about 50 g of dry potato solids matter per liter of liquid media using water. The MP+ media is gelatinized and sterilized in an autoclave, steam pressure, or continuous pasteurizer by heating to 120° C. for >15 minutes. In certain embodiments, hydrolyzing enzymes (e.g, amylases) can be added prior to heating in order to improve the breakdown and consumption of the potato starch.

For small-scale experiments, media was added to up to 2 L in a 2.8 L Fernbach flask. Media was inoculated with conidia of *N. intermedia*. Alternatively, pre-cultured *N. intermedia* mycelium can be used to inoculate flasks at 2% of the volume. Yet, alternatively, essentially the same method is used to inoculate with *N. crassa* or *A. oryzae*. Flasks are then incubated at 30° C. with 200 RPM in a shaking incubator.

To generate larger amounts of product to produce meat analogs and blends, and for manufacturing, a bioreactor is used. Custom-designed and assembled bioreactors can also be used, for example, with working volumes of about 5 L to about 25 L, or larger. The bioreactor is filled with pre-sterilized MP+. Alternatively, the bioreactor is filled and sterilized in place using steam pressure. The media is inoculated with fungal conidia to about $10^5$ spores/ml. The bioreactor is operated at 0.5-2 VVM during the fermentation and temperature is controlled at 30° C. using a heating element, blanket or steam injected into the jacket of the bioreactor. After about 48 hours of growth, the biomass is harvested in a batch mode. The bioreactor can also be operated at fed-batch mode or with a drain-fill cycle. In the latter case, the biomass is drained to retain 10%-20% of the volume before loading the bioreactor with a fresh batch of MP+ and repeating a 48 hour cultivation. At pilot and production scales, a continuous mode can be employed to reduce down time and improve the efficiency of operations.

Fungal biomass is harvested and dewatered with methods known to those skilled in the art of dewatering microbes. In the case of producing dry food ingredients (DM401), the wet cake is shredded and dehydrated at 60° C. for >5 hours. Fermented potato biomass, wet or dry, is pasteurized by steam heating or dry heating before incorporating into food products.

Filamentous Fungi

The filamentous fungi can be any filamentous fungi deemed suitable to the person of skill in the art.

In certain embodiments, at least one fungus is from the kingdom of Fungi.

In certain embodiments, at least one fungus is from the phylum Basidiomycota, Ascomycota, Glomeromycota, Mucoromycota, or Zoopagomycota.

In certain embodiments, at least one fungus is from the division agaricomycotina, ustilagomycotina, pezizomycotina, saccharomycotina, taphrinomycetes, diversisporalis, archaeosporales, paraglomerales, endogonales, mucorales, mortieralles, entomophthoromycotina, asellariales, kickxellales, dimargaritales, harpellales, zoopagomycotina, or combinations thereof.

In certain embodiments, at least one fungus is from the class tremellomycetes, dacrymycetes, agaricomycetes, exobasisiomycetes, ustilaginomycetes, malasseziomycetes, moniliellomycetes, arthoniomycetes, coniocybomycetes, dothideomycetes, eurotiomyctes, geoglossomycetes, laboulbeniomycetes, lecanoromycetes, leotiomycetes, lichinomycetes, orbiliomycetes, pezizomycetes, sordariomycetes, xylonomycetes, or combinations thereof.

In certain embodiments, at least one fungus is from the order filobasidiales, agaricales, amylocorticiales, atheliales, boletales, jaapiales, lepidostromatales, geastrales, gomphales, hysterangiales, phallales, auriculariales, cantherellales, corticiales, gleophylalles, hymenochaetales, polyporales, russulales, sebacinales, stereopsidales, thelephorales, trechisporales, ceraceosorales, doassansiales, entyomatales, exobasidiales, georgefischeriales, microstromatales, tilletiales, urocystales, ustilaginales, malasseziozioales, moniliellales, saccharomycetales, coronophorales, glomeralles, Hypocreales, melanosporales, microascales, boliniales, calosphaeriales, chaetospheriales, coniochaetales, diasporthales, magnaporthales, ophiostomatales, sordariales, xylariales, koralionastetales, lulworthiales, meliolales, phylachoralles, trichosphariales, eurotiales, chaetothyriales, pyrenulales, verrucariales, onygenales, mortierellales, mucorales, endogonales, or combinations thereof.

In certain embodiments, at least one fungus is from the family Filobasidium, Dacromycetaceae, Agaricaceae, Amanitaceae, Bolbitiaceae, Broomeiceae, Chromocyphellaceae, Clavariaceae, Cortinariaceae, Cyphellaceae, Enolomataceae, Fistulinaceae, Himigasteraceae, Hydnangiaceae, Hygrophoraceae, Inocybaceae, Limnoperdacea, Lyophyllaceae, Marasmiaceae, Mycenacea, Niaceae, Pellorinaceae, Physalacriaceae, Pleurotacea, Pluteaceae, Porotheleaceae, Psathyrellaceae, Pterulacea, Schizophyllaceae, Stephanosporaceae, Strophariaceae, Tricholomataceae, Typhulaceae, Boletaceae, Boletinellaceae, Coniophoraceae, Diplocystaceae, Gasterellaceae, Gastrosporiaceae, Gomphidiaceae, Gyroporaceae, Hygrophoropsidaceae, Paxillaceae, Protogastraceae, Rhizopogonaceae, Sclerodermataceae, Serpulaceae, Suillaceae, Tapinellaceae, Hymenochaetaceae, Repetobasidiaceae, Schizoporaceae, Cystostereaceae, Fomitopsidaceae, Fragiporiaceae, Ganodermataceae, Gelatoporaceae, Meripilaceae, Merulaciaea, Phenerochaetaceae, Polyporaceae, Sparassidaceae, Steccherinaceae, Xenasmataceae, Albatrellaceae, Amylostereaceae, Auriscalpaceae, Bondarzewiaceae, Echinodontiaceae, Hericiaceae, Hybogasteraceae, Lachnocladiaceae, Peniphoraceae, Russulaceae, Gloeocyctidiellacceae, Stereaceae, Ustilaginomycetes, Saccharomycetaceae, Saccharomycodaceae, Saccharomycopsidaceae, Chaetomiaceae, Lasiosphaeriaceae, Sordariaceae, or combinations thereof.

In certain embodiments, at least one fungus is from the genus *Neurospora, Aspergillus, Trichoderma, Pleurotus, Ganoderma, Inonotus, Cordyceps, Ustilago, Rhizopus, Tuber, Fusarium, Pennicillium, Xylaria, Trametes*, or combinations thereof.

In certain embodiments, at least one fungus is *Aspergillus oryzae, Rhizopus oryzae, Fusarium graminareum, Cordyceps militaris, Cordyceps sinensis, Tuber melanosporum, Tuber magnatum, Pennicillium camemberti, Neurospora crassa, Neurospora intermedia, Neurospora sitophila, Xylaria hypoxion*, or a combination thereof.

Exemplary Methods

In this section, illustrative methods are provided. They are intended to exemplify but not limit the methods described above.

In certain embodiments, plant material is incubated with an enzyme. For example, with about 0.1-1.5 g/kg alpha-amylase, or about 0.02-1.0 g/kg beta-amylase, or about 0.1-1.25 g/kg beta-glucanase, or about 0.01-1.0 g/kg protease, or about 0.01-1.0 g/kg xylanase (grams of purified enzyme to kilograms of desiccated substrate). The incubation temperature is increased to about 78° C.-110° C. to activate the enzymes, dissolve the starch and initiate the hydrolyzing functions. The temperature is maintained for about 30-120 minutes to complete the hydrolysis. The quantities of enzymes, their weights, temperatures, interaction times and their ratios can change based on the plant material being hydrolyzed and specification of the enzyme or to optimize the effect of the enzyme.

In certain embodiments, the solid plant-based ingredients are blended into room temperature water. The slurry is pumped through a continuous steam sterilizer and injected into the fermentation reactor described herein at the desired flow rate for the method of fermentation being run. In some embodiments, the slurry is pumped at the maximum rate of sterilization to fill a sterile fermenter for the primary initiation of a batch style fermentation. In some embodiments the slurry is injected in pulses aligning with the extraction of biomass slurry described herein. In some embodiments, the slurries are injected continuously.

In some embodiments, the solid plant-based ingredients are sterilized with standard techniques, known to someone with skill in the art of sterile processes, and introduced to the fermentations of the present disclosure.

In some embodiments, starch rich processing wastewater from potato blanching, steaming, and/or general processing used as the primary substrate of the fermentation. In some embodiments it is steam sterilized in a continuous media sterilizer. The material may or may not be pre-heated from the potato processing providing energetic efficiency advantages. This material may constitute 100% of the growth media described herein. This material may constitute less than 100% of growth media. In some embodiments the wastewater is supplemented with biotin. In some embodiments this material is supplemented with ammonium gas. In some embodiments, this material is supplemented with di-ammonium phosphate. In some embodiments, this material is supplemented with ammonium nitrate. In some embodiments, this material is supplemented with yeast extract. In some embodiments this material is supplemented with potassium nitrate. In some embodiments, this material is supplemented with potassium phosphate. In some embodiments this material is supplemented with calcium chloride. In some embodiments this material is supplemented with magnesium sulfate. In some embodiments this material is supplemented with nitrates. In some embodiments this material is supplemented with ammonium salts. In some embodiments this material is supplemented with the aforementioned plant ingredients described herein. In some embodiments the material is supplemented with aforementioned waste streams or co-products described herein.

In some embodiments the potato processing wastewater chemical oxygen demand (COD) concentration measures between about 500 mg/l and about 300,000 mg/l, between about 2,000 mg/l and about 200,000 mg/l, between about 2,000 mg/l and about 100,000 mg/l, between about 2,000 mg/l and about 50,000 mg/l, between about 2,500 mg/l and about 25,000 mg/l, or between about 2,000 mg/l and about 10,000 mg/l.

In certain embodiments, corn stillage is captured, optionally sterilized, optionally supplemented, and injected into the bioreactors running the fermentations of the present disclosure. Thin stillage that can be used has an average of 85,000 mg/l COD and about 5,000 mg/l of total nitrogen. This material may constitute 100% of the growth media described herein. This material may constitute less than 100% of growth media. In some embodiments the wastewater is supplemented with biotin. In some embodiments this material is supplemented with ammonium gas. In some embodiments this material is supplemented with di-ammonium phosphate. In some embodiments this material is supplemented with ammonium nitrate. In some embodiments this material is supplemented with yeast extract. In some embodiments this material is supplemented with potassium nitrate. In some embodiments this material is supplemented with potassium phosphate. In some embodiments this material is supplemented with calcium chloride. In some embodiments this material is supplemented with magnesium sulfate. In some embodiments this material is supplemented with nitrates. In some embodiments this material is supplemented with ammonium salts. In some embodiments this material is supplemented with the aforementioned plant ingredients described herein. In some embodiments the material is supplemented with aforementioned waste streams or co-products described herein.

Shelf-Stable Food Ingredient

In another aspect, provided herein are shelf-stable protein food ingredients. The shelf-stable protein food ingredients comprise cultured fungal biomass and a limited amount of water. The shelf-stable protein food ingredients can be prepared according to the methods above. The shelf-stable food ingredients are designed to be a versatile, primarily textured, consistent sized material that is dry, storable, and optimized for ease of use in an end product. Provided herein are exemplary detailed characterizations of the shelf stable protein food ingredients provided herein.

Texture: Texture of the ingredient is important when being used as a meat analogue or a meat extension agent. The filamentous nature of the fungi described herein provides compacted and aligned fibers that mimic muscle in some ways. Texture was analyzed using a rheometer with a 25 mm diameter cylinder probe. The TCP was hydrated for 30 mins at a 1/1.75 w/w ratio of TCP/water. The cross head speed was set to 100 mm/min$^{-1}$ with a max peak stress of 10 kg and a distance between the two supports of 13 mm. The results were averages of 20 treatments.

Chewiness: Chewiness was analyzed using the described methods in "Breene W M, Application of texture profile analysis to instrumental food texture evaluation. *J Texture Stud* 6:53-82 (1975)" using hydrated TCP of the present disclosure. Chewiness was typically between about 0.5 kg and about 15 kg, between about 1 kg and about 12 kg, between about 2 kg and about 10 kg, or between about 4 kg and about 8 kg.

Cohesiveness: Cohesiveness was determined by taking the dry shelf-stable ingredient of the present disclosure, hydrating it at a 1/1.75 ratio w/w of dry product to water, treating the material with the following process, and analyzing texture residues. After hydration, the material was subsequently pressurized, dispersed, and dried. Cohesiveness was typically between about 20% and about 90%, between about 30% and about 80%, or between about 40% and about 60%.

Springiness: Springiness was analyzed using the described methods in "Breene W M, Application of texture profile analysis to instrumental food texture evaluation. *J Texture Stud* 6:53-82 (1975)" using hydrated TCP of the present disclosure. Springiness was typically between about 15% and about 99%, between about 20% and about 85%, between about 40% and about 70%, or between about 40% and about 60%.

Transversal cutting strength: Cutting strength was determined by using a cutting probe (7.5 mm×38.3 mm) with a 2 kg maximum peak stress. Cutting strength helps with determining bite resistance, shear, and texture as it relates to maceration in the human mouth.

Longitudinal cutting strength: Cutting strength was determined by the same methods used for the transversal cutting strength tests.

Protein: The protein content of the ingredients described herein comprise at least 5% total protein. In certain embodiments, the shelf-stable protein food ingredients comprise protein in an w/w amount of 5-100%, 5-75%, 5-50%, 5-45%, 5-40%, 5-35%, 5-30%, 5-25%, 5-20%, or 5-15%. The amino acid profile may comprise of a number of amino acids. Total protein content of an ingredient can be determined by many different methods including but not limited to AOAC International methods 990.03 and 992.15. In some embodiments the ingredient contains the amino acids Methionine, Cystine, Lysine, Phenylalanine, Leucine, Isoleucine, Threonine, Valine, Histidine, Arginine, Glycine, Aspartic acid, Serine, Glutamic acid, Proline, Hydroxyproline, Alanine, Tyrosine, and Tryptophan, Taurine, and others. The ingredient contains all of the essential amino acids for the human diet.

Fat: The fat composition of the ingredient described herein comprises mostly mono- and polyunsaturated fats and can be very low in saturated fats. In some embodiments the total fat content comprises a w/w amount between about 1% and about 80%, between about 1% and about 70%, between about 1% and about 60%, between about 1% and about 50%, between about 2% and about 40%, between about 3% and about 30%, between about 5% and about 30%, between about 6% and about 20%, between about 7% and about 15%, between about 8% and 13%, between about 10% and about 14% by weight of total fat. Fats are primarily monounsaturated and polyunsaturated fats. In some embodiments saturated fats are between 0% and about 40%, between 0% and about 30%, between about 5% and about 20%, and between about 10% and about 20% of the total fat content. In some embodiments unsaturated fats are between about 10% and about 100%, between about 20% and about 100%, between about 30% and about 100%, between about 40% and about 100%, between about 60% and about 90%, or between about 70% and about 80% of the total fat content.

Fiber: In certain embodiments, the shelf-stable protein food ingredients described herein are naturally high in fiber. This can be positive aspect of this type of meat like product. AOAC method 991.43 can be used to determine the fiber content of the ingredients described herein. In some embodiments, fiber content is between about 5% and about 60%, between about 10% and about 50%, between about 15% and about 40%, between about 20% and about 40%, or between about 30% and about 40%.

Vitamins: In certain embodiments, the shelf-stable protein food ingredients comprise a range of water-soluble B vitamins sometimes consisting of thiamin, riboflavin, niacin, pyridoxine, pantothenic acid, folic acid, biotin, and others.

Minerals: In certain embodiments, the shelf-stable protein food ingredients comprise calcium, phosphorous, magnesium, iron, zinc, sodium, manganese and potassium. Calcium is typically in an amount of 200 mg/kg or more. In some embodiments, calcium is between about 500 mg/kg and about 3000 mg/kg, between about 1000 mg/kg and about 2500 mg/kg, between about 1250 mg/kg and about 2000 mg/kg, and between about 1500 mg/kg and 2000 mg/kg. Phosphorous is typically in an amount of 200 mg/kg or more In some embodiments phosphorous is between about 500 mg/kg and about 2500 mg/kg, between about 500 mg/kg and about 2000 mg/kg, between about 750 mg/kg and about 1500 mg/kg, and between about 800 mg/kg and 1200 mg/kg. Potassium is typically in an amount of 100 mg/kg or more. In some embodiments, potassium is between about 1000 mg/kg and about 8000 mg/kg, between about 2000 mg/kg and about 6000 mg/kg, between about 2500 mg/kg and about 5000 mg/kg, and between about 3000 mg/kg and 4500 mg/kg. Sodium is in an amount of 20 mg/kg or more. In some embodiments sodium is between about 20 mg/kg and about 1500 mg/kg, between about 50 mg/kg and about 400 mg/kg, between about 100 mg/kg and about 300 mg/kg, between about 150 mg/kg and about 250 mg/kg, between about 175 mg/kg and about 225 mg/kg. Magnesium is in an amount of 200 mg/kg or more. In some embodiments, magnesium is between about 500 mg/kg and about 3000 mg/kg, between about 1000 mg/kg and about 2500 mg/kg, between about 1250 mg/kg and about 2000 mg/kg, and between about 1500 mg/kg and about 2000 mg/kg. Iron is typically in an amount of 1 mg/kg or more. In some embodiments iron is between about 2 mg/kg and about 100 mg/kg, between about 5 mg/kg and about 80 mg/kg, between about 10 mg/kg and about 50 mg/kg, or between about 20 mg/kg and 40 mg/kg. Zinc is in an amount of 20 mg/kg or more. In some embodiments zinc is between about 20 mg/kg and about 1500 mg/kg, between about 100 mg/kg and about 600 mg/kg, between about 200 mg/kg and about 500 mg/kg, between about 300 mg/kg and about 500 mg/kg, between about 350 mg/kg and about 450 mg/kg.

Water holding capacity (WHC): In certain embodiments, the shelf-stable protein food ingredients described herein has a WHC significantly higher than that of traditional TVP, that of meat, and that of plant ingredients. WHC is analyzed by fully removing all moisture from the ingredient, weighing the ingredient, then fully hydrating the ingredient, then removing surface moisture, then weighing again. All samples are analyzed in quadruplicate and the average is taken. WHC of the TCP was recorded as being as high as 6,743 g/kg. In preferred embodiments, the WHC of the TCP ingredient is between about 2,000 g/kg and about 7,000 g/kg. In some embodiments the WHC is between about 2,000 g/kg and about 6,000 g/kg, between about 2,000 g/kg and about 5,000 g/kg, between about 3,000 g/kg and about 5,000 g/kg, between about 3,500 g/kg and about 4,500 g/kg, or between about 4,000 g/kg and about 5,000 g/kg.

Particle size: In certain embodiments, the shelf-stable protein food ingredients are manipulated during the processing of the ingredient to have specific particle sizes. Certain particle sizes work best for certain applications. Particle sizes usually range from a fine powder to 1000 cm sheets. In certain embodiments the particle size is between about 2 mm and about 40 mm, between about 2 mm and about 30 mm, between about 2 mm and about 20 mm, between about 2 mm and about 15 mm, between about 2 mm and about 10 mm, between about 2 mm and about 8 mm, between about 2 mm and about 6 mm, between about 3 mm and about 10 mm, between about 3 mm and about 7 mm, between about 4 mm and about 6 mm, between about 4 mm and about 10 mm, between about 5 mm and about 50 mm, between about 5 mm and about 40 mm, between about 5 mm and about 20 mm, between about 5 mm and about 10 mm, between about 6 mm and about 50 mm, between about 6 mm and about 40 mm, between about 6 mm and about 30 mm, between about 6 mm and about 20 mm, between about 6 mm and about 10 mm, between 6 mm and about 10 mm, between about 7 mm and about 20 mm, between about 7 mm and about 15 mm, between about 7 mm and about 12 mm, between about 7 mm and about 10 mm. In preferred embodiments the particles are 3 mm, 4 mm, 5 mm, 6 mm, 7 mm, 8 mm, 9 mm, 10 mm, 11 mm, and 12 mm.

In some embodiments the particle size is measured with "D-values". D10, D50, and D90 represent the percentage of particles less than a certain sieve size (10%, 50%, and 90% respectively). In particular, D10 indicates a diameter at which 10% of the mass of a sample is in particles less than the indicated diameter. D50 indicates a diameter at which 50% of the mass of a sample is in particles less than the indicated diameter. D90 indicates a diameter at which 90% of the mass of a sample is in particles less than the indicated diameter. In certain embodiments the TCP described herein has a D50 of about 5 mm, a D50 of about 6 mm, a D50 of about 7 mm, a D50 of about 4 mm, a D50 of about 8 mm, a D50 of about 9 mm, a D50 of about 10 mm, a D50 of about 11 mm, a D50 of about 15 mm, a D10 of about 2 mm, a D10 of about 3 mm, a D10 of about 4 mm, a D10 of about 5 mm, a D10 of about 6 mm, a D10 of about 7 mm, a D10 of about 8 mm, a D10 of about 9 m, a D10 of about 10 mm, a D10 of about 11 mm, a D10 of about 12 mm, a D90 of about 2 mm, a D90 of about 50 mesh, a D90 of about 70 mesh, a D90 of about 100 mesh, a D90 of about 1 mm, a D90 of about 2 mm, a D90 of about 3 mm, a D90 of about 4 mm, a D90 of about 5 mm, a D90 of about 6 mm, a D90 of about 7 mm, a D90 of about 8 mm, or a D90 of about 9 mm.

In certain embodiments, the term "about" indicates +/−1 mm. In certain embodiments, the D10, D50, and D90 values are exact, or exact within the tolerance range of the measurement technique. Particle size can be measured according to standard techniques, for instance sieve analysis.

Color: In certain embodiments, the shelf-stable protein food ingredients have a naturally white/off white color. In certain embodiments, the shelf-stable protein food ingredients have an off-white consistent color. In certain embodiments, the shelf-stable protein food ingredients have a tan color. In some embodiments, the material is affected by aforementioned substrate components. Sometimes this color is caramel, red, pink, green, brown, yellow, and other hues. In some embodiments, the color of the shelf-stable protein food ingredients described herein is affected by the plant ingredients that are sometimes combined with the mycelium. Sometimes this color is caramel, red, pink, green, brown, yellow, orange, and other hues.

In some embodiments described herein additional ingredients are integrated into the fermentation process and some concentrations of these additional ingredients remain in the dehydrated product described herein. These supplementary ingredients may alter the nutritional profile, texture, or other properties of the dry ingredients.

In some embodiments, additional ingredients are combined with the shelf-stable protein food ingredients described herein to form a complex ingredient with enhanced functional properties. The ingredients may be selected from the following: pea fiber, other plant fibers, gum arabic, natural flavors, texturized pea protein, texturized wheat protein, texturized soy protein, soy protein, wheat starch, wheat protein, pea protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, pea protein, rice protein, fermented rice extract, corn starch, potato starch, kombu extract, algae, potato protein, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract and seaweed, natural flavorings, or any combination thereof.

In some embodiments the ingredients described herein is combined with materials known to enhance texture, flavor, palatability, shelf life, stability, and other properties known to people with skill in the art of protein ingredients. These materials can be but are not limited to albumin, pectin, silicone dioxide, zinc gluconate, vitamin B12, maltodextrin, niacin, sodium ascorbate, pyridoxine hydrochloride, tetrasodium pyrophosphate, calcium carbonate, sodium alginate, alginate, trisodium phosphate, calcium acetate, methylcellulose, cellulose, bamboo cellulose, annatto, acetic acid, sodium nitrite, sodium benzoate, soy lecithin, or any combination thereof.

In certain embodiments the shelf-stable protein food ingredient described herein is milled into flour using conventional milling equipment. This flour provides the same nutritional profile aforementioned here while also having properties including but not limited to, gumming properties, tacking properties, enhanced nutrition, high fiber, dough like properties, and other flour like properties that lend themselves to being an effective flour replacement or enhancer. In some embodiments the aforementioned flour is combined with plant based flours such as corn flour, wheat flour, sorghum flour, rye flour, millet flour, *quinoa* flour, and other flours. In some embodiments the aforementioned flour is used in products like a protein bar, bread, pasta, and other flour containing food products.

In some embodiments plant or mushroom biomass is combined with the shelf-stable protein food ingredients described herein. The added properties of the plant/mushroom biomass enhances the product. Such enhancements are but are not limited to, color, texture, density, flavor, cooking properties, aesthetics, nutrition, etc. Such plants and mushrooms can be but are not limited to; beet root (*Beta vulgaris*), king oyster mushroom (*Pleurotus eryngii*), oyster mushroom (*Pleurotus ostreatus*), shiitake mushroom (*Lentinula edodes*), or portabello mushroom (*Agaricus bisporus*).

Food Products

In another aspect, provided herein are food products comprising the shelf-stable protein food ingredients. The food products comprise the shelf-stable protein food ingredients and one or more additional food ingredients. In certain embodiments, the shelf-stable protein food ingredients are mixed with fat, carbohydrate, meat, plant, or a combination thereof. In certain embodiments, the shelf-stable protein food ingredients are mixed with plant protein to form food products. In certain embodiments, the shelf-stable protein food ingredients are mixed with meat protein to form food products.

The meat can be any meat deemed suitable by the practitioner of skill. In certain embodiments, the meat is selected from the group consisting of beef, pork, chicken, turkey, lamb, fish, venison, bison, and combinations thereof. In certain embodiments, a shelf-stable protein food ingredient is mixed or layered with beef. In certain embodiments, a shelf-stable protein food ingredient is mixed or layered with pork. In certain embodiments, a shelf-stable protein food ingredient is mixed or layered with chicken. In certain embodiments, a shelf-stable protein food ingredient is mixed or layered with turkey. In certain embodiments, a shelf-stable protein food ingredient is mixed or layered with lamb. In certain embodiments, a shelf-stable protein food ingredient is mixed or layered with fish. In certain embodiments, a shelf-stable protein food ingredient is mixed or layered with crab. In certain embodiments, a shelf-stable protein food ingredient is mixed or layered with lobster. In certain embodiments, a shelf-stable protein food ingredient is mixed or layered with venison. In certain embodiments, a shelf-stable protein food ingredient is mixed or layered with bison.

In certain embodiments, the resulting composition is further mixed with any other food ingredient deemed suitable to the person of skill. In certain embodiments, the additional ingredient is selected from the group consisting of starches, oils, fats, grains, isolates, fibers, plants, algae, mushrooms, and combinations thereof. In certain embodiments, the additional ingredient is selected from the group consisting of pea fiber, other plant fibers, gum arabic, natural flavors, texturized pea protein, texturized wheat protein, texturized soy protein, soy protein, wheat starch, wheat protein, pea protein, spices, safflower oil, sunflower oil, olive oil, other oils, oat bran, oat flour, legumes, beans, lentils, lentil powder, bean powder, pea powder, yeast extract, nutritional yeast (immobilized dried yeast), molasses, honey, cane sugar, mushroom powder, white button mushroom powder, shiitake mushroom powder, chickpeas, bamboo fiber, cellulose, isolated oat product, isolated pea product, pea protein, rice protein, fermented rice extract, corn starch, potato starch, kombu extract, algae, potato protein, albumin, pectin, silicone dioxide, food starch, mixed tocopherols (vitamin E), coconut oil, sunflower oil, safflower oil, rapeseed oil, canola oil, dextrose, vegetable glycerin, dried yeast, citrus extract, citrus fiber, beet pulp, beet juice, beet juice extract, turmeric, mushroom extract, shiitake mushroom stems, shiitake mushrooms, white button mushrooms, tofu, soy fiber, soy hydrolysate, yeast extract and seaweed, natural flavorings, or any combination thereof.

Generally, the food products comprise fungal biomass in an amount of at least 5% w/w. The food products further comprise at least one meat in an amount of at least 10% w/w. In certain embodiments, when more than one meat is present the total amount of meat is at least 10% w/w. Advantageously, the food products can be prepared according to the methods above.

In certain embodiments, the food products comprise at least 5% w/w fungal biomass and at least 10% w/w meat. In certain embodiments, the food products comprise at least 5% w/w fungal biomass and at least 10% w/w meat. In certain embodiments, the food products comprise at least 10% w/w fungal biomass and at least 10% w/w meat. In certain embodiments, the food products comprise at least 15% w/w fungal biomass and at least 10% w/w meat. In certain embodiments, the food products comprise at least 20% w/w fungal biomass and at least 10% w/w meat. In certain embodiments, the food products comprise at least 10% w/w fungal biomass and at least 10% w/w meat. In certain embodiments, the food products comprise at least 25% w/w fungal biomass and at least 10% w/w meat. In certain embodiments, the food products comprise at least 30% w/w fungal biomass and at least 10% w/w meat. In certain embodiments, the food products comprise at least 35% w/w fungal biomass and at least 10% w/w meat. In certain embodiments, the food products comprise at least 40% w/w fungal biomass and at least 10% w/w meat. In certain embodiments, the food products comprise at least 45% w/w fungal biomass and at least 10% w/w meat. In certain embodiments, the food products comprise at least 50% w/w fungal biomass and at least 10% w/w meat.

In certain embodiments, the food products comprise at least 5% w/w fungal biomass and at least 20% w/w meat. In certain embodiments, the food products comprise at least 10% w/w fungal biomass and at least 20% w/w meat. In certain embodiments, the food products comprise at least 20% w/w fungal biomass and at least 20% w/w meat. In certain embodiments, the food products comprise at least 15% w/w fungal biomass and at least 20% w/w meat. In certain embodiments, the food products comprise at least 20% w/w fungal biomass and at least 20% w/w meat. In certain embodiments, the food products comprise at least 20% w/w fungal biomass and at least 20% w/w meat. In certain embodiments, the food products comprise at least 25% w/w fungal biomass and at least 20% w/w meat. In certain embodiments, the food products comprise at least 30% w/w fungal biomass and at least 20% w/w meat. In certain embodiments, the food products comprise at least 35% w/w fungal biomass and at least 20% w/w meat. In certain embodiments, the food products comprise at least 40% w/w fungal biomass and at least 20% w/w meat. In certain embodiments, the food products comprise at least 45% w/w fungal biomass and at least 20% w/w meat. In certain embodiments, the food products comprise at least 50% w/w fungal biomass and at least 20% w/w meat.

In certain embodiments, the food products comprise at least 5% w/w fungal biomass and at least 30% w/w meat. In certain embodiments, the food products comprise at least 10% w/w fungal biomass and at least 30% w/w meat. In certain embodiments, the food products comprise at least 20% w/w fungal biomass and at least 30% w/w meat. In certain embodiments, the food products comprise at least 15% w/w fungal biomass and at least 30% w/w meat. In certain embodiments, the food products comprise at least 20% w/w fungal biomass and at least 30% w/w meat. In certain embodiments, the food products comprise at least 20% w/w fungal biomass and at least 30% w/w meat. In certain embodiments, the food products comprise at least 25% w/w fungal biomass and at least 30% w/w meat. In certain embodiments, the food products comprise at least 30% w/w fungal biomass and at least 30% w/w meat. In certain embodiments, the food products comprise at least 35% w/w fungal biomass and at least 30% w/w meat. In certain embodiments, the food products comprise at least 40% w/w fungal biomass and at least 30% w/w meat. In certain embodiments, the food products comprise at least 45% w/w fungal biomass and at least 30% w/w meat. In certain embodiments, the food products comprise at least 50% w/w fungal biomass and at least 30% w/w meat.

In certain embodiments, the food products comprise at least 5% w/w fungal biomass and at least 40% w/w meat. In certain embodiments, the food products comprise at least 10% w/w fungal biomass and at least 40% w/w meat. In certain embodiments, the food products comprise at least 20% w/w fungal biomass and at least 40% w/w meat. In certain embodiments, the food products comprise at least 15% w/w fungal biomass and at least 40% w/w meat. In certain embodiments, the food products comprise at least 20% w/w fungal biomass and at least 40% w/w meat. In certain embodiments, the food products comprise at least 20% w/w fungal biomass and at least 40% w/w meat. In certain embodiments, the food products comprise at least 25% w/w fungal biomass and at least 40% w/w meat. In certain embodiments, the food products comprise at least 30% w/w fungal biomass and at least 40% w/w meat. In certain embodiments, the food products comprise at least 35% w/w fungal biomass and at least 40% w/w meat. In certain embodiments, the food products comprise at least 40% w/w fungal biomass and at least 40% w/w meat. In certain embodiments, the food products comprise at least 45% w/w fungal biomass and at least 40% w/w meat. In certain embodiments, the food products comprise at least 50% w/w fungal biomass and at least 40% w/w meat.

In certain embodiments, provided herein is a meat analogue from the biomass of *Tuber melanosporum* as a "truffle burger".

In some embodiments the ingredient described herein is combined with seaweed biomass. In certain embodiments the ingredient described herein is combined with algae.

FIG. 1 provides an overview of an embodiment of the fermentation process used to produce the biomass described herein Block 1 describes the substrate feedstock used for the fermentation and the injection of said substrate into the reactor post sterilization. The substrate can be a waste stream, plant hydrolysate, plant material, nutrient salts, sugars, starches, fatty acids, proteins, and other nutrients.

Block 2 describes the introduction of the filamentous fungi described herein into the substrate.

Block 3 describes the fermentation parameters described herein.

Blocks 4a. and 5a. describe an optional intermittent substrate introduction and harvesting fermentation operation strategy.

Blocks 4b. and 5b. describe an optional continuous substrate introduction and harvesting fermentation operation strategy.

Block 4c. describes an optional batch fermentation operation strategy.

Figure 2:
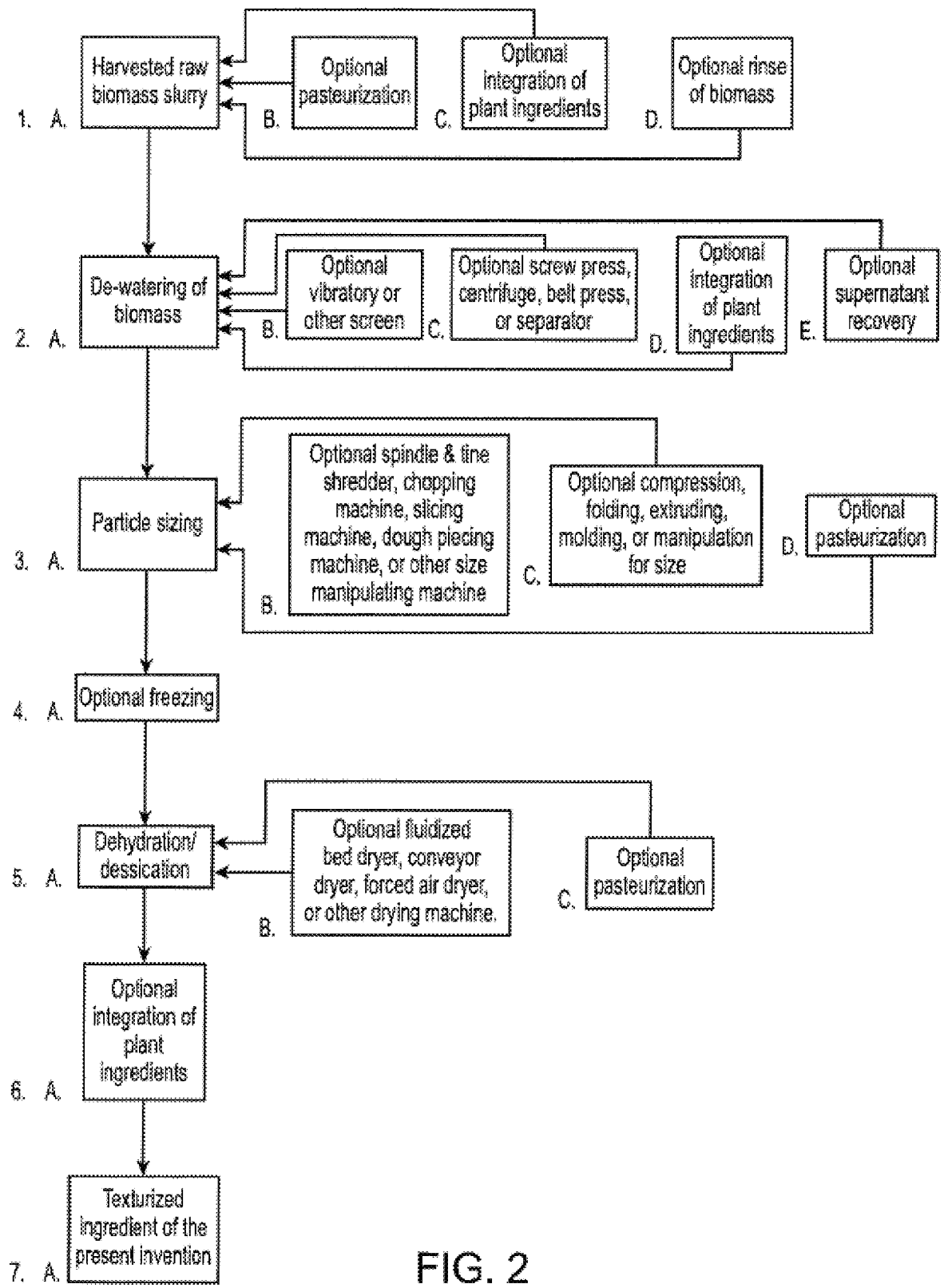
FIG. 2 provides an overview of some methods for processing of the fungal biomass slurry into the textured cultured protein (TCP) described herein.

FIG. 2 provides an overview of some methods for the processing of the fungal biomass slurry into the textured cultured protein (TCP) described herein Blocks 1a.-1d. disclose the raw biomass slurry of the fermentations described herein. The slurry includes but is not limited to biomass fermented with wastewater, co-products, and/or side streams from food and beverage processing, biomass fermented with conventional fermentation substrates, and biomass fermented with plant based ingredients. The biomass may be rinsed to remove residual substrate. The biomass may have the aforementioned plant ingredients integrated at this point. The material may be pasteurized post-harvest from the fermentation.

Blocks 2a.-2e. disclose the steps of processing the biomass to remove moisture via de-watering methods and the option to integrate the plant-based ingredients described herein. The supernatant may optionally be recovered for further purification.

Blocks 3a.-3d. disclose the steps of sizing the particles described herein. Different isolated particle sizes as well as combinations of particle sizes lend themselves to different applications in food products.

Blocks 4a.-5c. disclose optional pasteurization steps where particles and pieces are pasteurized prior to, during, or after dehydration.

Block 4a. describes the optional steps of freezing the pieces of TCP.

Blocks 5a.-5c. disclose the dehydration and desiccation steps for the removal of moisture from the biomass to make the dry and shelf stable ingredient described herein.

Block 6. Discloses the optional combination of other ingredients with the dried pieces to form a composition.

Block 7. discloses the dry ingredient described herein.

Figure 3:
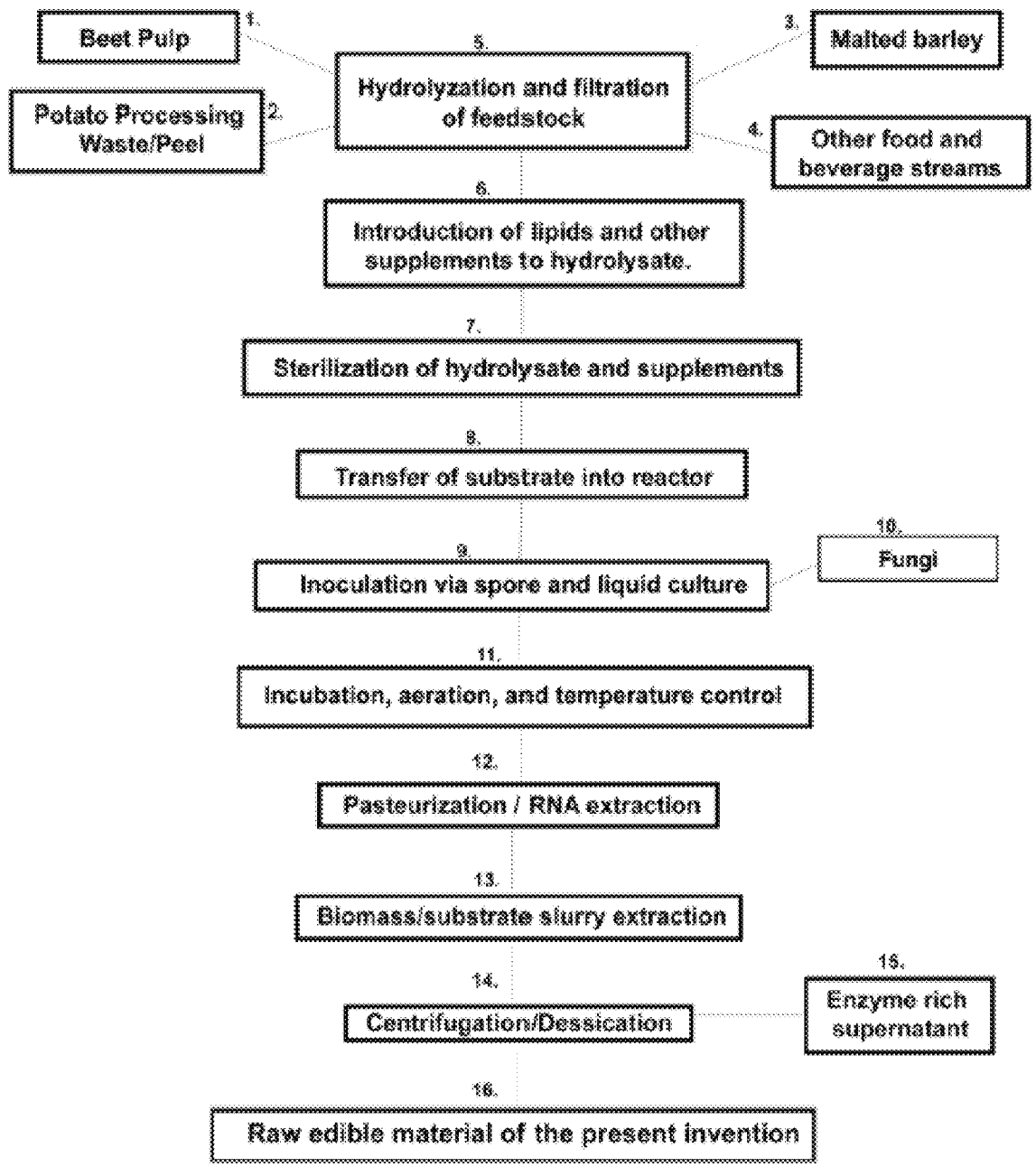
FIG. 3 provides an overview of one embodiment of the fungal biomass fermentation described herein.

FIG. 3 provides an overview of one embodiment of the fungal biomass fermentation described herein Block 1-4 discloses some possible plant materials to be processed into substrate. The plant material can be sourced as waste streams from the food and beverage industries.

Block 5 discloses the step of processing the plant materials into substrate of the fermentation. The plant material is soaked in 100 C water and agitated for 10-120 minutes. The hydrolyzed plant material is separated from the liquid hydrolysate via filtration.

Block 6 discloses the addition of supplements to balance the carbon/nitrogen rations and overall nutritional profile of the substrate. Supplements can be but are not limited to, ammonium phosphate, potassium nitrate, calcium sulfate, glucose, sucrose, or any combination thereof.

Block 7 discloses the requirement of the substrate sterility. The majority of the substrate is heat sterilized, however select ingredients such as the vitamins (for example, vitamin B12 and vitamin B7; (biotin)) are filtered and injected separately.

Block 8 discloses the transfer of the media into the reactor.

Block 9 discloses the methods for inoculation. Liquid seed cultures of mycelium may be transferred into the reactor, high loads of spores can be injected into the substrate, or a volume of biomass/substrate can be in the reactor already, propagated as an inoculum. It is a facet described herein to use fungi of the Phyla Ascomycota and Zygomycota including but not limited to; *Aspergillus oryzae, Rhizopus oryzae, Fusarium graminareum, Cordyceps militaris, Cordyceps sinensis, Tuber melanosporum, Tuber magnatum, Pennicillium camemberti, Neurospora crassa, Neurospora intermedia, Neurospora sitophila*, or *Xylaria hypoxion*.

Block 10 discloses the addition of a species of fungi as the organism of the fermentation.

Block 11 discloses the fermentation method. Temperature is maintained at 20-34° C., aeration is increased over time using both ambient gas concentrations as well as pure oxygen ranging from 0.03-2 vvm (volume of air per volume of medium per minute). PH is maintained in a state that is ideal for filamentous fungi. A pH of 3-8 is the range described herein.

Block 12 discloses the pasteurization of the mycelium. This destroys the viability of the fungus to continue growing and extracts much of the RNA that in undesirable in cellular protein products.

Block 13 discloses the extraction of the biomass and substrate mixture from the bioreactor.

Block 14 discloses the step of de-watering the fungal mycelium. The high moisture retention properties of the mycelium make it necessary to remove some liquid for ideal moisture contents that mimic meat.

Block 15 discloses the remainder of de-watering. This supernatant contains enzymes, acids, lipids, and other valuable extracellular components.

Block 16 discloses the end multi-use fungal biomass material described herein. This is the material that gets used in the blended meats, the blended plant, and the TCP food products.

Figure 4:
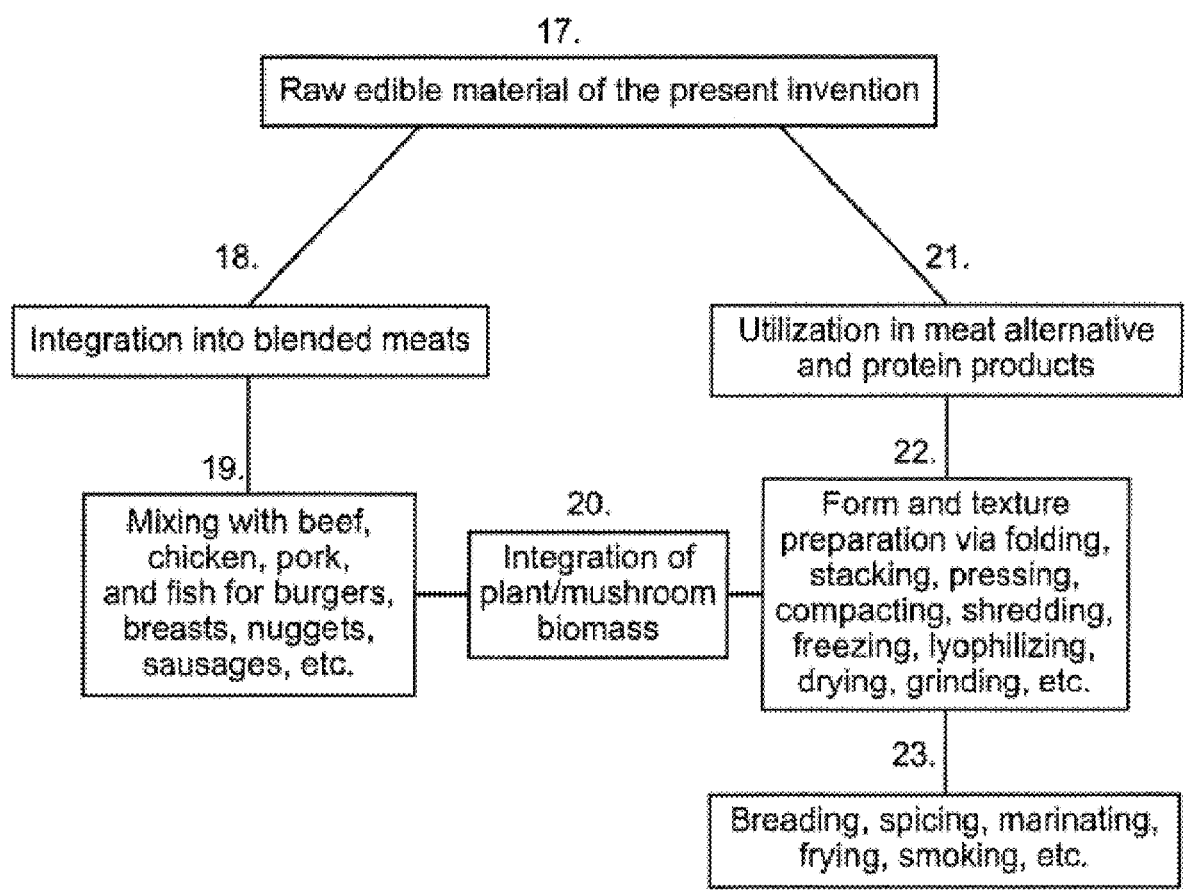
FIG. 4 provides an overview of optional applications of some of the ingredients described herein.

FIG. 4 provides an overview of optional applications of the ingredients described herein Block 17 Discloses the raw food material described herein.

Block 18 disclosed the blending of the fungal biomass into meats to produce hybrid meat/fungi food products.

Block 19 discloses some but not all of the meats and meat products the material is integrated into.

Block 20 discloses the addition of plant and mushroom biomass into the blended fungi/meat products as well as into the fungi based meat alternatives.

Block 21 discloses the use of the material described herein in meat alternative products.

Block 22 discloses some but not all methods for preparation and texturization of the material described herein.

Block 23 discloses some ways in which the meat analogue products are further prepared and cooked.

Figure 5A:
FIGS. 5A and 5B provide photographs of exemplary shelf-stable protein food ingredients provided herein.
Figure 5B:

FIG. 5A provides a close-up photograph on an exemplary TCP provided herein. FIG. 5B provides a photograph of an exemplary TCP provided herein on a serving plate.

EXAMPLES

Below the methods and compositions are further described in examples. These examples are in no way described to limit the present embodiments or their contents.

Example 1

Spores from *Rhizopus oryzae* were plated on agar containing vessels consisting of 15 g/l sucrose, 3 g/l Na3 citrate, 5 g/l KH2PO4, 2 g/l NH4NO3, 0.2 g/l MgSO4, 1 g/l CaSO4, 0.005 g/l Zn SO4, 0.001 g/l Fe(NH4)2(SO4)2, 0.00025 g/l CuSO4, 0.0001 g/l MnSO4, 0.0025 g/l biotin, and 15 g/l agar.

The cultures were incubated at 28° C. for 3 days to encourage maximum sporulation. The air/agar interface supplies aerial hyphae with nutrients embedded in the substrate while exposing hyphae to oxygen. Generous airflow was provided to the culture vessels. The spores were collected in a sterile polypropylene vessel.

The 17 L reactor was prepared by sterilization via 130° C. steam and introducing autoclaved substrate. The reactor substrate consisted of 17 liters DI water, 30 g/l light malt extract prepared from the hydrolyzation and filtration of malted barley, 10 g/l glucose, 5 g/l yeast extract, 0.5 g/l $NH_4H_2NO_3$, 0.2 g/l $MgSO_4$, 3 g/l safflower oil, and 0.0025 g/l biotin.

These spores were then introduced to the 17 l reactor at the concentration of 50,000/ml. The reactor was incubated at 29° C. with an increasing aeration starting at 0.1 vvm and reaching 0.8 vvm atmospheric air after 24 hours. The fermentation was complete after 48 hours.

The end substrate/biomass mixture was pressed in a porous cubic frame to de-water the biomass down to 68% for use in aforementioned food products. Samples were taken of the biomass and dried out at 101° C. It was determined via triplicate sampling that the reactor yielded 17 g/l of dry biomass.

Example 2

Aerobic fermentation was carried out in pulse feeding mode. 17l DI water, 30 g/l light malt extract prepared from the hydrolyzation of spent malted barley, 10 g/l glucose, 5 g/l yeast extract, 0.5 g/l $NH_4H_2NO_3$, 0.2 g/l $MgSO_4$, 3 g/l safflower oil, and 0.0025 g/l biotin was autoclaved and added to the sterile reactor. 150 ml of a 2 day old liquid culture of *Cordyceps militaris* mycelium grown on 25 g/l sucrose, 3 g/l $Na_3$ citrate, 5 g/l $KH_2PO_4$, 2 g/l $NH_4NO_3$, 0.2 g/l $MgSO_4$, 1 g/l $CaSO_4$, 0.005 g/l Zn $SO_4$, 0.001 g/l $Fe(NH_4)_2(SO_4)_2$, 0.00025 g/l $CuSO_4$, 0.0001 g/l $MnSO_4$, and 0.0025 g/l biotin. The reactor was maintained at a pH above 4.5 by dripping NaOH and held at 25 C with an increasing ambient air aeration starting at 0.1 vvm and reaching 0.8 vvm after 24 hours. 20 g/l light malt, 10 g/l glucose, and 20 g/l yeast extract was autoclaved and injected into the reactor on hour 48 of the incubation. This substrate supplementation was repeated on hour 96. The growth phase ended on hour 143. The substrate/biomass mixture was pressed in a porous cubic frame and de-watered down to 65% water content. The supernatant was disposed. The pulse feeding strategy yielded 41 g/l of dry biomass.

Example 3

Aerobic fermentation was carried out in pulse feeding/pulse harvest mode. 17 l DI water, 30 g/l potato extract prepared from the hydrolyzation of potato skin, 10 g/l glucose, 2 g/l yeast extract, 0.5 g/l $NH_4H_2NO_3$, 0.2 g/l $MgSO_4$, 3 g/l safflower oil, and 0.0025 g/l biotin was autoclaved and added to the sterile reactor. 50,000 *Aspergillus oryzae* spores/l were added to the substrate. The reactor was maintained at a pH of 4.5 by dripping NaOH into the substrate as needed. The reactor was maintained at 29 C with an increasing ambient air aeration starting at 0.1 vvm and reaching 0.8 vvm after 24 hours. After 48 hours 85% of the substrate biomass mixture was removed. A sterile solution of 14l DI water, 30 g/l potato extract, 10 g/l glucose, 2 g/l yeast extract, 0.5 g/l $NH_4H_2NO_3$, 0.2 g/l $MgSO_4$, 3 g/l safflower oil, and 0.0025 g/l biotin was added filling the reactor back up to almost 17l. The fermentation continued for another 24 hours before the extraction and re-supplementation process was repeated at hour 72. This was then repeated a third time at hour 96. The final harvest of the entire volume of the reactor occurred at hour 120. Biomass was removed and de-watered down to 65% using pressure in a cubic porous frame for further processing into product samples. Biomass yield samplings were carried out in triplicates at each biomass extraction point (hr 48, hr 72, hr 96, and hr 120). Hour 48 had an average of 16.3 g/l dry biomass, hour 72 had an average of 15.7 g/l, hour 96 had an average of 16.1 g/l, and hour 120 had an average of 14.2 g/l.

Example 4

Biomass of *Neurospora intermedia* (500 g) at 80% water content cultured for 72 hours at 29 C with 0.5 v/v/m of aeration in a 300 l internal loop bioreactor at a pH>4.5 on 30 g/l light malt extract, 10 g/l glucose, 20 g/l yeast extract, 0.5 g/l $NH_4H_2NO_3$, 0.2 g/l $MgSO_4$, 3 g/l safflower oil, and 0.0025 g/l biotin added to a KitchenAid mixer with 50% (w/w) grass fed ground chuck beef (500 g) for a total of 1000 g of meat/mycelium mixture. The mixture was blended on low for 8 minutes until homogenous in texture and color. The mixture was removed and hand pressed into 5 circular patties 1.5" in height×6" in diameter. Two patties were grilled over a propane burner on a "medium" propane flow rate until considered cooked to a point of classification as "medium". Two patties were pan seared on medium heat until slightly blackened and long enough to be considered "medium". Two patties were baked at 425 F for 15 minutes. Two patties were flame cooked over charcoal until they could be considered "medium". Two patties were pan seared until they could be considered "medium rare". One control patty for each cooking method of pure chuck ground beef was cooked in the same fashion as the blended patties as a control.

Example 5

Biomass of *Aspergillus oryzae* (300 g) cultured in supplemented potato hydrolysate was dried in a dehydrator and pulverized into a powder using a mortar and pestle. The powder was mixed with mixed with whole wheat flower (50 g). The mixture was hydrated with 2 cups of whole milk and combined with 3 eggs. The mixture was blended together with ½ stick of butter until malleable dough was created. The dough was rolled into 2" balls and fried. Powdered sugar was added on top of the balls.

Example 6

Asexually sporulating cultures of *Neurospora intermedia* were used to inoculate 8 baffled shaker flasks with a working volume of 200 ml and a 0.2 μm filter patch embedded in the cap. The media contained in the flasks contained 30 g/l sucrose, 3 g/l Na3 citrate, 2 g/l KH2PO4, 2 g/l NH4NO3, 0.2 g/l MgSO4, 1 g/l CaSO4, 0.005 g/l Zn SO4, 0.001 g/l Fe(NH4)2(SO4)2, 0.00025 g/l CuSO4, 0.0001 g/l MnSO4, 0.0025 g/l biotin, and 15 g/l agar. These flasks were incubated and agitated for 24 hours at 100 rpm and 29° C. on a incubated shaker table.

A 100 liter internal loop airlift bioreactor (ILAB) was filled to an 80 L working volume with DI water. Using a magnetically coupled agitator for agitation, 45 g/l potato flour, 2 g/l yeast extract, 0.5 g/l $NH_4H_2NO_3$, 0.0025 g/l biotin was successively added to the vessel until homogenous. The media was sterilized with steam in place methods (125° C. for 20 minutes). The eight 24-hour old baffled flask starter cultures were aseptically injected into the 100 l reactor. The reactor was maintained at 31° C. The reactor was maintained at a pH of 4.5 by dripping NaOH into the substrate as needed. Compressed filter sterilized air was injected through a sintered steel sparger with a porosity of 2.2 microns in the riser section of the ILAB at a flow rate of 0.1 vvm. The flow rate was increased to 1.0 vvm over the first 48 hours.

These conditions were maintained for 72 hours.

The biomass slurry was filtered using nylon mesh filter sacks to remove the supernatant leaving a high moisture biomass. The high moisture biomass was centrifuged to further reduce the moisture content down to 75%. The reduced moisture biomass was shredded into particles less than 0.25" by using a shaft mounted 5 blade shredder at 500 rpm. Particles were sieved to separate the particle sizes. Particles were dehydrated at 60° C. for 120 minutes until bone dry with a moisture content of 4%. The material was packaged and stored.

Example 7

A 48 hour old fermentation operating in a 100 l internal loop airlift bioreactor with *Neurospora crassa* biomass and 30 g/l sucrose, 3 g/l Na3 citrate, 2 g/l KH2PO4, 2 g/l NH4NO3, 0.2 g/l MgSO4, 1 g/l CaSO4, 0.005 g/l Zn SO4, 0.001 g/l Fe(NH4)2(SO4)2, 0.00025 g/l CuSO4, 0.0001 g/l MnSO4, 0.0025 g/l biotin was injected, via peristaltic pumping, with 10 g/l of powdered dried oats that had been steam sterilized in four, 1 liter glass bottles with DI water adjusted to the one liter mark on each bottle. The fermentation was continued with the previous conditions for a remaining 8 hours. The material was harvested and processed with typical methods.

Example 8

The dry TCP described herein was fully characterized in its nutritional profile and texture. The TCP was cultivated in a 100 liter internal loop airlift bioreactor for 3 days at 31° C. with 0.7 VVM of compressed air and 40 g/l sucrose, 3 g/l sodium citrate, 3.5 g/l ammonium phosphate, 1.3 g/l potassium nitrate, 0.1 g/l magnesium sulfate, 0.05 g/l calcium chloride and minor amounts of copper, iron, manganese, and zinc. The material was harvested in slurry form, de-watered down to 75% water using a vibratory screen and screw press, compacted into a dense block, shredded with a spindle and tine shredding device, sized with a 5 mm mesh, and dehydrated with a forced air conveyor dryer. The material was baked at 83° C. in a convection oven for 15 minutes for a final pasteurization. The material with an ambient hydration of 4.3% water content (WC) was analyzed for a full nutritional profile via triplicate sampling. The following are averages. Using AOAC method 991.43, fiber content was determined to be 18.14%. Using AOAC method 990.03 total protein was determined to be 53%. Using AOAC method 945.44 total fat was determined to be 9.02%. Using AOAC methods for individual amino acids the following concentrations were determined: Methionine 0.53%, Cystine 0.47%, Lysine 2.49, Phenylalanine 1.35%, Leucine 3.02%, Isoleucine 1.53%, Threonine 1.79%, Valine, 2.84%, Histidine 1.61%, Arginine 3.07%, Glycine 1.52%, Aspartic acid 3.91%, Serine 1.74%, Glutamic acid 5.78%, Proline 1.44%, Hydroxyproline 0.04%, Alanine 2.51%, Tyrosine 2.17%, and Tryptophan 0.42%, Taurine 0.01%. AOAC method 2012.13 was used to determine the fatty acid profile which was determined to be (relative %): Total omega 3 content 3.3%, total omega 6 content 35.9%, total omega 9 content 38.3%, total saturated 17.8%, total monounsaturated 42.7%, and total polyunsaturated 39.3%. Using AOAC method 990.12 the aerobic plate count was determined to be <10,000 cfu/g. Using AOAC method 997.02 the mold and yeast count was determined to be <200 CFU/g. Using AOAC method 991.14 the *E. coli* levels were determined to be <10/g. Using AOAC method 2003.09 the *Salmonella* spp. Was determined to be negative in 375 grams of TCP.

The aforementioned TCP was then characterized in its texture and macro-scale characteristics after hydration. Color was visually determined to be an off white/tan. Particle size was determined to be an average of 5 mm on the x, y, and z planes. Water absorption capacity (WAC) was determined to be 4624.77 g/kg. The chewiness, cohesiveness, springiness, as well as transversal and longitudinal cutting strength were analyzed to determine "texture". The chewiness was determined to be 3.43 kg. The cohesiveness was determined to be 45%. The springiness was determined to be 62%. Transversal cutting strength was determined to be 12,408 kg/m$^{-2}$. Longitudinal cutting strength was determined to be 11,316 kg/m$^{-2}$. These numbers were compared to results from beef, chicken, and pork.

Example 9: Blended Beef/TCP Patties 60 g immobilized TCP of *Rhizopus oryzae* hydrated at 72% water content/60 g ground chuck beef.

Fungal biomass was hydrated and added to the ground beef after the initial course grind. The components were then mixed/blended into the desired consistency for burger patties.

The ground beef/fungi blend was packed into a circular mold with a diameter of 120 mm.

The patty was cooked in an oiled pan on medium heat until internal temperature reached 73 C.

Example 10: Blended Chicken/TCP Breaded Nuggets 70 g immobilized TCP of *Aspergillus oryzae* hydrated at 65% water content/30 g ground white meat chicken.

Fungal TCP was hydrated and added to shredded chicken breast meat. The mixture was tossed and ground through plates with ⅛" holes.

Meat blend was scooped into 10 gram nuggets. The nuggets were compressed into a breading consisting of 80% whole wheat flower, 18.3% bread crumbs, 0.6% salt, 0.2% paprika, 0.2% basil, 0.2% cayenne pepper, 0.2% garlic powder, 0.3% ground black pepper by dry weight. Compression was applied to both sides of the nugget, simultaneously covering the entire meat blend and flattening the nugget on two sides.

Nuggets were fried in ¼" depth peanut oil until breading was crispy.

Example 11: Blended Pork/TCP Sausages 130 g immobilized TCP of *Neurospora intermedia* hydrated at 68% water content/80 g ground pork/30 g pork fat.

TCP was hydrated and added to ground pork and fat mixture. Contents were mixed with 0.2 g salt, 0.05 g powdered sage, 0.1 g ground black pepper, 0.2 g Italian herbs, 0.1 g paprika. Mixture was mixed together using a mechanical mixer for 4 minutes. Mixture was put through a grinder with ⅛" holes.

Ground and blended material was injected into a cleaned and prepared natural hog sausage casing and tied off to close. The sausage was twisted and cut to produce two sausage links.

Links were pan seared in a pan on medium heat until center temperature reached 71° C.

Example 12: Thy Chicken Extender 80 g of immobilized *Neurospora sitophila* TCP at 6% water content.

Raw mycelium was harvested and de-watered down to 70% water content using a screen and screw press. This material was shredded, sized into 5 mm particles, and consecutively dried down to 6% water content. This TCP was then baked in an oven at 85° C. for 15 minutes for a final pasteurization. 80 g of the TCP was mixed and coated with 10 g safflower oil, 5 g algae, 5 g natural chicken flavoring.

The composition had particle sizes of 3-10 mm. The plant-based ingredients adhered evenly to the surfaces of the dehydrated mycelium particles. The mixture had a tan color and tasted like dry chicken.

The composition was hydrated at a 1/1.5 ratio of dry material to water by weight. This hydrated material was mixed at a 30/70% ratio of composition to ground chicken in a mixer until texturally homogenous (roughly 30 seconds). The blended chicken was formed into patties and cooked in the same way as chicken patties.

Example 13: Dry Pork Extender 72 g of immobilized *Neurospora intermedia* TCP at 5.5% water content.

Raw mycelium was harvested and de-watered down to 70% water content using a screen and screw press. This material was shredded, sized into 5 mm particles, and consecutively dried down to 6% water content. This TCP was then baked in an oven at 85° C. for 15 minutes for a final pasteurization. 72 g of the TCP was mixed and coated with 10 g safflower oil, 2 g yeast extract, 6 g bamboo fiber, 10 g natural pork flavoring.

The composition had particle sizes of 3-10 mm. The plant-based ingredients adhered evenly to the surfaces of the dehydrated mycelium particles. The mixture had a tan color and tasted like dry pork.

The composition was hydrated at a 1/1.5 ratio of dry material to water by weight. This hydrated material was mixed at a 30/70% ratio of composition to ground pork in a mixer until texturally homogenous (roughly 30 seconds). The blended pork was formed into sausage links and cooked in the same way as pure pork sausages.

Example 14: Dry Beef Extender 64 g of immobilized *Neurospora crassa* TCP at 6% water content.

Raw mycelium was harvested and de-watered down to 70% water content using a screen and screw press. This material was shredded, sized into 5 mm particles, and consecutively dried down to 6% water content. This material was then baked in an oven at 85° C. for 15 minutes for a final pasteurization. 64 g of the material was mixed and coated with 10 g safflower oil, 2 g yeast extract, 5 g psyllium husk, 10 g beet pulp powder, 10 g natural beef flavoring.

The composition had particle sizes of 3-10 mm. The plant-based ingredients adhered evenly to the surfaces of the TCP particles. The mixture had a tan color and tasted like dry beef.

The composition was hydrated at a 1/1.5 ratio of dry material to water by weight. This hydrated material was mixed at a 30/70% ratio of composition to ground beef in a mixer until texturally homogenous (roughly 30 seconds).

The blended beef was formed into burger patties and cooked in the same way as pure beef burgers.

Example 15: Dry Chicken Extender 80 g of immobilized *Neurospora sitophila* TCP at 6% water content.

Raw mycelium was harvested and de-watered down to 70% water content using a screen and screw press. This material was shredded and consecutively dried down to 6% water content. This material was then baked in an oven at 85° C. for 15 minutes for a final pasteurization. 80 g of the TCP was mixed and coated with 10 g safflower oil, 5 g algae, 5 g natural chicken flavoring.

The composition had particle sizes of 3-10 mm. The plant based ingredients adhered evenly to the surfaces of the TCP particles. The mixture had a tan color and tasted like dry chicken.

The composition was hydrated at a 1/1.5 ratio of dry material to water by weight. This hydrated material was mixed at a 30/70% ratio of composition to ground chicken in a mixer until texturally homogenous (roughly 30 seconds). The blended chicken was formed into patties and cooked in the same way as chicken patties.

Example 16: Dry Pork Extender 72 g of immobilized *Neurospora intermedia* at 5.5% water content.

Raw mycelium was harvested and de-watered down to 70% water content using a screen and screw press. This material was shredded and consecutively dried down to 6% water content. This material was then baked in an oven at 85° C. for 15 minutes for a final pasteurization. 72 g of the TCP was mixed and coated with 10 g safflower oil, 2 g yeast extract, 6 g bamboo fiber, 10 g natural pork flavoring.

The composition had particle sizes of about 3-10 mm. The plant-based ingredients adhered evenly to the surfaces of the TCP particles. The mixture had a tan color and tasted like dry pork.

The composition was hydrated at a 1/1.5 ratio of dry material to water by weight. This hydrated material was mixed at a 30/70% ratio of composition to ground pork in a mixer until texturally homogenous (roughly 30 seconds). The blended pork was formed into sausage links and cooked in the same way as pure pork sausages.

Example 17: Dry Beef Extender 64 g of immobilized *Neurospora crassa* at 6% water content.

Raw mycelium was harvested and de-watered down to 70% water content using a screen and screw press. This material was shredded and consecutively dried down to 6% water content. This material was then baked in an oven at 85° C. for 15 minutes for a final pasteurization. 64 g of the material was mixed and coated with 10 g safflower oil, 2 g yeast extract, 5 g psyllium husk, 10 g beet pulp powder, and 10 g natural beef flavoring.

The composition had particle sizes of about 3-10 mm. The plant-based ingredients adhered evenly to the surfaces of the TCP particles. The mixture had a tan color and tasted like dry beef.

The composition was hydrated at a 1/1.5 ratio of dry material to water by weight. This hydrated material was mixed at a 30/70% ratio of composition to ground beef in a mixer until texturally homogenous (roughly 30 seconds). The blended beef was formed into burger patties and cooked in the same way as pure beef burgers.

Example 18: Focus Group on TCP in Blended Meat Application

The dry shelf-stable ingredient of the present disclosure with a D-50 of 4 mm at 75% w/w was coated in safflower oil at 10% w/w and blended with "brown chicken" natural flavor (Fontana Flavors) at 10% w/w as well as pea fiber at 5% w/w. The coated particles were hydrated at a 1/2 ratio of particles/water w/w (200% hydration) and left to soak for 25 minutes. The hydrated TCP was mixed with ground chicken meat at a 50/50 ratio w/w. The blend was formed into 16 g nuggets, then breaded in a standard nugget breading consisting of rice flour, wheat flour, cornmeal, and spices.

Pure ground chicken was formed into 16 g nuggets and breaded with the exact same breading formula. Both the pure chicken and the blended nuggets were fried until they floated in the oil and had a golden crispy breading. The products were kept separate, given the respective ID's of 1776 for fully chicken and 1865 for the blended nugget.

20 random testers were selected from a bank of participants unfamiliar to the project. They were requested to taste the two samples and to record their preference using three options; "X preferred" or "cannot tell the difference". The testers were served each sample with a short break in between. Their results were recorded.

12 said they could tell no difference. 6 preferred the blended nugget, and 2 preferred the fully meat nugget. (60% said no difference, 30% preferred the blended nugget, 10% preferred the full chicken nugget).

Example 19: Treatment Efficiency with Potato Processing Wastewater

Cultures of *Neurospora sitophila* were cultured in two 200 ml baffled shaker flasks with house media for 30 hours at 100 RPM and 31° C. Media was prepared in agitated 100l pressure vessels and steam sterilized to prepare 16l of media. The media consisted of potato processing wastewater generated from the blanching of potatoes from French fry production. The water contained a high COD of 37,304 mg/l COD, 2.34% TSS, 1397 mg/l TN, 3.5% sugars, as well as phosphate and sulphate. The media was supplemented with 1 g/l yeast extract, 0.5 g/l ammonium nitrate, and 10 ml of vegetable oil based antifoam. The media was steam sterilized and injected into the steam sterilized 17l reactor. The seed cultures (400 ml total) were added to the reactor. The fermentation was maintained at 31° C., a pH of 4.5 and 0.8 vvm of compressed air for three days (72 hours). The material was harvested and processed as typical with the methods of the present disclosure.

The supernatant was analyzed. Remaining COD was 1283 mg/l, TSS was 0.01%, TN was 188 mg/l and sugars was 0%. The treatment was highly effective in reducing COD as well as TSS and TN. In addition to creating a quality TCP from the process, the treatment capacity of the platform proves viable as a treatment to the potato processing waste.

Example 20. Optimizing Fungal Fermentation Using Potato Solids as Substrate

A. Characterization of Solid Potato Waste Material.

Potatoes (russet type) were peeled to retain about 50% of the peel and then cut into shoestrings and slivers. The material was mashed and comminuted using a blade food processor before further characterization.

TABLE 1

Solid potato waste substrates used during the research

| | |
|---|---|
| Peel (% of original tubes) | 35-55 |
| Dry weight (%) | 18.23-18.15 |
| Starch (%) | 10.68-14.18 |
| Protein (%) | 2.03-2.37 |
| pH | 5.47-5.96 |

B. Increasing Production of Fungal Biomass from Solid Potatoes.

Figure 6:
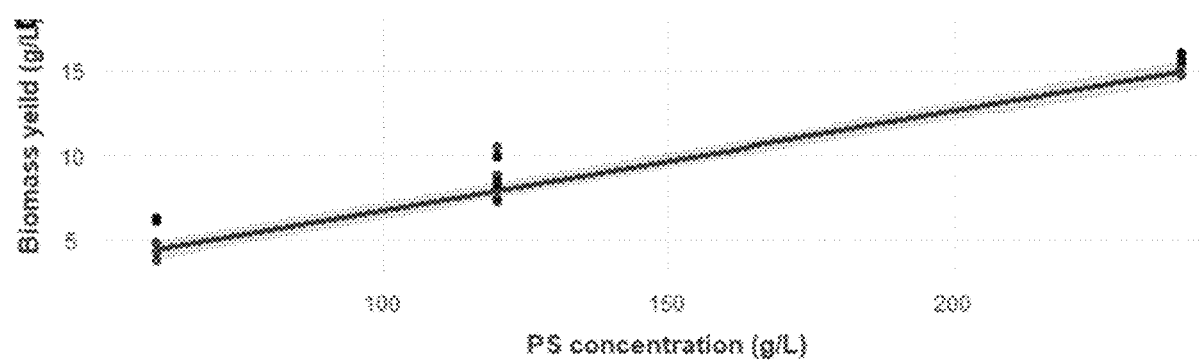
FIG. 6 shows that more *N. intermedia* mycelial biomass is produced by increasing the amount of potato solids in the liquid culture medium. Dry biomass yield production increased with increasing potato solids concentration. The gray area around the correlation line represents 95% confidence.
Figure 7:
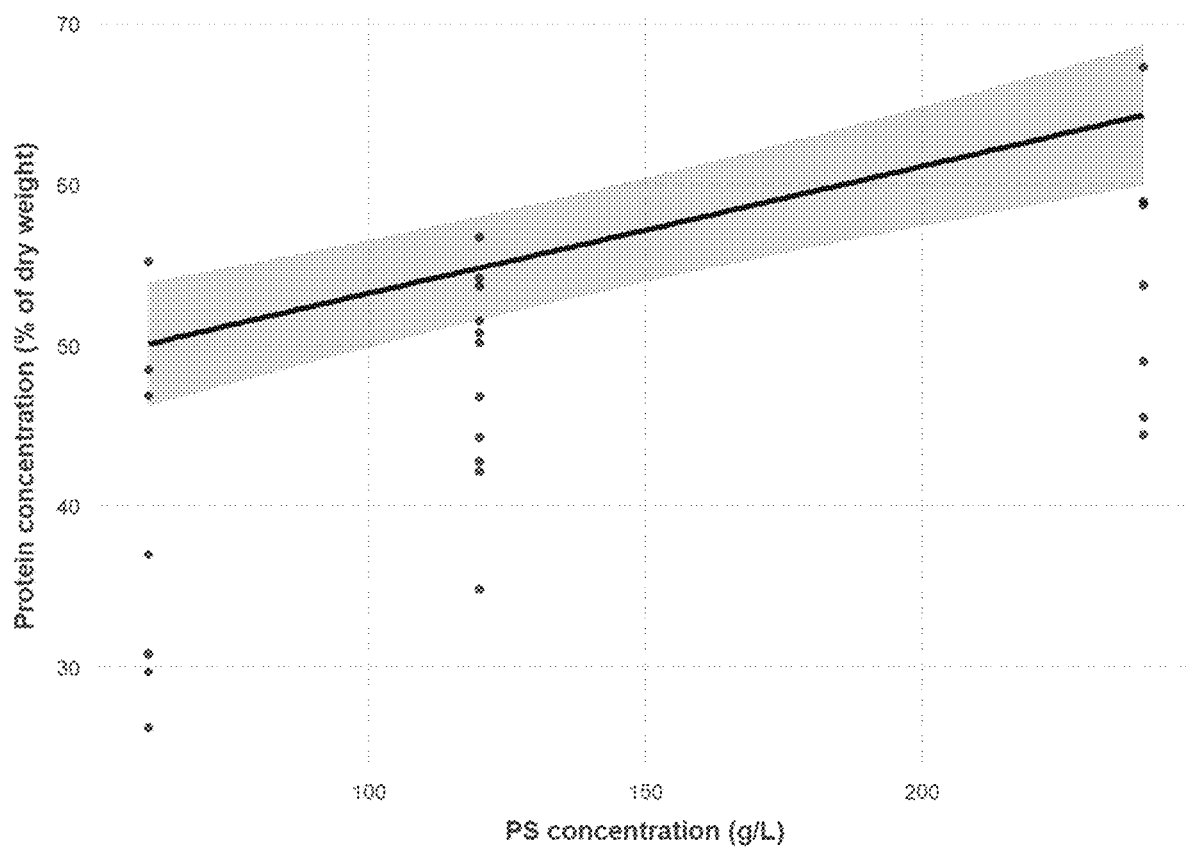
FIG. 7 shows that increasing potato solids concentration in the fermentation enhances protein accumulation in fungal mycelia. The percent of protein in dry mycelia fermented on various concentrations of potato solids was measured using a dye-binding method. The gray area around the regression line represents 95% confidence.

To determine the optimal amount of potato solids that can be used in the submerged cultivation of fungi, a potato substrate (PS) media was prepared. Solid potatoes with about 50% of the peel retained were comminuted in a blender (or a high-shear pump) to reduce particle size, improve starch gelatinization and minimize the peel size. In the case of a blade blender, it was operated until no additional reduction in particle size was observed. The parts of potato peel particle size were about 100-500 µm, and peel specs were still observable, about 500-1000 µm size. The comminuted potato homogenate was diluted to obtain various concentrations of solids before sterilization by autoclaving. 100 ml aliquots of the PS media were transferred in 500 ml Erlenmeyer flasks with 3-4 replicates for each concentration. Edible ascomycete Neurospora intermedia fungus was grown from stock on potato dextrose agar (PDA) plates. Conidia were harvested and counted using a hemocytometer to determine the concentration. Flasks with PS media were inoculated with the freshly harvested conidia to $10^5$ conidia/ml and cultivated at 30° C. with shaking at 200 RPM for 48 hours. The biomass was collected using vacuum filtration with a 1.2 µm pore filter disks and the dry weight yield was determined after the mycelia was dried overnight at 60° C. (FIG. 6). Increasing the concentration of homogenized potato solids in the PS media up to the practical solubility level of 250 g/l (equivalent to 45 g/l dry matter) leads to increased mycelial biomass yield. Protein concentration in the dry mycelia was also measured (FIG. 7). The resulting fungal biomass was ground to a fine powder and protein concentration was determined using a CEM Sprint Protein Analyzer based on the automated dye-binding method (AOAC 2011.04). Increasing the amount of comminuted potato solids in the PS media (i.e., PS concentration) for fungal fermentation correlated positively with higher protein accumulation (%) in the fungal mycelia. Increasing potato solids to 250 g/l of wet material (45 g/l dry matter) in the PS media substrate resulted in increased biomass in the product. An amount of about 250 g/l of potato solids in water is close to the maximal concentration limit of comminuted potato solids in water since at higher concentration the material did not homogenize and liquefy well and could not be pumped.

C. Efficient Fermentation Using Potato Solids as Substrate Negates the Need to Supplement the Media with Vitamins and Trace Elements.

Figure 8A:
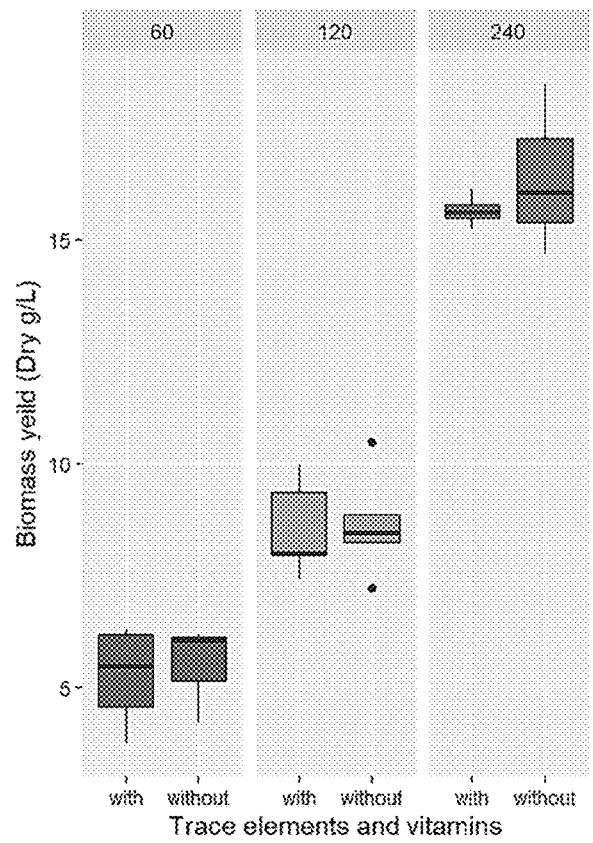
FIGS. 8A-8B show that the addition of vitamins and microelements to potato solids does not improve fungal yield. Fungal mycelium was produced using comminuted and diluted solid potatoes at different concentrations with or without the addition of vitamins and micronutrients. At the end of the fermentation, dry biomass yield was measured (FIG. 8A) and protein concentration (FIG. 8B) was determined using the dye-binding method. Data were analyzed using ANCOVA and Tukey-HSD test. Panels are of different potato substrate (PS) concentrations (g/l), the median and lower (Q1) and upper (Q3) quartile of each treatment are shown in the boxplot.
Figure 8B:
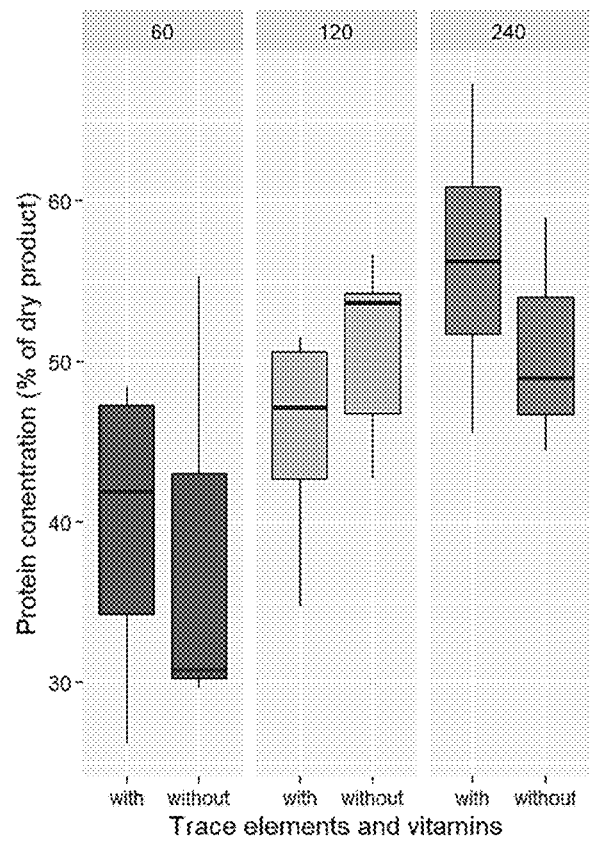

Synthetic or semi-synthetic, fermentation media is normally supplemented with vitamins and trace elements. Commonly, these include magnesium, citrate, phosphate, potassium, calcium, zinc, iron, copper, manganese, molybdate, nickel, borate, cobaltous, biotin, thiamine, inositol, and pyridoxine. Whole organic plant raw material not only can be a rich source of carbohydrates and protein, but also contains micronutrients to enable fungal cultivation. It was determined if media from potato solids requires additives in order to produce high amounts of mycelial biomass for food consumption with N. intermedia. PS media was prepared by comminuted potatoes in a blade blender as described in Example 20B, with 50% of the peel retained, as before diluted with water to different concentrations of 60, 120 or 240 g/l (potato solids/water) and either sterilized "as is", or supplemented with 5 ml of trace-elements solution per 1 L PS media (trace-element solution was composed of 5 g/l citric acid*$H_2O$, 50 g/l $ZnSO_4$*7 $H_2O$, 10 g/l $Fe(NH_4)2(SO_4)2$*$6H_2O$, 2.5 g/l $CuSO_4$*$5H_2O$, 0.5 g/l $MnSO_4$*$H_2O$, 0.5 g/l $H_3BO_3$, 0.5 g/l $Na_2MoO_4$*$2H_2O$, and 1 mg/l biotin). 100 ml aliquots of the PS media were transferred in 500 ml Erlenmeyer flasks with 4 replicates for each condition. N. intermedia was grown from stock on potato dextrose agar (PDA) plates. Conidia were harvested and counted using a hemocytometer to determine the concentration. Flasks with PS media were inoculated with the freshly harvested conidia to $10^5$ conidia/ml and cultivated at 30° C. with shaking at 200 RPM for 48 hours. The biomass was collected using vacuum filtration with 1.2 µm pore filter disks. The dry weight yield was determined after the mycelia were dried overnight at 60° C. Protein concentration was determined by grinding samples to a fine powder and using a Bradford protein assay. The data was analyzed using one-way ANCOVA, controlling for comminuted, homogenized potato solids concentration, and was followed by Tukey-HSD post-hoc test. Additions of vitamins and micronutrients (i.e., PS media+trace-elements) had no significant effect on the accumulation of fungal biomass (FIG. 8A) or protein yield (FIG. 8B) when compared to PS media alone, after controlling for the effect of the PS concentration. It was concluded that PS media derived from comminuted solid potato rejects is a rich source of nutrients for fungal fermentation and does not need any additional nutrient or trace-elements in order to produce ample biomass for food production. This simplifies and reduces the cost of producing edible mycelium from potato solids material.

D. The Addition of Simple Carbon to Potato Solid Media is not Needed for N. intermedia Fermentation.

Figure 9:
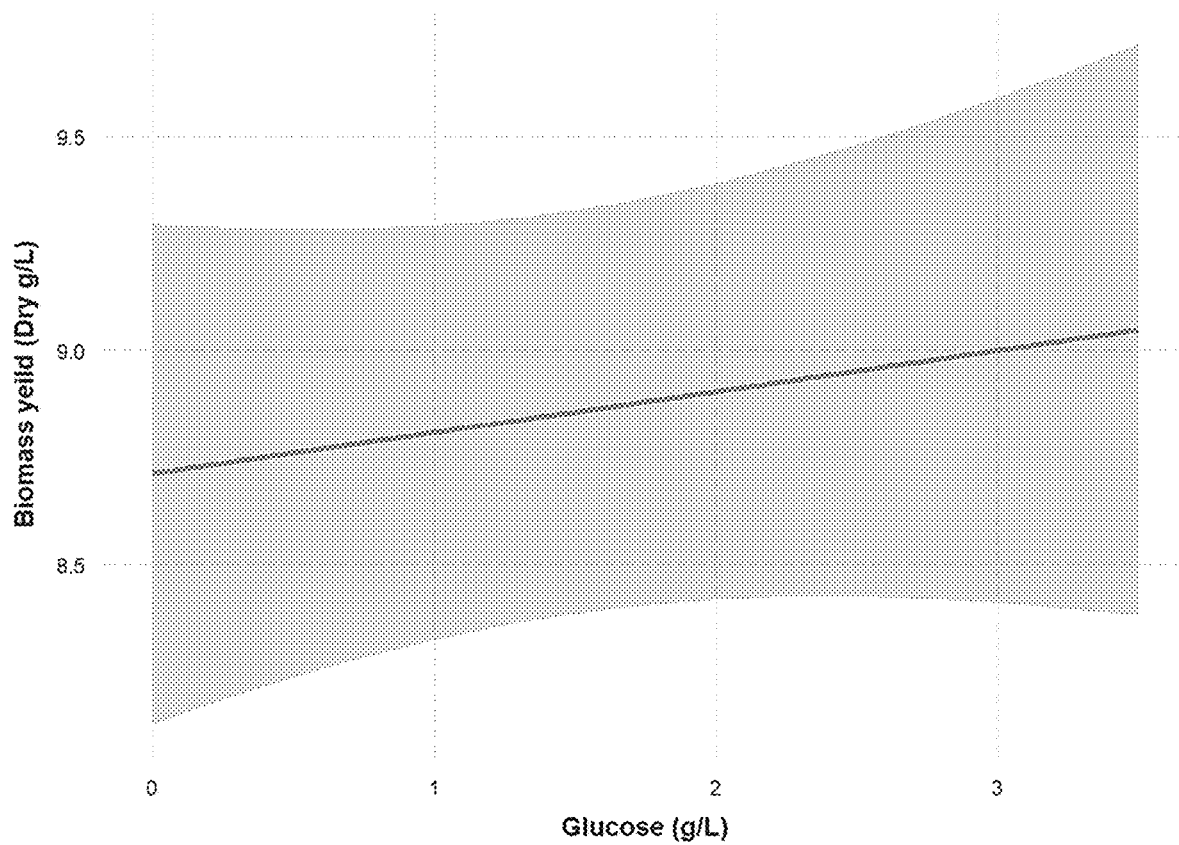
FIG. 9 shows that producing a high amount of food mycelium from solid potato substrate can be done without any additional carbon input. Fungi were grown on comminuted and diluted solid potatoes with varying amounts of added glucose. The dry biomass mycelium yield was weighed at the end of the fermentation. The gray area around the regression line represents 95% confidence.

The most common substrates currently in use for producing mycelium for food consumption in controlled liquid fermentation processes rely on simple carbon sources such as glucose or sucrose. On the other hand, solid potato waste contains about 60-80% starch of the total solid matter. Prior to cellular internalization and assimilation of starch by fungi, it must be broken into shorter carbon units. This process depends on the secretion and activity of amylase enzymes. This process can be less or more efficient in different species, extends growth time, and consumes energy from the cells, at the expense of biomass and protein accumulation. It was tested if an addition of a simple carbon alters mycelia production from solid potato substrate. PS media was prepared by comminuting fresh potatoes, with 50% of the peel retained (as in Example 20B), diluted with water to 45 g/l solids, and supplemented with glucose to various concentrations and autoclaved. 100 ml aliquots of the PS media were transferred in 500 ml Erlenmeyer flasks with 4 replicates for each treatment. N. intermedia was grown from stock on potato dextrose agar (PDA) plates. Conidia were harvested and counted using a hemocytometer to determine the concentration. Flasks with PS media were inoculated with the freshly harvested conidia to $10^5$ conidia/ml and cultivated at 30° C. with shaking at 200 RPM for 48 hours. The biomass was collected using vacuum filtration with 1.2 µm pore filter disks. The dry weight yield was determined after the mycelia were dried overnight at 60° C. Protein concentration was determined by grinding samples to a fine powder and on analysis using a CEM Sprint Protein Analyzer (AOAC 2011.04). Analysis of the resulting fungal biomass yield using linear modeling demonstrated that glucose addition is not needed to produce a high amount of mycelium when using solid potato substrate (FIG. 9). Additionally, the protein levels in the dry mycelia product were also not affected by supplementing the PS media with glucose. This shows that solid potato substrate can be used directly as the carbon source for producing mycelia for food production and no additional investment in carbon supplementation is required.

E. Fungal Protein Yield is Improved by the Addition of Inorganic Nitrogen to Potato Solids Media.

Figure 10A:
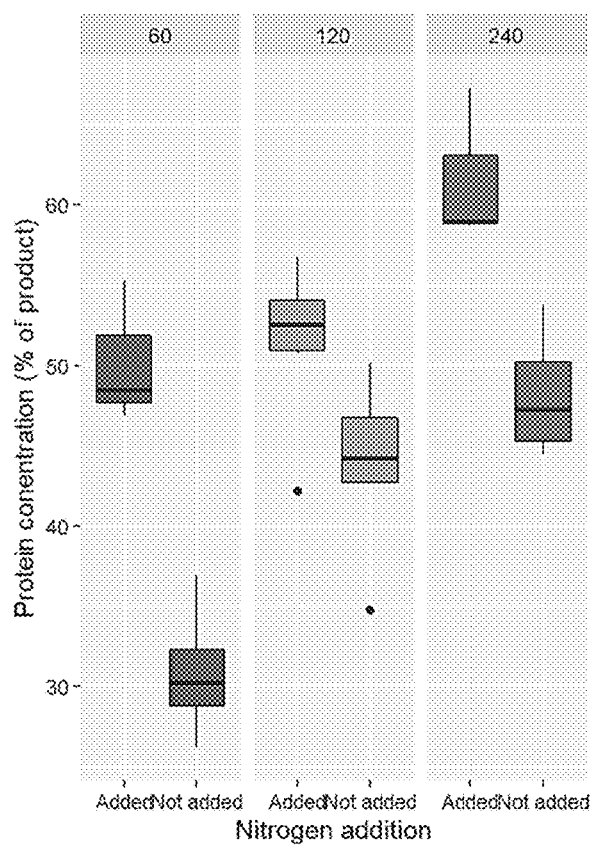
Figure 10B:
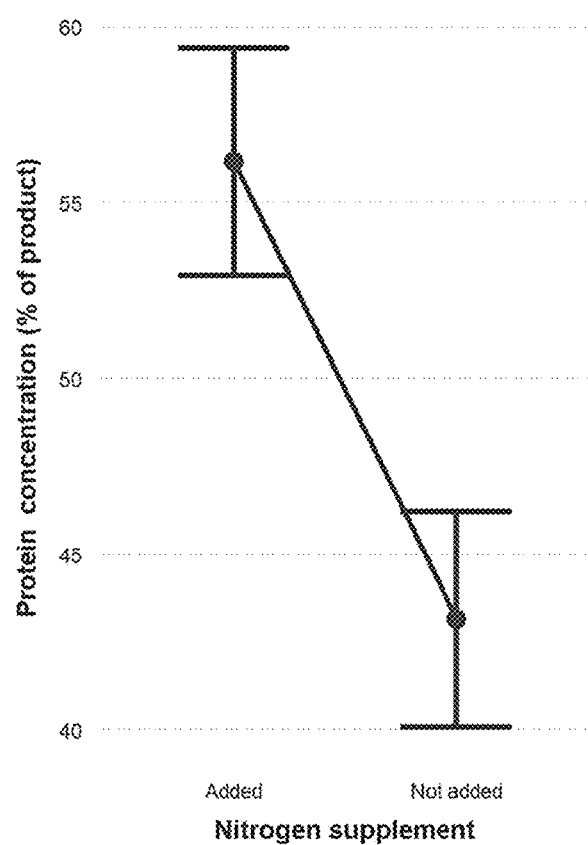

Producing protein food ingredients for blended meats and meat analogs requires that the ingredients have high levels of protein. Most plant-based waste streams that have been disclosed or reported as usable for producing mycelium fungal material have a limited amount of nitrogen that can be consumed and transformed into fungal proteins. Specifically, the amount of protein in raw potato substrate is insufficient to produce a high protein mycelium for use as a good meat replacement product (Table 1). Nitrogen was added to the PS media to determine if added nitrogen could increase the protein levels in the resulting fungal biomass. PS media was prepared by comminuting fresh potatoes (as in Example 20B), with 50% of the peel retained, diluted with water to 11.25 g/l, 22.5 g/l, or 45 g/l of dry matter. PS media was then supplemented with diammonium phosphate and potassium nitrate to 0.5 g/l and 0.75 g/l, respectively, before autoclaving. In other experiments, other nitrogen sources were used, including yeast extract, peptone, urea, ammonia, ammonium, and nitrate salts, or their combinations, not inclusive. 100 ml aliquots of the PS media were transferred in 500 ml Erlenmeyer flasks with 4 replicates for each treatment. Flasks with PS media with and without added nitrogen were inoculated with the freshly harvested $N.$ $intermedia$ conidia to $10^5$ conidia/ml and cultivated at 30° C. with shaking at 200 RPM for 48 hours. The biomass was collected using vacuum filtration with 1.2 μm pore filter disks. Protein concentration was determined by grinding samples to a fine powder and using the Bradford method. The data were analyzed using one-way ANCOVA, controlling for PS concentration, and was followed by Tukey-HSD post-hoc test (FIGS. 10A and 10B). The addition of low-cost inorganic nitrogen to PS media had a significant positive effect on the protein content in the mycelium product and boosted the protein yield. This result was further validated by fermenting solid potato homogenate in external loop fermentors. This demonstrates a simple and cost-effective method to improve mycelium food ingredients that are produced from potato waste.

Fungal protein yield from $Neurospora$ $crassa$ can also be improved by the addition of various nitrogen sources to PS media. PS media was prepared by comminuting solid potato rejects from a French fry producer in a blade homogenizer (as in Example 20B). PS media was supplemented with various nitrogen sources to a total N value of 15 mM. Nitrogen sources included yeast extract (Yeast), diammonium phosphate, potassium nitrate, a combination of diammonium phosphate, potassium nitrate (Ammonium+Nitrate), corn protein (Maize) or corn protein, potassium nitrate, or a combination of Maize and potassium nitrate (Maize and nitrate). The media was sterilized and the experiment was set up, run, and analyzed as above but using inoculation with conidia of $N.$ $crassa.$ All supplemental nitrogen sources improved the protein content (FIG. 10C) of the fungal mycelium material that was produced and increased protein yields compared to non-supplemented PS ("None"). It was found that the protein yield in the $N.$ $crassa$ mycelium food ingredient was increased the most when maize was the source of the nitrogen. The slight reduction seen when maize protein was combined with nitrate may be attributed to a pH shift that was suboptimal but was not controlled in this experiment.

F. The PS-Based Fermentation Process can Tolerate Residual Oil from Potato Processing.

Figure 11:
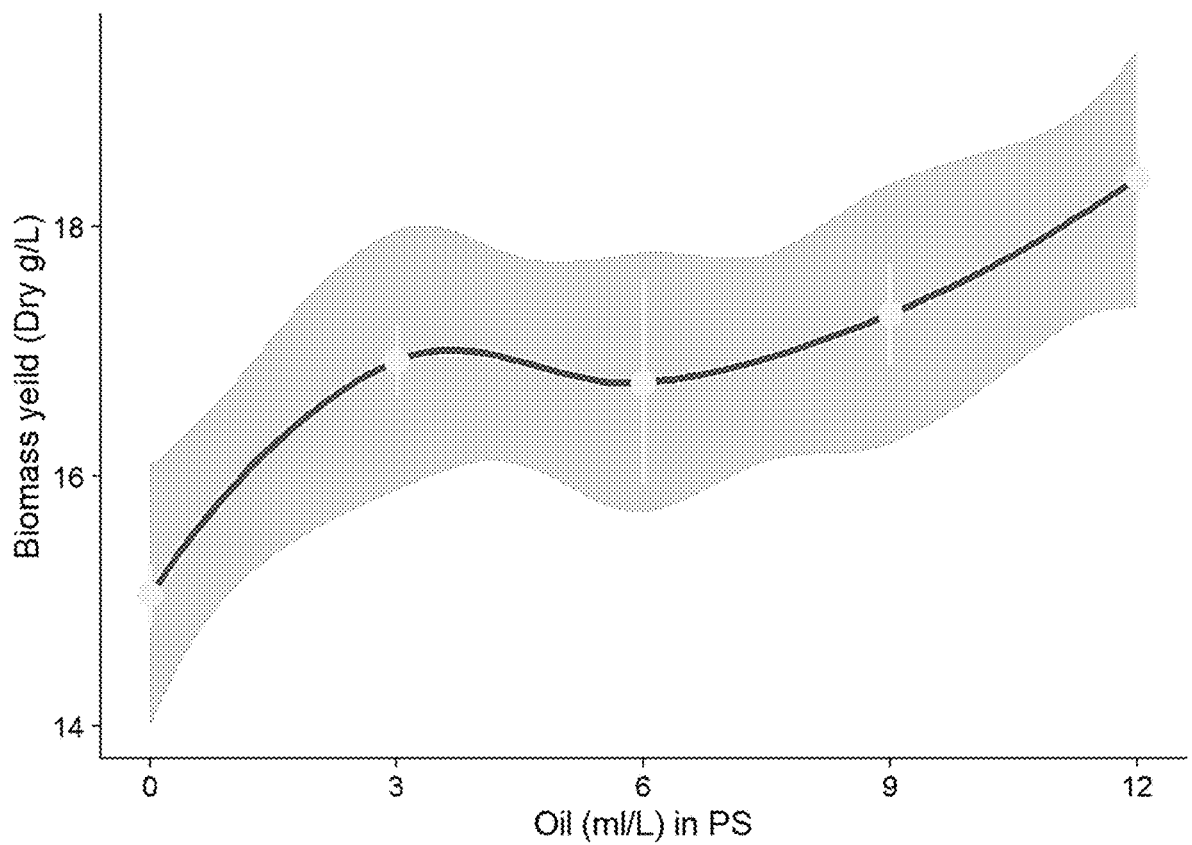
FIG. 11 shows that residual oil in potato solids waste does not hamper the production of mycelium ingredients. Mycelium was grown on potato solids that was supplemented with canola oil before the onset of the fermentation. Biomass was collected and weighed. Points and error bars show means and standard errors, the gray area around the trend line represents a 95% confidence interval.

Potato rejects can include oil residual left from the processing lines and product manufacturing such as French fries or hash browns. Commonly these are plant-based oils. Fermentation of mycelium from solid potato rejects can be affected by residual oil which can inhibit fungal growth and nutrient acquisition. The effect of residual oils on the ability to generate food ingredients from fermentation was evaluated. PS media was prepared by comminuting fresh potatoes (as in Example 20B), with 50% of the peel retained, diluted with water to 45 g/l of dry matter. The PS media was supplemented with various amounts of canola oil, commonly found in solid potato-based products. 100 ml aliquots of the PS media were transferred in 500 ml Erlenmeyer flasks with 4 replicates for each treatment. Flasks with PS media were inoculated with the freshly harvested $N.$ $intermedia$ conidia to $10^5$ conidia/ml and cultivated at 30° C. with shaking at 200 RPM for 48 hours. The biomass was collected using vacuum filtration with 1.2 μm pore filter disks. Oil in the PS media did not negatively impact fungal biomass yield, thus the results demonstrate that fungal mycelium can be produced in the presence of residual oil from potato processing (FIG. 11). This could be an advantage for food ingredients in which oil is routinely added as part of the manufacturing and formulation process.

G. Different Fungal Species can be Used for Culturing Potato Solids.

Figure 12:
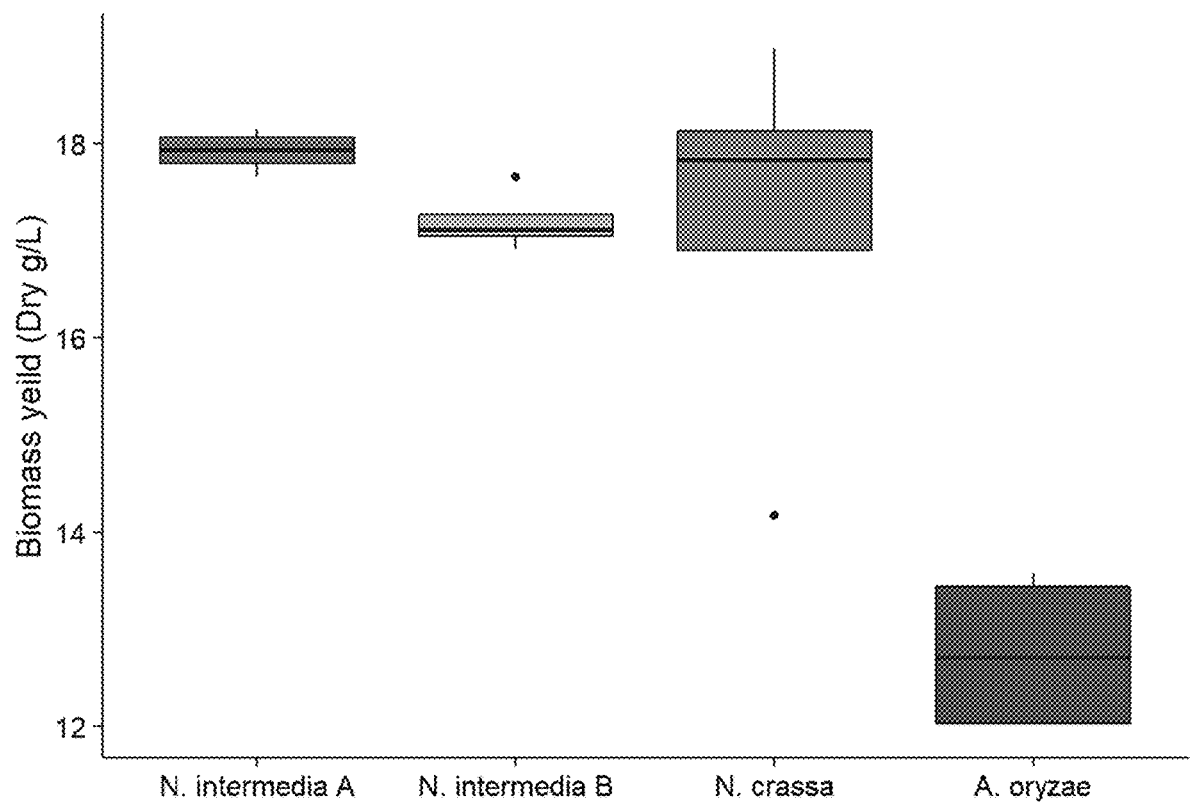
FIG. 12 shows that edible mycelium biomass can be produced from solid potato substrate using different fungal species. MP+ was used to ferment fungal biomass using 2 isolates of *N. intermedia, N. crassa* and *A. oryzae*. After collecting and drying the mycelium the biomass was measured.

It's possible that additional edible ascomycota that are known to saccharify starch could also be used to produce meat-like ingredients from solid potato rejects. MP+ media was prepared as described above in Example 20B by blade homogenizing solid potato material, and then adjusting the dry matter with water to 45 g/l and adding diammonium phosphate and potassium nitrate to 0.8 g/l and 1.2 g/l (MP+ media is potato dry solids of 45 g dry potato solids added per 1 liter of liquid culture media and supplemented with diammonium phosphate and potassium nitrate to a total nitrogen concentration of 15 mM and trace elements). Flasks with media were inoculated to a $10^5$ conidia/ml with fresh conidia of 2 different isolates of $N.$ $intermedia,$ $N.$ $crassa,$ or $A.$ $oryzae.$ Cultures were grown for 48 hours at 30° C. with 200 RPM in a shaker incubator. The mycelium was then collected, dried, and weighed. The results show that all 3 fungal species grow well media comprising comminuted potato solids (FIG. 12). Fungal biomass yield was higher in the $Neurospora$ species when compared to $A.$ $oryzae.$ This example demonstrates that various edible mycelium ingredients can be produced from solid potato substrate by employing different fungal species in the process.

H. Potato Solids Substrate Enhanced Biomass Yield.

Figure 13:
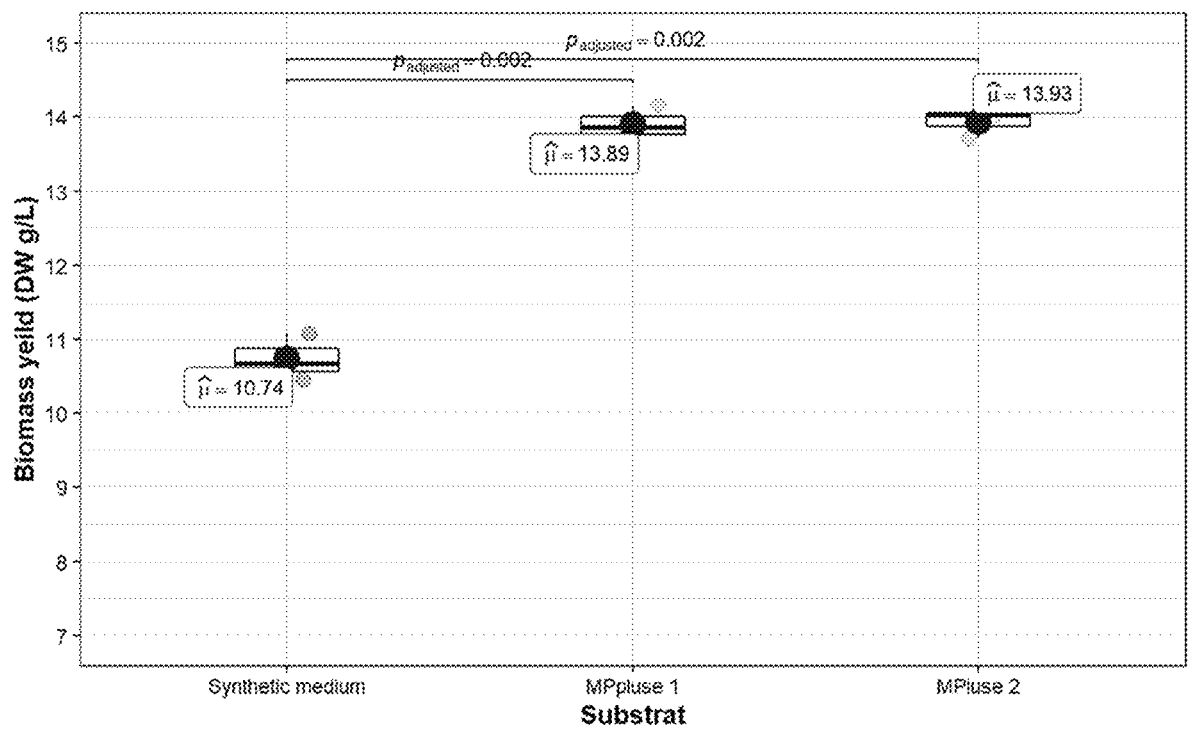
FIG. 13 shows that using media made from potato solids improves the yield of edible mycelium. *N. intermedia* was cultivated on synthetic media alone or with comminuted and diluted solid potatoes (MP+) made in two separate batches. The biomass was harvested and dried before analyzing yield. Mean yields were compared using Yuen's trimmed meat test.
Figure 14A:
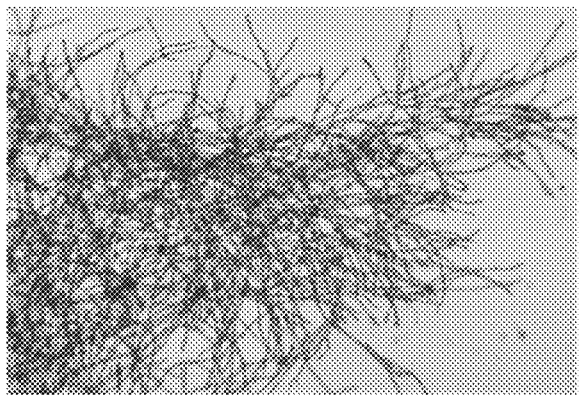
FIGS. 14A-14D show that fermentation of fungi on comminuted potato solids creates a special morphology that is more like meat fiber and is a matrix of undigested plant cells and mycelium. *N. intermedia* was cultivated on glucose based medium (FIGS. 14A and 14B) or MP+ from potato solids (FIGS. 14C and 14D). Samples were phenotyped microscopically after iodine staining.
Figure 14B:
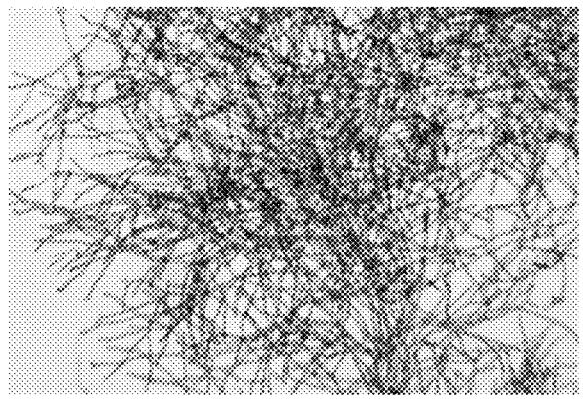
Figure 14C:
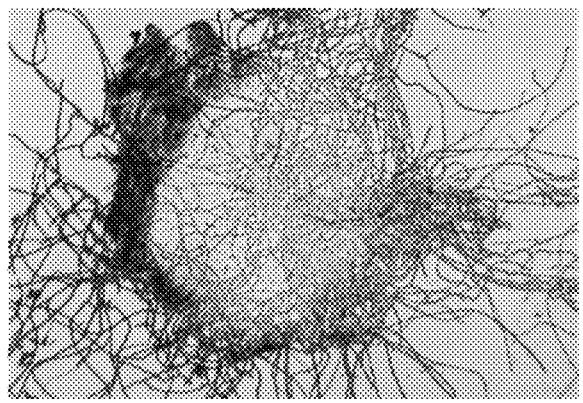
Figure 14D:
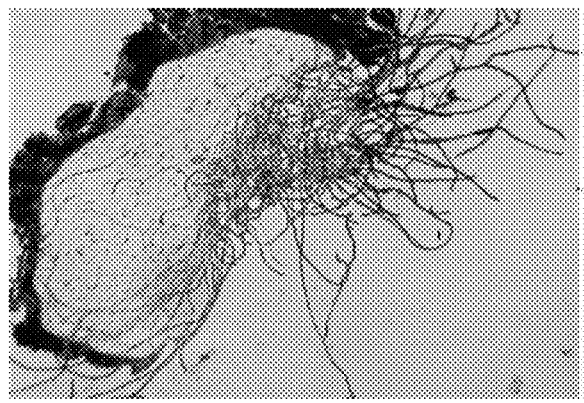

The amount of biomass that was produced with an optimized potato solid medium (MP+, see Example 20G) and a synthetic medium was compared. MP+ was prepared from solid potatoes as in Example 20G. The concentration of nutrients such as carbon and nitrogen in the MP+ was evaluated based on dry matter content, fiber analysis (AOAC 991.43), starch determination (AOAC standard method 996.11) and protein content (AOAC 992.23). A synthetic media with the same amount of carbon and nitrogen as in MP+ was composed of 45 g/l dextrose and 2 g/l yeast and supplemented with diammonium sulfate, potassium nitrate (to a total nitrogen concentration of 15 mM) and trace elements. Aliquots were dispensed into flasks, inoculated with *N. intermedia* conidia to $10^5$ conidia/ml and cultivated at 30° C. with shaking at 200 RPM in an incubator for 48 hours. The fungal biomass was collected using vacuum filtration with 1.2 µm pore filter disks. After overnight drying at 60° C. the dry weight (DW) of the biomass was compared using ANOVA and pairwise comparisons (FIG. 13). Surprisingly, it was discovered that using potato solids significantly (p=0.002) enhanced the yield of the fungal biomass. The results demonstrate a significant advantage to using potato solids based growth media.

I. Using Potato Solids Changes the Morphology of the Fungal Growth and Creates Improved Meat-Like Fiber Structure.

The texture of a fungal mycelium-based meat substitutes is greatly impacted by the morphology of the filaments. Meat is composed of elongated cellular fibers, thus in order to produce good meat analogues it is desirable to have long mycelial filaments. The morphology of *N. intermedia* mycelium grown on comminuted potato solids was compared with the morphology seen when fermentation was carried out on a synthetic medium (as in Example 20H). MP+ potato media (Example 20G) was prepared and synthetic media was composed of 45 g/l dextrose, 2 g/l yeast, diammonium sulfate, potassium nitrate and trace elements. Media was dispensed into 2.8 flasks, inoculated with *N. intermedia* conidia to $10^5$ conidia/ml and cultivated at 30° C. with shaking at 150 RPM in an incubator for 48 hours. Samples were collected and stained for starch with iodine and evaluated under the microscope (FIG. 14). When fungi was fermented on potato solids the morphology was less dense and more elongated. It was found that the mycelium grew on and around microscopic granules of potatoes. This generated a unique matrix structure composed of fungal cells and residual plant fibers and starch. This morphology may be more like animal meat from skeletal muscles which contains about 90% muscle fibers. When the mycelium produced from potato solids was combined into a meat-like analogue, this unique matrix created a texture that performed better as a meat-like product compared to mycelium that was produced in the regular process (see FIG. 19). Since some starch was observed under the microscope (AOAC standard method 996.11) the amount of residual starch at the end of a fermentation process in a 5 L bioreactor when using potato solids was measured. It was found that only a small amount (7.22%) of the dried fungal biomass was made of residual starch.

Figure 15:
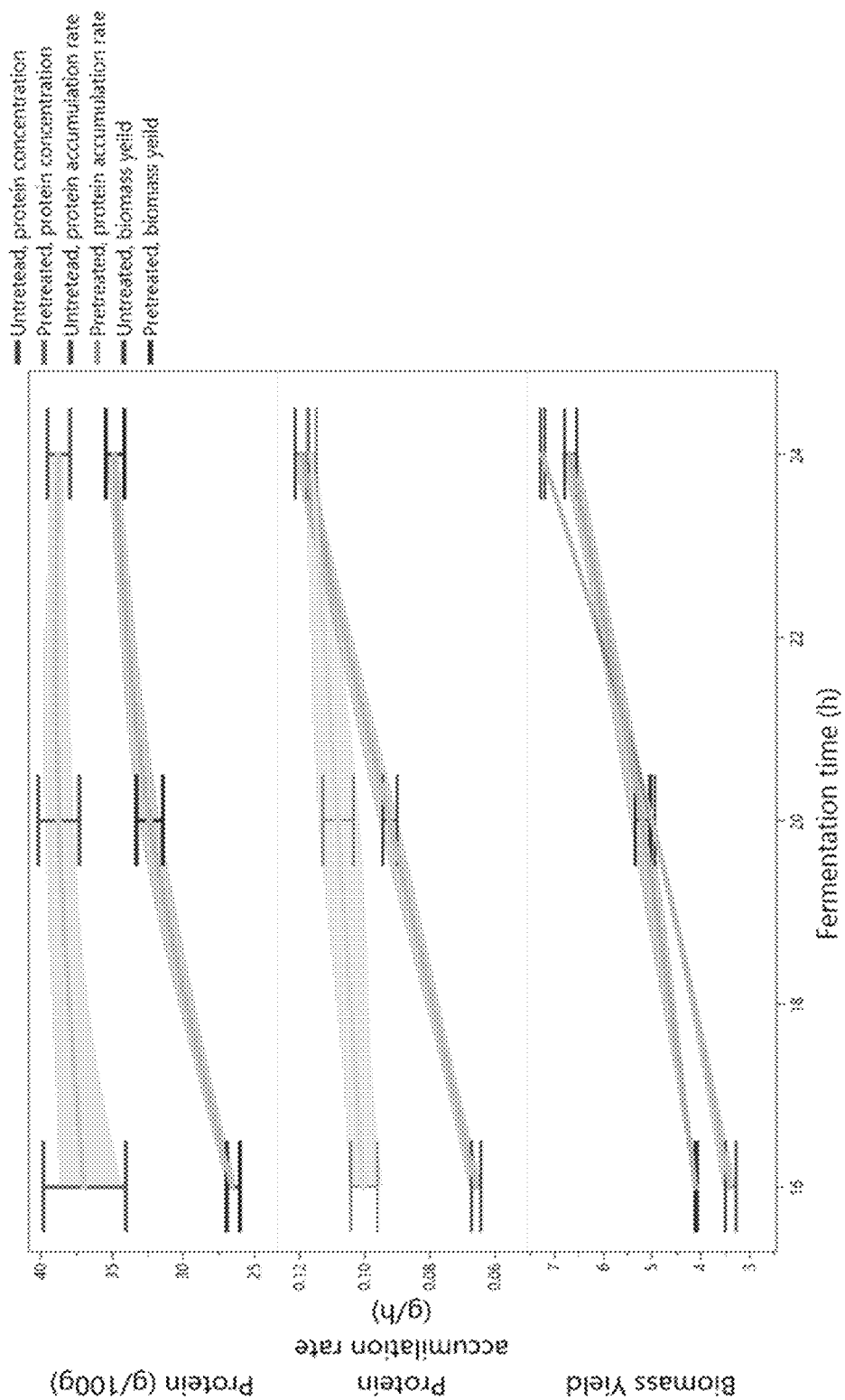
FIG. 15 shows that hydrolyzing the starch in solid potatoes accelerates and increases protein accumulation. *N. crassa* was cultivated on potato solids that was either treated or not with starch degrading alpha-amylase. Harvested mycelium biomass was dried, weighed, and analyzed for protein content after 16, 20, and 24 hours of cultivation.

J. Hydrolyzing Solid Potato by-Products Before the Fermentation Accelerates Protein Accumulation During the cultivation of filamentous fungi on PS media, the starch is broken down by fungal secreted amylases and glucoamylases enzymes. Saccharified monosaccharides are then readily absorbed by the growing hyphae. It is reported in the literature that enzymatic saccharification of starches is advantageous before microbial fermentation to make the carbohydrate more available. For example, Moo-Young et al. (U.S. Pat. No. 4,938,972) teach that hydrolyzing cereal milling by-products (carbon-rich starch) improve the bioconversion of the carbon during the fermentation into biomass. Nojiri et al. (U.S. Pat. No. 4,230,806) teach that starch can be liquefied by enzymatic pre-treatment and then be used for the cultivation of yeast. However, filamentous fungi, such as *Neurospora*, can convert starch to biomass as they natively possess and secrete starch degrading enzymes. Therefore, such pre-treatment is not expected to have an impact on mycelium production. In short, prior-art teaches that starch hydrolysis can improve fungal biomass production as it is directly related to carbon availability from the starch and/or is beneficial for microbes, such as yeast, that cannot consume starch directly. The impact of hydrolyzing raw potato material in the MP+ media on mycelium biomass production was evaluated with *N. crassa*. Comminuted raw potato rejects from a food processing facility were heated in the presence of 0.5 ml per 1 liter of media of a thermostable alpha-amylase (Megazyme item number E-BSTAA) enzyme. It was determined that for the specific activity of this enzyme preparation 100° C. for 1 hour was enough to saccharify and liquefy the starch. This gave a maximal residual starch of 10% of the original content and measured using on starch assay (Megazyme item number TSTA-100A). This substrate was then used to formulate MP+ media as described above (Example 20G). As a control, the same media was prepared but without the addition of enzyme. 100 ml aliquots of the MP+ media were transferred in 500 ml Erlenmeyer flasks with 5 replicates for each treatment. Flasks with MP+ media were inoculated with the freshly harvested *N. crassa* conidia to $10^5$ conidia/ml and cultivated at 30° C. with shaking at 200 RPM for 24 hours. Biomass was collected after 16, 20, and 24 hours using vacuum filtration with 1.2 µm pore filter disks, dried at 60° C., and weighed. Protein concentration was determined after grinding samples and using method AOAC 2011.04 (FIG. 15). The results show that there was no significant difference in the accumulation rate of mycelium biomass when the potato starch was enzymatically pretreated in the PS media (bottom panel). Surprisingly and unexpectedly the rate of protein accumulation (FIG. 15 middle panel) in the mycelium and the maximal protein concentration (FIG. 15 upper panel) were significantly higher when the PS media was enzymatically treated before the fermentation. This was not expected since the enzymatic pretreatment should impact only the availability of carbon in the media, but not the nitrogen that is needed for protein production. Since this type of hydrolysis shortens the production cycles of mycelium meat-like ingredients it makes them more economical and has therefore a major impact on culturing mycelium on solid potato rejects.

K. Reducing the Particle Size of the Potato Solids by Homogenization Improves the Protein Content in the Cultured Mycelium.

Figure 16:
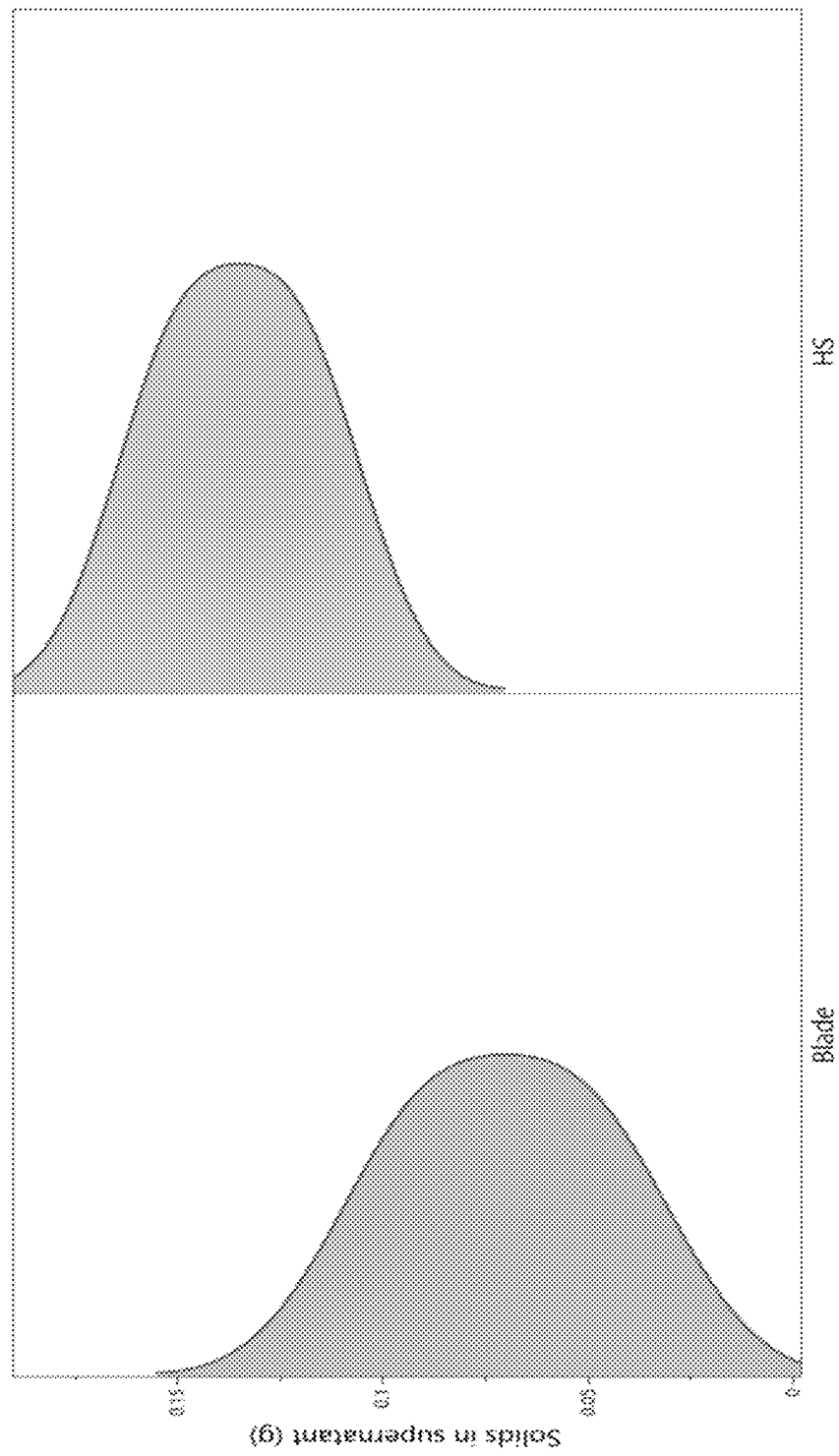
FIG. 16 shows that high-shear homogenization of solid potato rejects enables higher size reduction of particles. Distribution plot of potato solids that did not precipitate after applying centrifugal force. Higher values indicate a smaller particle size.

Liquification by enzymatic hydrolysis and saccharification of potato solids rejected before mycelium cultivation can be time-consuming and costly. Therefore, the application of different homogenization methods and the impact they might have on the mycelium biomass that is produced was tested. First, potato solid rejects from food processing were comminuted in water using either a blade homogenizer (Waring) or a high-sheer (HS) homogenizer (Silverson MX5). The particle sizes were evaluated by centrifuging samples for 30 seconds at 13,000×g and measuring the weight of solids that did not precipitate relative to total solids in a sample (FIG. 16). HS resulted in an average particle size of about 20-50 µm, while blade homogenization resulted in an average particle size of about 100-200 µm. At a given acceleration speed smaller particles will not sediment. This analysis demonstrated that the HS method produced smaller particles compared to blade homogenization. A microscopic analysis supported this observation and indicated that particle sizes were reduced to a median of 20-50 µm by the HS method.

Figure 17:
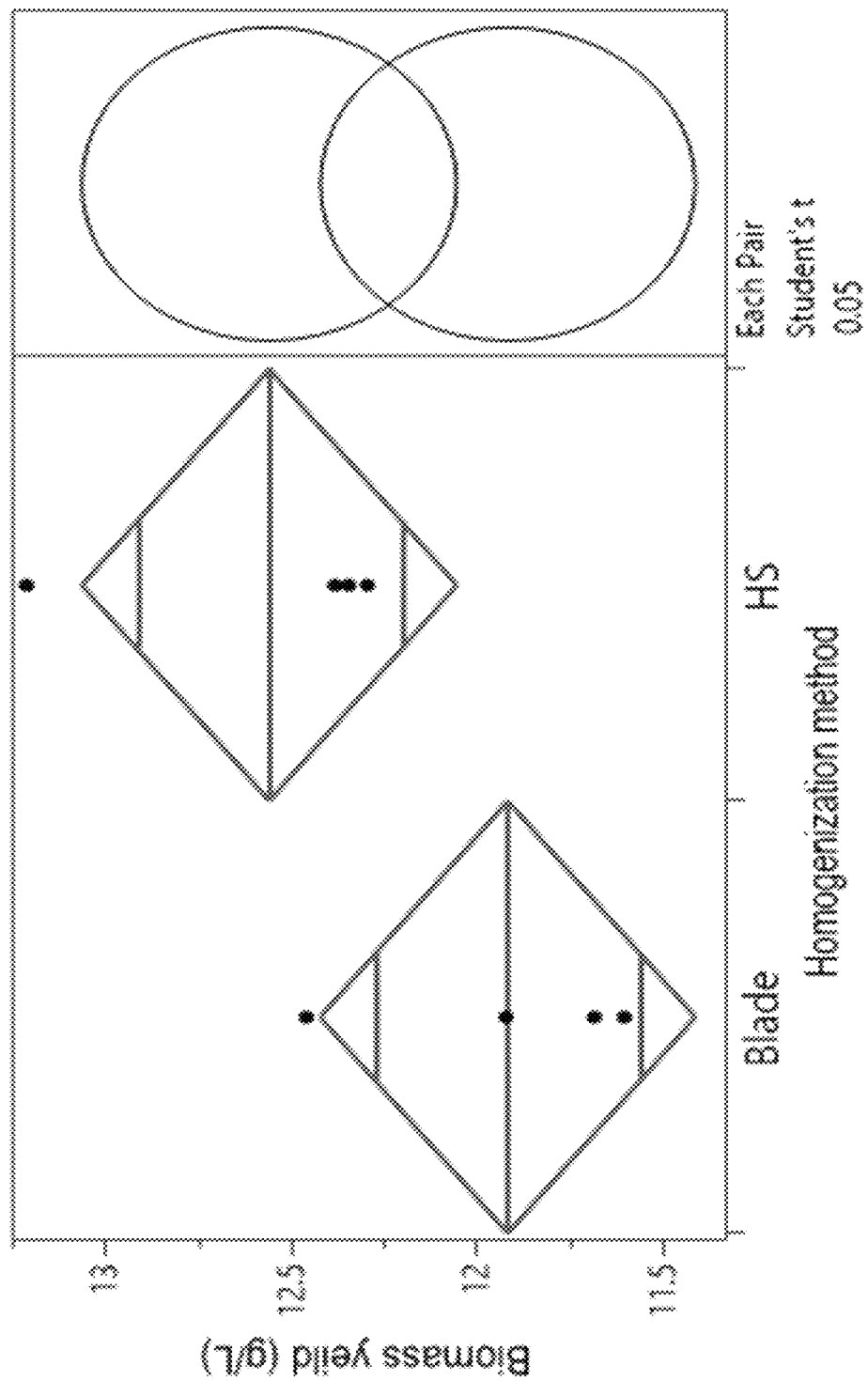
FIG. 17 shows that there is no difference in biomass yield of edible mycelium from potato solids with different particle sizes. Diamonds represent confidence intervals. Overlapping circles on the right represent pairs without a statistically significant difference.
Figure 18:
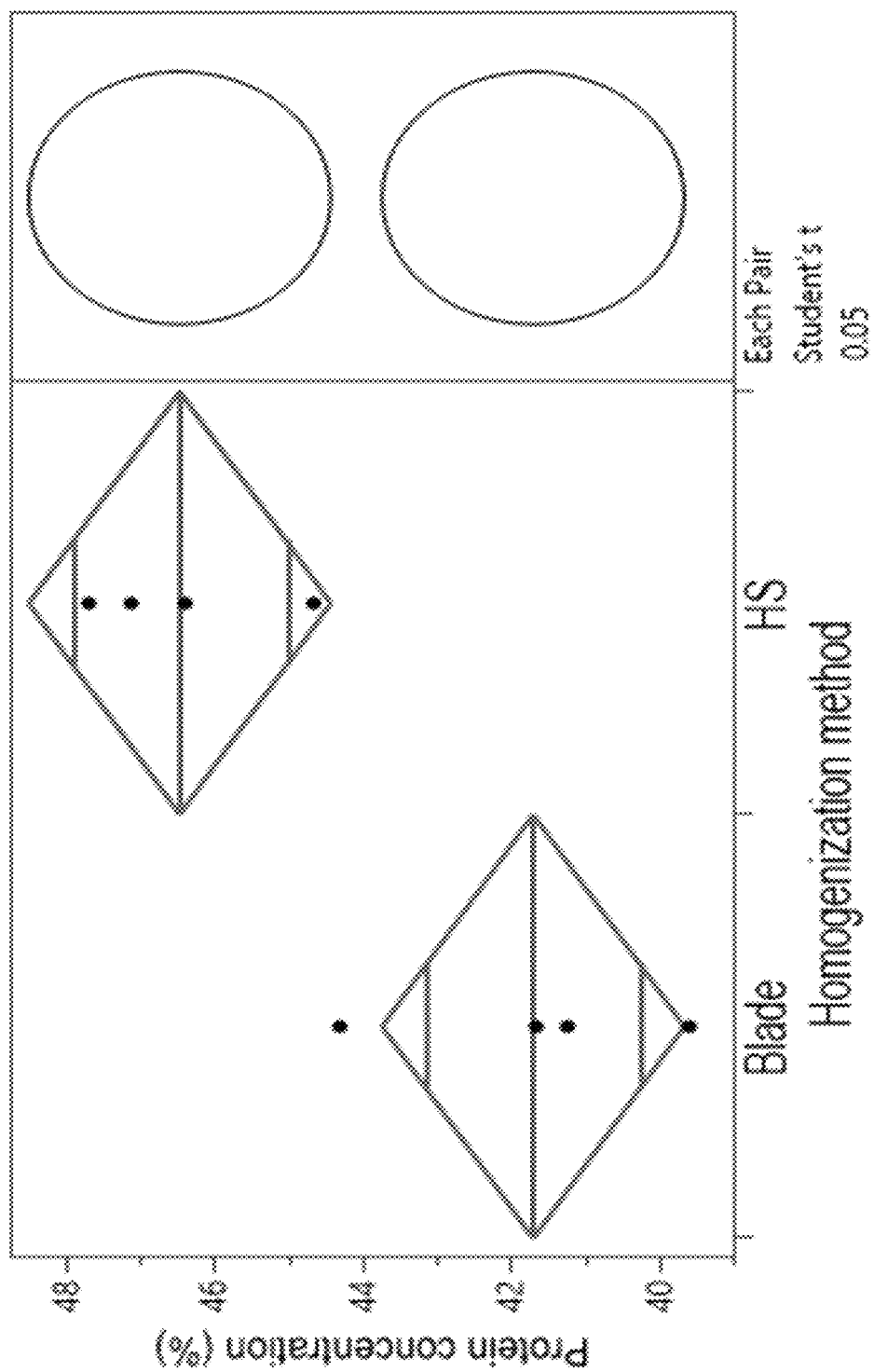
FIG. 18 shows that edible mycelium biomass that was generated from potato solids with a smaller particle size has higher protein content. Diamonds represent confidence intervals. Nonoverlapping circles on the right represent pairs with statistically significant differences.

To evaluate the impact of different particle size reductions on mycelium production, MP+ media was prepared from potato solids that were comminuted by either Blade or HS methods. Comminuted potato solid rejects were diluted with water to 45 g/l, supplemented with 0.8 g/l and 1.2 g/l of diammonium phosphate and potassium nitrate, respectively. Aliquots of 90 ml sterilized media were aseptically dispensed into 250 ml flasks and 4 replicates were inoculated with conidia of *N. crassa*. Cultures were incubated with shaking at 30° C. for 48 hours. Mycelium biomass was harvested using a vacuum filter (Rocker MF Magnetic funnel, Steriletech, Inc) to about 80% moisture. The mycelium disks were further dried to about 5% moisture in forced air oven set to about 60° C. Dry biomass was measured and analyzed for protein content using method AOAC 2011.04 (FIGS. 17 and 18). Means were compared using ANOVA followed by a Student's t-test. It was found that smaller particle size (from HS homogenization) of the potato solids in the media led to slightly higher biomass production (FIG. 17). Unexpectedly and surprisingly, it was discovered that reducing the particle size of solid potatoes in PS media significantly increased the protein content in the generated mycelium food ingredient (FIG. 18). This finding revealed that a smaller particle size reduction (less than about 50 μm; using HS), enables a generation of edible mycelium with improved protein content.

L. Chicken Cutlet.

*N. intermedia* mycelium slurry was prepared by growing the fungi on MP+ as described above ("Fermentation methods for the production of wet and dry fungal potato product"). The biomass was harvested through a nylon mesh bag, washed and vacuum filtered to remove residual water. The mycelium was pasteurized by steam heating to 75° C. Part of the mycelium was used as pressed "wet cake" ingredient. Another part of the mycelium biomass was shredded in a tine and spindle apparatus (Fusion Tech Inc. SH-5 Shredder) and dried at 60° C. to form shelf-stable ingredient made of particles with at size range of 5-50 mm and water content of about 6%.

The wet cake ingredient at 68.59% moisture was combined with dry shelf-stable ingredients of the present disclosure as well as other plant ingredients known to one skilled in the art of making meat analogues. The dry particles and wet cake ratio were mixed at a 1:4 ration to a 20% rate of the final product. Plant protein isolate mix was added to 18% oil to 3% and chicken plant-based flavors were added to 2.5%. Binders and oil were added to 3.5% and the water were added to a final hydration of 53%. The mixture was homogenized and formed into the desired chicken breast shape. The chicken breast was seared, and the texture was set on a grill at 250° C. The cutlet was done cooking when the internal temperature reached 75° C.

M. Steak Product.

*N. intermedia* mycelium slurry was prepared by growing the fungi on MP+ as described above ("Fermentation methods for the production of wet and dry fungal potato product"). Fermentation was carried for 48 hours in a 25 liter stainless steel bioreactor. First, MP+ media was sterilized by autoclaving and was loaded aseptically into the steam sterilized bioreactor. Then the MP+ media was inoculated with a 48 h pre cultivated mycelium seed culture at 1% rate. The bioreactor was maintained at 30° C. and aerated with filter (0.2 μm) sterile air at 1 VVM.

The mycelium biomass was harvested through a nylon mesh bag, washed and vacuum filtered to remove residual water. The mycelium was pasteurized by steam heating to 75° C. Part of the mycelium was used as pressed "wet cake" ingredient. Another part of the mycelium biomass was shredded in a tine and spindle apparatus (Fusion Tech Inc. SH-5 Shredder) and dried at 60° C. to form shelf-stable ingredient of particles with an average size of 8 mm and a moisture of about 7%.

The dry shelf-stable ingredient particles were combined with the wet cake ingredient at a 1:4 ratio. The mycelium biomass mix was set at a final rate of 30% and a variety of plant derived ingredients were incorporated: 10% protein, 3% binder, 3% oil and 4% salt, meat flavoring and colors. Water was added to 50% moisture. The material was thoroughly mixed, then formed into a steak form. The steak cut was then cooked at 250° C. on a stovetop griddle until the internal temperature reached 73° C. (about 4 minutes).

N. Meat Analogue from a Mycelium Product that is Generated from Solid Potatoes Substrate is Preferred by Testers.

Figure 19:
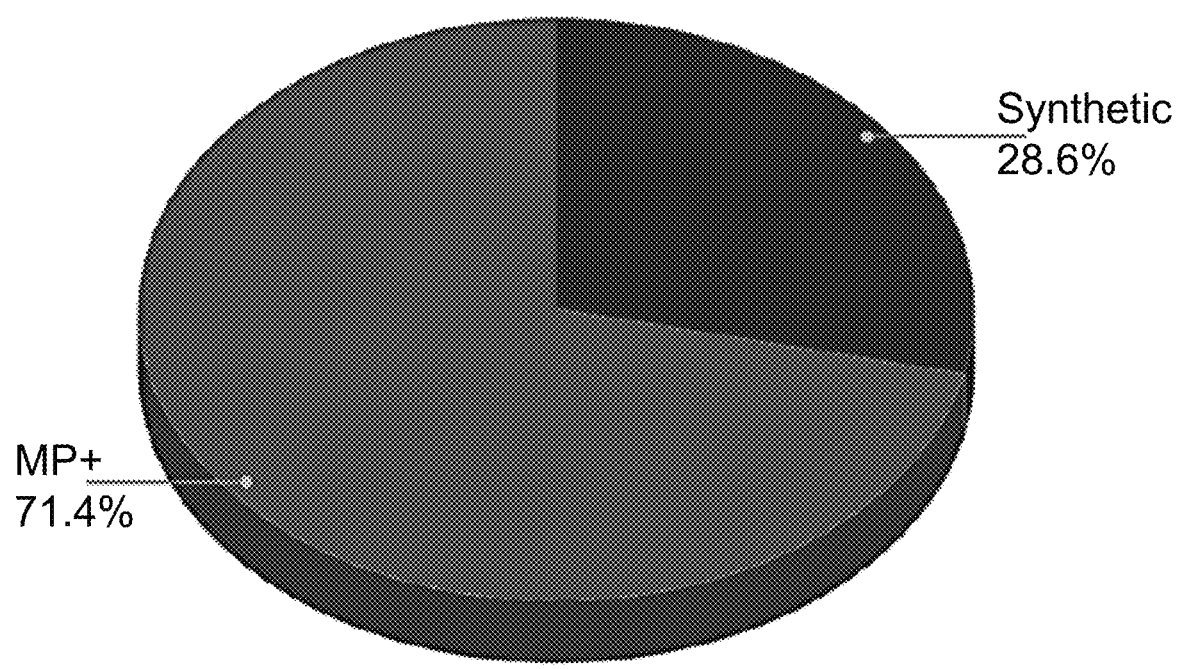
FIG. 19 shows the results of a taste test to compare hamburgers prepared with two different fungal products. MP+ fungal product was produced with fermentation using potato solids substrate, and synthetic was produced with a fermentation process using synthetic media without potato solids.

Meat analog product from dry mycelium produced from media comprising potato solids was compared to dry mycelium produced from a synthetic medium without potato solids (Example 20H). Dry particles of the present disclosure were prepared by growing *N. crassa* mycelium on MP+ as described above (Example 20G). Fermentation was carried for 48 h in a 25 liter stainless steel bioreactor. First, MP+ or synthetic media were sterilized by autoclaving and media were loaded aseptically into the steam sterilized bioreactors. Then the media were inoculated with a 48 hour pre-cultivated *N. crassa* mycelium seed culture at 1% rate. The bioreactors were maintained at 30° C. and aerated with filter (0.2 μm) sterile air at 1 VVM. At the end of the fermentation the mycelium biomass was harvested through a nylon mesh bag, washed and vacuum filtered to remove residual water. The biomass was shredded in a tine and spindle apparatus (Fusion Tech Inc. SH-5 Shredder), dried at 60° C. and pasteurized by dry steam to form shelf-stable ingredient particles of an average size of 8 mm in length, and 3 mm in width and thickness, and a moisture of about 5%. Dry mycelium particles that were produced with MP+, or with synthetic media, were combined with plant-based ingredients to form a burger product formula. Mycelium particles of each type were added to 34 g/100 g with 3 g/100 g binder, 2.5 g/100 g salt and plant-based meat favor and color and protein powder to 1 g/100 g. The material was hydrated with water to about 60% and formed into burger patties. The patties were cooked at 230° C. on a stove top griddle until the internal temperature reached 75° C. Burger samples that were formulated with both types of ingredient were presented to a group of tasting panelists in a blind triangle test followed by preference test (FIG. 19). Panelists overwhelmingly preferred (at a ratio of 1:2.5) a finished product composed of fungal biomass cultured using potato solids. This demonstrated a consumer preference for a product produced from fermentation using potato solids, and that this is superior to fermentation with synthetic media without potato solids, and was processed and formulated the same way.

What is claimed is:

1. A method of producing a shelf-stable food ingredient from filamentous fungal biomass, the method comprising:

c) culturing a filamentous fungi from the genus *Neurospora* or *Aspergillus* in a liquid growth medium to produce the filamentous fungal biomass slurry comprising about 0.5-8% biomass, wherein the liquid growth medium comprises potato solids comminuted to a size of about 20 μm to 50 μm and at a concentration of about 5 g to about 50 g of dry weight per liter of liquid growth medium;

d) harvesting and dewatering the filamentous fungal biomass slurry to produce a harvested filamentous fungal biomass comprising about 60-85% water and about 15-40% filamentous fungal biomass;

e) shredding the filamentous fungal biomass to form filamentous particles and drying the filamentous particles to about 4% to about 10% water, or to about 4% to about 6% water; and f) sizing the dried filamentous particles to comprise a mean particle size between about 5 mm and about 20 mm or between about 5 mm and about 50 mm to produce a self-stable food ingredient comprising sized dried filamentous particles having a residual potato content ranging from about 0.1 g to about 10 g per 100 g of dried filamentous particles or about 1 g to about 5 g per 100 g of dried filamentous particles.

2. The method according to claim 1, further comprising g) hydrating the sized dried filamentous particles to about 30% to about 70% water content to form a hydrated food product.

3. The method of claim 1, wherein the liquid growth medium further comprises one or more nitrogen sources, starches, fatty acids, sugars, minerals, trace elements, vitamins, extracts, or combinations thereof.

4. The method of claim 1, wherein the potato solids comprise about 1% to about 60% peel retained potato solids; about 10 g to about 40 g starch per 100 g wet potato solids; about 1 g to about 5 g protein per 100 g wet potato solids, and a pH of about 5 to about 6.

5. The method of claim 1, wherein the potato solids are hydrolyzed prior to adding to the liquid growth medium.

6. The method of claim 2, further comprising pasteurizing the food product.

7. The method of claim 2, further comprising shaping the food product into patties, nuggets, balls, or sausage links.

8. The method of claim 2, wherein the food product comprises protein in an w/w amount of 5-100%, 5-75%, 5-50%, 5-45%, 5-40%, 5-35%, 5-30%, 5-25%, 5-20%, or 5-15%.

9. The method of claim 2 further comprising combining the food product with plant ingredients, one or more natural flavorings, or both, wherein the one or more natural flavorings is a natural chicken flavoring, a natural beef flavoring, or a natural pork flavoring.

10. The method of claim 2 further comprising mixing the food product with a ground meat to produce a meat blended food product.

11. The method of claim 10, wherein the ground meat is selected from the group consisting of beef, pork, chicken, turkey, fish, lamb, crab, lobster, venison, bison, and combinations thereof.

12. The method of claim 10, wherein the meat blended food product comprises at least about 5% w/w of the food product and at least about 10% w/w of the ground meat.

13. The method of claim 10, wherein the meat blended food product comprises at least about 5% w/w of the food product and at least about 10% w/w of the meat and wherein the food product comprises protein in an w/w amount of 5-100%, 5-75%, 5-50%, 5-45%, 5-40%, 5-35%, 5-30%, 5-25%, 5-20%, or 5-15%.

14. The method of claim 10, wherein the meat blended food product comprises protein in an w/w amount of 5-100%, 5-75%, 5-50%, 5-45%, 5-40%, 5-35%, 5-30%, 5-25%, 5-20%, or 5-15%.

15. The method of claim 2, wherein the food product is ground into a flour before blending with a ground meat.

16. The method of claim 2 further comprising combining the food product with plant ingredients.

17. The method of claim 1, wherein the filamentous species are *Neurospora intermedia*, *Neurospora sitophila*, *Neurospora crassa*, *Aspergillus oryzae*, or a combination of *Neurospora intermedia*, *Neurospora crassa*, *Neurospora sitophila*, and *Aspergillus oryzae*.

18. The method of claim 2, wherein the dried filamentous particles are sized by continuous sieving using 2 mm and 12 mm sieves.

19. The method of claim 1, wherein about 10 g, about 11 g, about 12 g, about 13 g, about 14 g, about 15 g, about 16 g, about 17 g, about 18 g, about 19 g, or about 20 g or more of the filamentous fungal biomass slurry is produced per liter of liquid growth medium.

20. A method of producing a filamentous fungal biomass, the method comprising:

h) culturing a filamentous fungi from the genus *Neurospora* or *Aspergillus* in a liquid growth medium to produce the filamentous fungal biomass slurry comprising about 0.5-8% biomass, wherein the liquid growth medium comprises potato solids comminuted to a size of about 20 μm to 50 μm and at a concentration of about 5 g to about 50 g of dry weight per liter of liquid growth medium; and i) harvesting and dewatering the filamentous fungal biomass slurry to produce a harvested filamentous fungal biomass comprising about 60-85% water and about 15-40% filamentous fungal biomass having a residual potato content ranging from about 0.5 g to about 5 g per 100 g of filamentous fungal biomass or about 1 g to about 5 g per 100 g of filamentous fungal biomass.

21. The method of claim 20, wherein the liquid growth medium further comprises one or more nitrogen sources, starches, fatty acids, sugars, minerals, trace elements, vitamins, extracts, or combinations thereof.

22. The method of claim 20, wherein the potato solids comprise about 1% to about 60% peel retained potato solids; about 10 g to about 40 g starch per 100 g wet potato solids; about 1 g to about 5 g protein per 100 g wet potato solids, and a pH of about 5 to about 6.

23. The method of claim 20, wherein the potato solids are hydrolyzed prior to adding to the liquid growth medium.

24. The method of claim 20, further comprising pasteurizing the filamentous fungal biomass.

25. The method of claim 20, wherein the filamentous fungal biomass comprises protein in an w/w amount of 5-100%, 5-75%, 5-50%, 5-45%, 5-40%, 5-35%, 5-30%, 5-25%, 5-20%, or 5-15%.

26. The method of claim 20, wherein the filamentous species are *Neurospora intermedia*, *Neurospora sitophila*, *Neurospora crassa*, *Aspergillus oryzae*, or a combination of *Neurospora intermedia*, *Neurospora crassa*, *Neurospora sitophila*, and *Aspergillus oryzae*.

* * * * *